(12) United States Patent
Soltane et al.

(10) Patent No.: US 11,266,632 B1
(45) Date of Patent: Mar. 8, 2022

(54) MASLINIC AND OLEANOLIC ACIDS DERIVATIVES FOR TREATING SARS-COV-2 INFECTION

(71) Applicant: King Abdulaziz University, Jeddah (SA)

(72) Inventors: Raya Soltane, Jeddah (SA); Hani Abdullah Alhadrami, Jeddah (SA); Ahlam Alasiri, Jeddah (SA); Hichem Ben Jannet, Jeddah (SA); Karim Chouaib, Jeddah (SA); Amani Chrouda, Jeddah (SA); Ahmed Mostafa, Jeddah (SA); Rami Adel Pashameah, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/380,325

(22) Filed: Jul. 20, 2021

(51) Int. Cl.
| | |
|---|---|
| *A61K 31/21* | (2006.01) |
| *A61K 31/425* | (2006.01) |
| *A61K 31/42* | (2006.01) |
| *A61P 31/14* | (2006.01) |
| *A61K 31/215* | (2006.01) |
| *A61K 31/4192* | (2006.01) |

(52) U.S. Cl.
CPC ............ *A61K 31/42* (2013.01); *A61K 31/215* (2013.01); *A61K 31/4192* (2013.01); *A61P 31/14* (2018.01)

(58) Field of Classification Search
CPC ... A61K 31/215; A61K 31/4192; A61K 31/42
USPC ........................................ 514/510, 359, 378
See application file for complete search history.

(56) References Cited

U.S. PATENT DOCUMENTS 10,729,735 B1   8/2020   Newman

FOREIGN PATENT DOCUMENTS

WO   WO-2016095830 A1 *  6/2016 .............. A61P 31/04

OTHER PUBLICATIONS

Holmes et al. "Coronaviridae: The viruses and their replication," Chapter 34, Fields Virology, vol. 1, pp. 1075-1076, Third Edition, 1995. (Year: 1995).*
Consult QD "Coronavirus have been around for centuries: What differentiates COVID-19?" May 2020, Padiatrics /News & Insights, https://consultqd.clevelandclinic.org/coronaviruses-have-been-around-for-centuries-what-differentiates-2019-ncov/ (Year: 2020).*
Sampangi-Ramaiah et al., "Molecular docking analysis of selected natural products from plants for inhibition of SARS-CoV-2 main protease" Current Science, vol. 118, No. 7, Apr. 10, 2020.
Pawelczyk et al., "Anti-COVID drugs: repurposing existing drugs or search for new complex entities, strategies and perspectives", FutureMed. Chem. Epub ahead of print, 2020.
Mishra et al., Natural compounds as potential inhibitors of novel coronavirus (COVID-19) main protease: An in silico study, 0.21203/rs.3.rs-22839/v1 research sqaure, preprint available, Apr. 2020.

(Continued)

*Primary Examiner* — Shengjun Wang
(74) *Attorney, Agent, or Firm* — WC&F IP

(57) ABSTRACT

Provided are methods of using oleanolic acid and derivatives for treating coronavirus infection. The method includes using propargyl-moiety containing oleanolic acid derivatives for inhibiting coronavirus growth by impairing the viral replication of SARS-CoV-2 through inhibition of the viral function of SARS-CoV-2 main protease.

6 Claims, 40 Drawing Sheets

(56) References Cited

OTHER PUBLICATIONS

Vardhan et al.,"In silico ADMEI and molecular docking study on searching potential inhibitors from limonoids and triterpenoids for COVID-19", arxiv.org 2020.

Xiao et al., Recent progress in the antiviral activity andmechanism study of pentacyclic triterpenoids and their derivatives, Med Res Rev 2018;38:951-976. 2018.

Diniz et al., "Bioactive Terpenes and Their Derivatives as Potential SARS-CoV-2 Proteases Inhibitors from Molecular Modeling Studies", Biomolecules, 11, 74. doi.org/10.3390/biom11010074, 2021.

Thi et al.,"Synthesis and cytotoxic evaluation of novel ester-triazole-linked triterpenoid-AZT conjugates", Bioorg. Med. Chem. Lett. 24, 5190-5194, 2014.

\* cited by examiner

MASLINIC AND OLEANOLIC ACIDS DERIVATIVES FOR TREATING SARS-COV-2 INFECTION

FIELD OF THE INVENTION

The disclosure provides a method of using triterpenoids for treating coronavirus infection. In particular, the method includes using maslinic and oleanolic acids triterpenoids derivatives in SARS-CoV-2 infection treatment. The antiviral property of the derivative compounds is based on their ability to impair the viral replication of SARS-CoV-2 by disturbing a viral function of SARS-CoV-2 main protease.

BACKGROUND

Coronaviruses (CoVs) are positive single-stranded (+ss) RNA viruses that are classified within the family Coronaviridae. The infectious bronchitis virus (IBV) was the first-discovered CoV that caused an outbreak of respiratory illness in chickens in the 1930s. Reports on mouse hepatitis virus (MHV) and transmissible gastroenteritis virus (TGEV) that infected mice and pigs, respectively, followed in the 1940s. In humans, HCoV-229E and HCoV-OC43, were identified in the 1960s as the causative agents of mild respiratory diseases that present as common cold. Since then, five other HCoVs were identified at different times, including Severe Acute Respiratory Syndrome-CoV (SARS-CoV) in 2003, HCoV-NL63 in 2004, HCoV-HKU1 in 2005, Middle East Respiratory Syndrome-CoV (MERS-CoV) in 2012, and the most recently discovered Severe Acute Respiratory Syndrome-CoV-2 (SARS-CoV-2) in December 2019.

Since its emergence, SARS-CoV-2 infection subsequently expanded to all over the world in a very short period of time. To date, 160 million people have been infected with mortality and morbidity still rising in various parts of the world. As a result, there has been a thrust towards rapid development of vaccines and anti-rival drugs against SARS-CoV-2 to combat the rapidly spreading of the viral infection as well as to provide effective treatment options for patients. Several antiviral-drugs have been approved by the FDA for their uses in SARS-CoV-2 patient treatments [1-3]. In parallel, several clinical trials to virtually recommend or practically test the anti-SARS-CoV-2 activity of synthetic compounds, natural extracts and immunomodulatory agents have been attempted [4-7].

Triterpenes are a class of natural molecules made up of 30 carbon atoms. There are about 200 different skeletons known to date, which are isolated from natural sources of the cyclization of (3S)-2,3-epoxy-2,3-dihydrosqualene and sometimes from squalene itself. These molecules are in most cases hydroxylated at C-3 position due to the opening of the epoxide during cyclization [8]. In the plant kingdom, terpenoids are secondary metabolites, whose ecological role has been proven, especially in the process of communications and defense. Triterpenes, of which more than 30,000 structures are previously isolated and characterized, are derived from natural sources or enzymatic reactions. Additionally, they comprise 47 sub-classes with enormous chemical diversity [8-11]. Triterpenes are among the natural substances with promising biological, therapeutic, and industrial value. In recent years, due to the broad spectrum of their biological potentials, triterpenes have been the subject of an intensive number of research works, which mainly have focused on their biopharmaceutical development. Indeed, triterpenes and their structural analogues display various biological effects such as hemolytic, hypocholesterolimic, immunostimulant, anti-inflammatory, antimicrobial, antiparasitic, cytotoxic, and anti-ulcer [12-18]. Moreover, triterpenes are known for their many important antiviral activities such as anti-hepatitis B virus activity, anti-HIV1 and 2, AIDS, anti-hepatitis C virus activity, and anti-Herpes simplex virus activity (FIG. 1) [11,19].

There is a great need to quickly develop and verify efficacy and safety of therapeutic treatment for viral infection from SARS-CoV-2 as well as its quickly spreading new variants. Further, there is a need for diversifying new SARS-CoV-2 treatment options and more specifically to new targets by using safer therapeutic compounds (e.g., compounds derived from natural sources) in the most cost effective and safety-oriented manner.

SUMMARY OF THE INVENTION

An aspect of the disclosure provides a method of treating coronavirus infection in a subject in need thereof, comprising the step of administering a coronavirus therapeutic composition to the subject in an amount sufficient to treat the infection. In some embodiments, the method includes the step of administering SARS-CoV-2 therapeutic composition comprising at least one triterpenoid selected from the group of triterpenoids 3-17 or combinations thereof. In some embodiments, the triterpenoids 3-17 are oleanolic acid and/or maslinic acid derivatives, wherein the triterpenoid 3 has the chemical structure of Formula III;

Formula III wherein the triterpenoid 4 has the chemical structure of Formula IV;

Formula IV wherein the triterpenoid 5 has the chemical structure of Formula V;

wherein the triterpenoid 6 has the chemical structure of Formula VI;

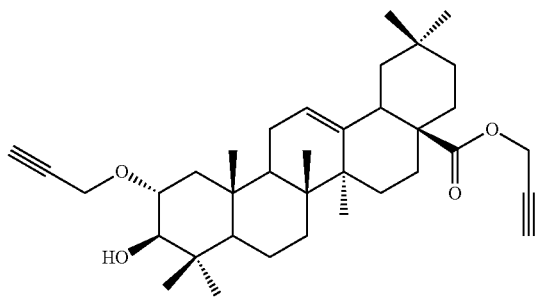

wherein the triterpenoid 7 has the chemical structure of Formula VII;

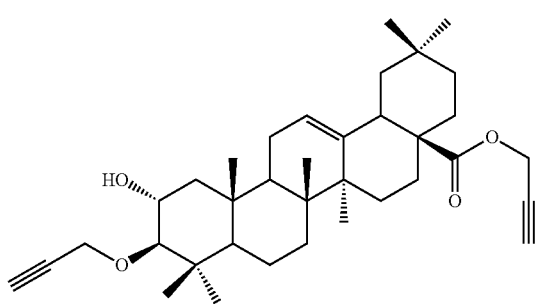

wherein the triterpenoid 8 has the chemical structure of Formula VIII;

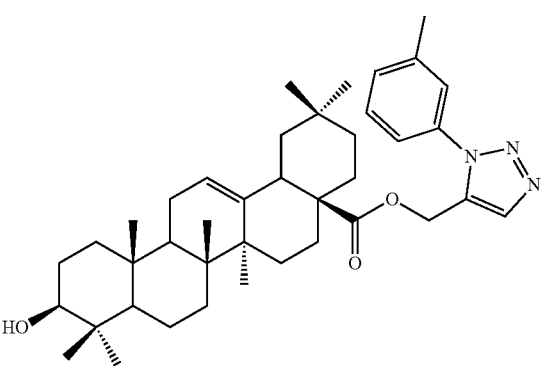

wherein the triterpenoid 9 has the chemical structure of Formula IX;

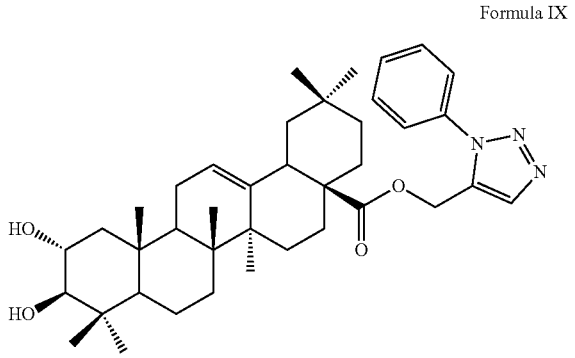

wherein the triterpenoid 10 has the chemical structure of Formula X;

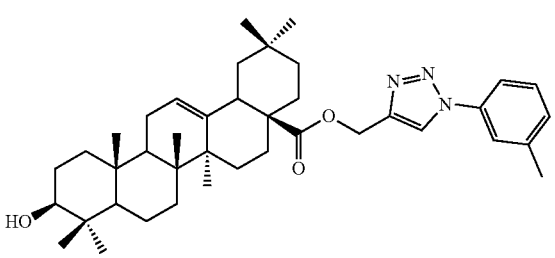

wherein the triterpenoid 11 has the chemical structure of Formula XI;

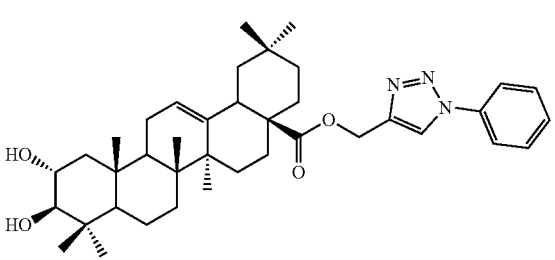

wherein the triterpenoid 12 has the chemical structure of Formula XII;

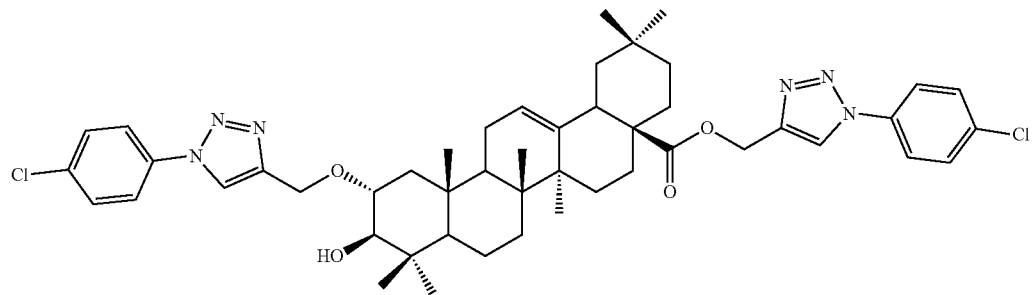
Formula XII
wherein the triterpenoid 13 has the chemical structure of Formula XIII;
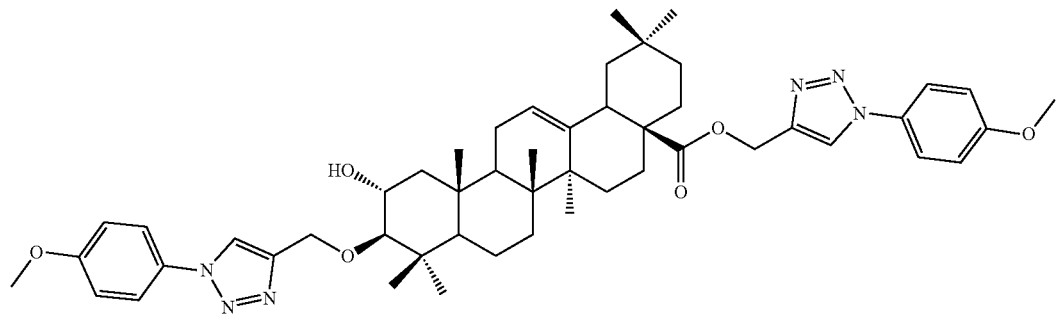
Formula XIII
wherein the triterpenoid 14 has the chemical structure of Formula XIV;
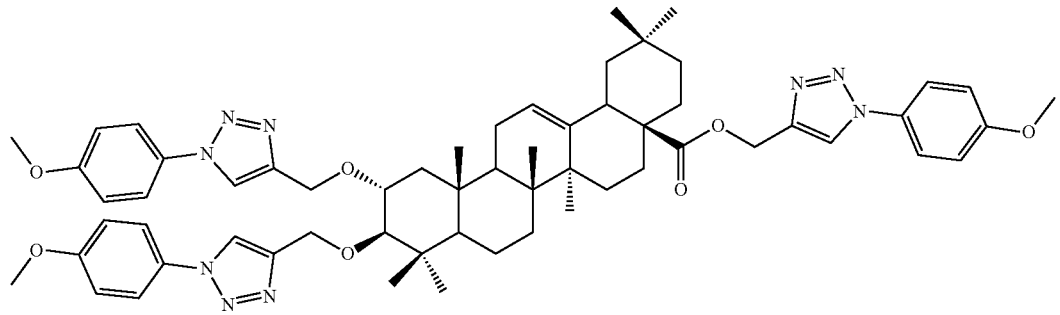
Formula XIV
wherein the triterpenoid 15 has the chemical structure of Formula XV;
wherein the triterpenoid 16 has the chemical structure of Formula XVI;
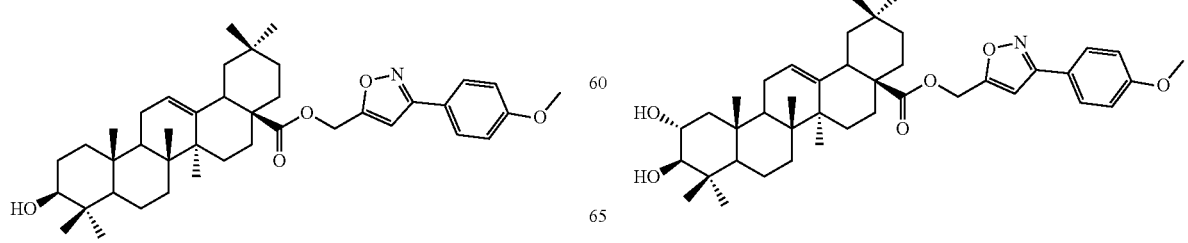
Formula XV
Formula XVI wherein the triterpenoid 17 has the chemical structure of Formula XVII.

Formula XVII

Another aspect of the disclosure provides a method of inhibiting coronavirus growth, comprising: contacting coronavirus particles with a composition comprising a compound selected from the group consisting of triterpenoids 3-17 or combinations thereof, wherein the compound is used in an amount sufficient to inhibit the coronavirus growth. In some embodiments, the composition comprises a compound that is capable of interacting and forming a hydrogen bond with at least one amino acid of SARS-CoV-2 main protease to suppress anti-viral activities of the SARS-CoV-2 main protease. In some embodiments, the amount sufficient to inhibit the coronavirus growth is a concentration of the compound to partially or completely inhibit a proteolytic activity of SARS-CoV-2 main protease. In some embodiments, the triterpenoids 3-17 are oleanolic acid and/or maslinic acid derivatives, wherein the triterpenoid 3 has the chemical structure of Formula III;

Formula III wherein the triterpenoid 4 has the chemical structure of Formula IV;

Formula IV wherein the triterpenoid 5 has the chemical structure of Formula V;

Formula V wherein the triterpenoid 6 has the chemical structure of Formula VI;

Formula VI wherein the triterpenoid 7 has the chemical structure of Formula VII;

Formula VII wherein the triterpenoid 8 has the chemical structure of Formula VIII;

Formula VIII

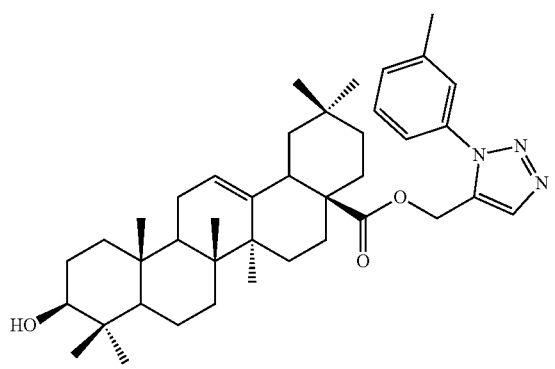

wherein the triterpenoid 9 has the chemical structure of Formula IX;

Formula IX

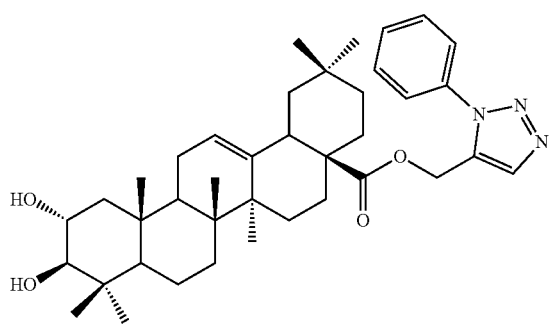

wherein the triterpenoid 10 has the chemical structure of Formula X;

Formula X

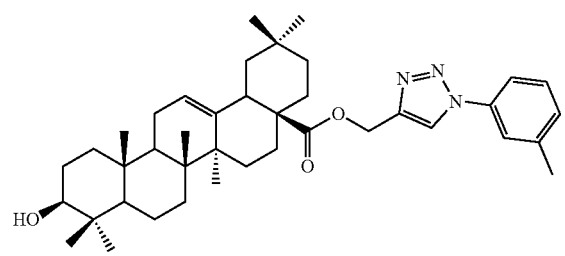

wherein the triterpenoid 11 has the chemical structure of Formula XI;

Formula XI

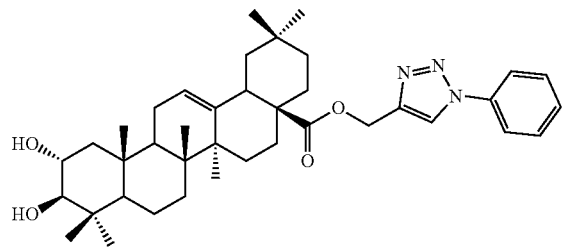

wherein the triterpenoid 12 has the chemical structure of Formula XII;

Formula XII

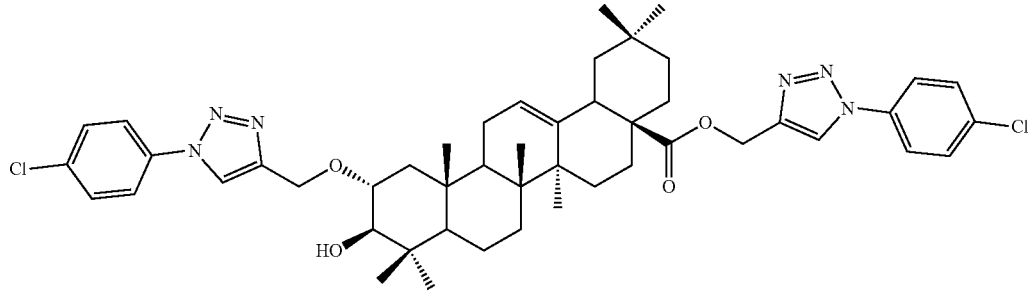

wherein the triterpenoid 13 has the chemical structure of Formula XIII;

Formula XIII

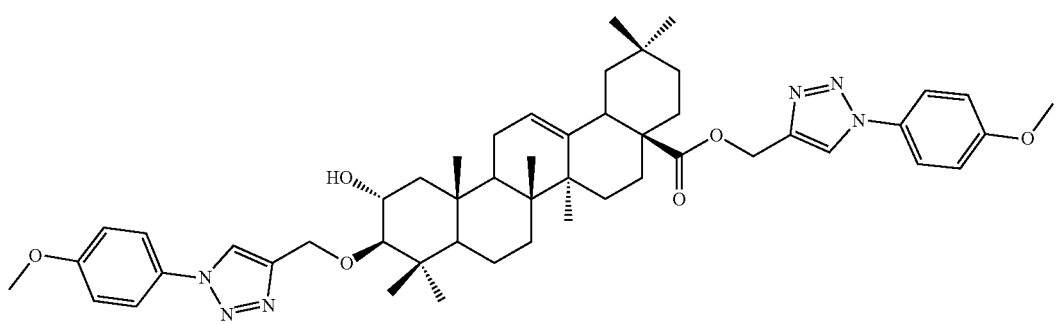

wherein the triterpenoid 14 has the chemical structure of Formula XIV;

Formula XIV wherein the triterpenoid 15 has the chemical structure of Formula XV;

Formula XV wherein the triterpenoid 16 has the chemical structure of Formula XVI;

Formula XVI wherein the triterpenoid 17 has the chemical structure of Formula XVII.

Formula XVII

Additional features and advantages of the present invention will be set forth in the description of disclosure that follows, and in part will be apparent from the description of may be learned by practice of the disclosure. The disclosure will be realized and attained by the compositions and methods particularly pointed out in the written description and claims hereof.

DETAILED DESCRIPTION

Figure 1:
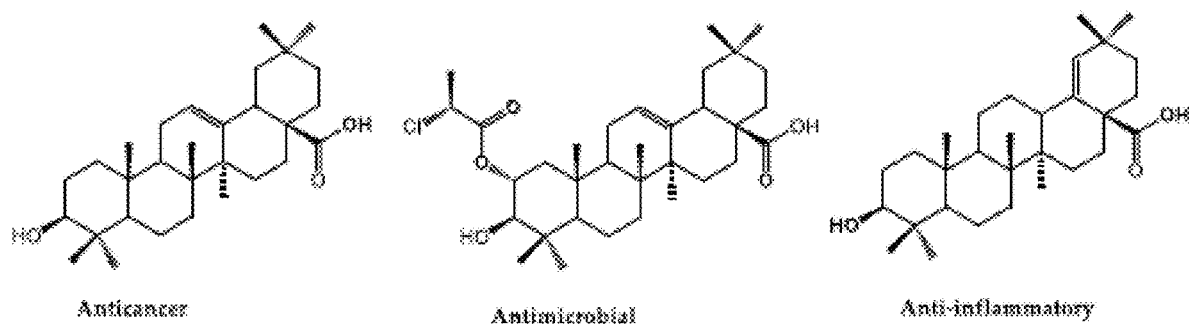
FIG. 1 shows chemical structures of exemplary bioactive triterpenes.
Figure 2:
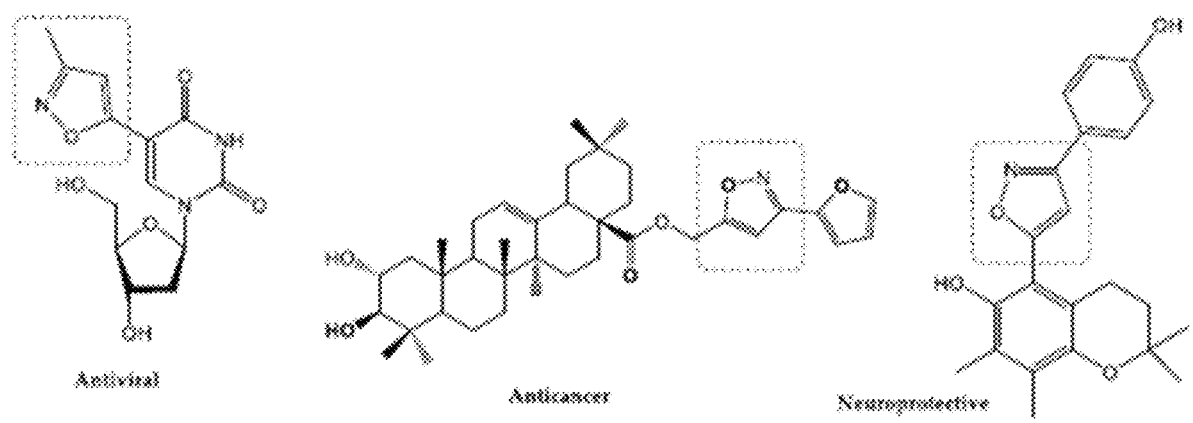
FIG. 2 shows chemical structures of exemplary bioactive isoxazoles.
Figure 3:
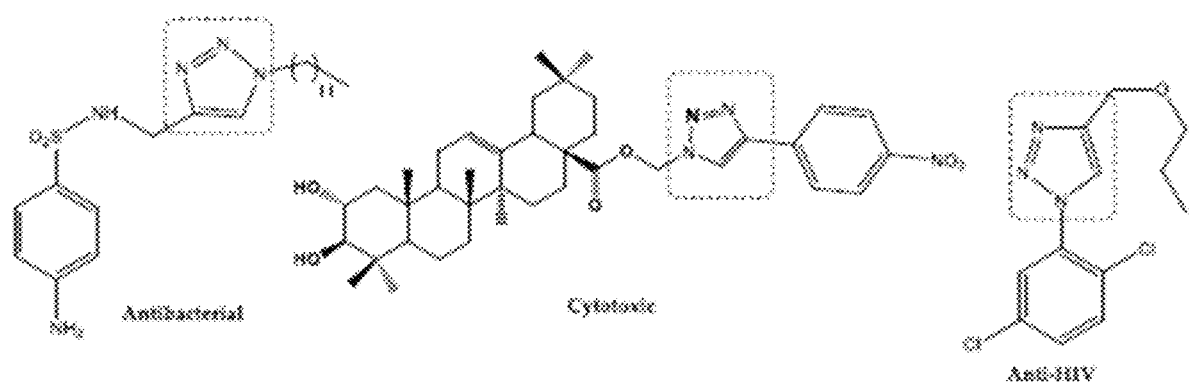
FIG. 3 shows chemical structures of exemplary bioactive triazoles.

The preferred embodiments of the present disclosure are directed toward a method of using triterpenoids for treating coronavirus infection. The method also includes using propargyl-group containing oleanolic acid derivatives for treating SARS-CoV-2 infection. The antiviral property of each compound is based on the ability to impair the viral replication of SARS-CoV-2 by disturbing a viral function of SARS-CoV-2 main protease.

In some embodiments, a method of treating coronavirus comprises the step of administering a coronavirus therapeutic composition to a subject an amount sufficient to treat the infection. In some embodiments, the method includes the step of administering SARS-CoV-2 therapeutic composition comprising at least one triterpenoid selected from the group of triterpenoids 3-17 or combinations thereof. In some embodiments, the triterpenoids 3-17 are chemical derivatives of oleanolic acid and/or maslinic acid or pharmacologically acceptable salts thereof, wherein the triterpenoid 3 has the chemical structure of Formula III;

Formula III wherein the triterpenoid 4 has the chemical structure of Formula IV;

Formula IV wherein the triterpenoid 5 has the chemical structure of Formula V;

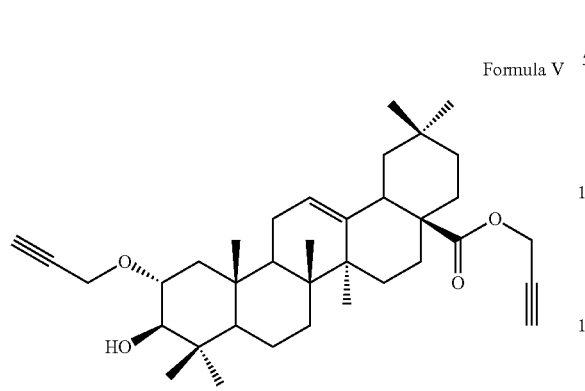

Formula V wherein the triterpenoid 6 has the chemical structure of Formula VI;

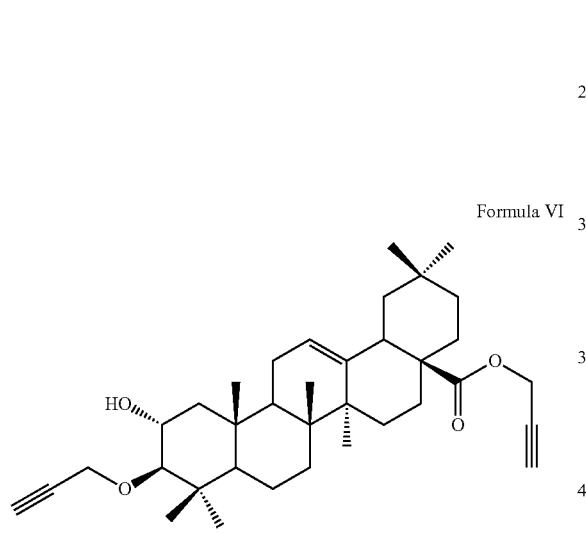

Formula VI wherein the triterpenoid 7 has the chemical structure of Formula VII;

Formula VII

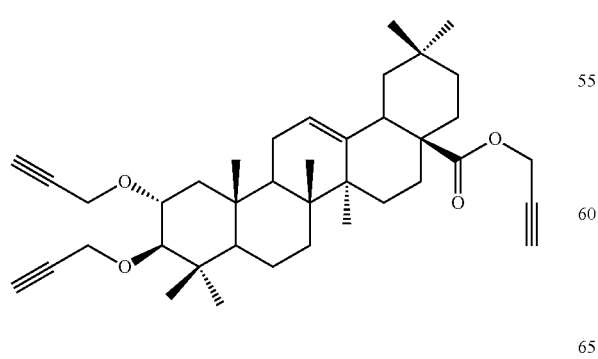

wherein the triterpenoid 8 has the chemical structure of Formula VIII;

Formula VIII

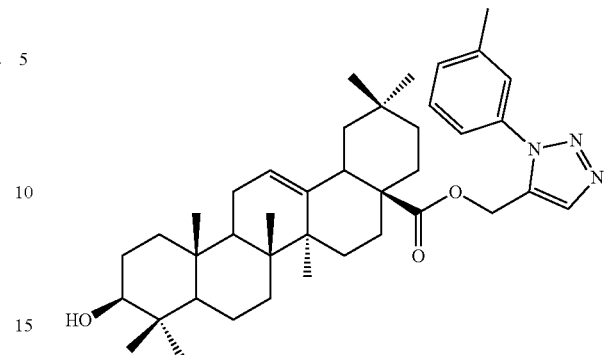

wherein the triterpenoid 9 has the chemical structure of Formula IX;

Formula IX

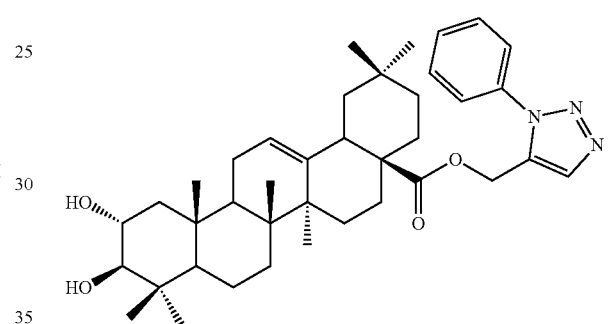

wherein the triterpenoid 10 has the chemical structure of Formula X;

Formula X

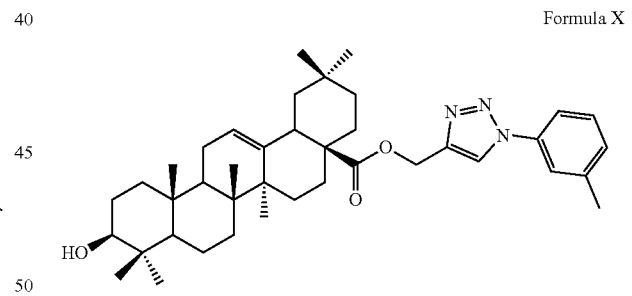

wherein the triterpenoid 11 has the chemical structure of Formula XI;

Formula XI wherein the triterpenoid 12 has the chemical structure of Formula XII;

Formula XII

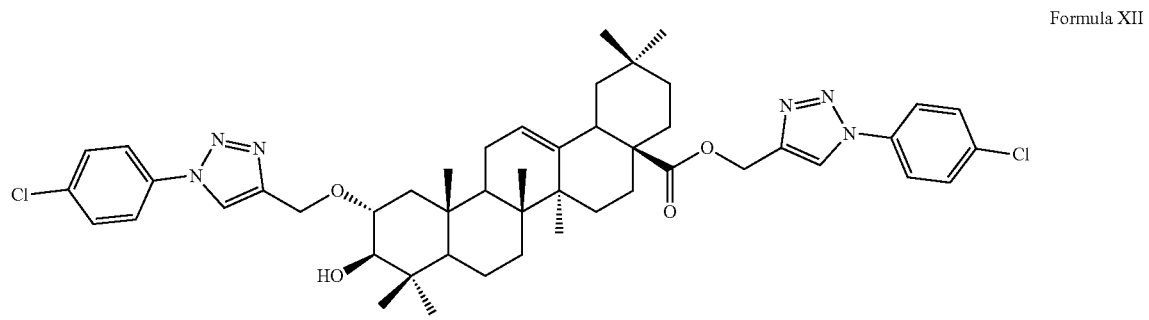

wherein the triterpenoid 13 has the chemical structure of Formula XIII;

Formula XIII

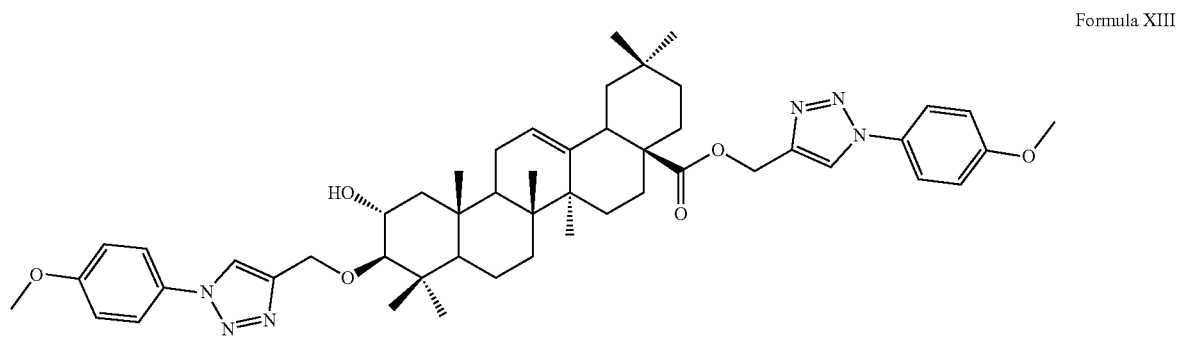

wherein the triterpenoid 14 has the chemical structure of Formula XIV;

Formua XIV

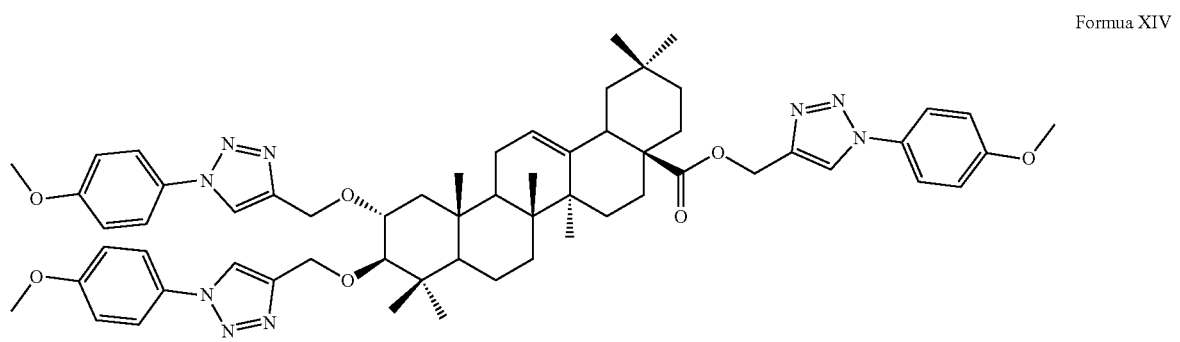

wherein the triterpenoid 15 has the chemical structure of Formula XV;

wherein the triterpenoid 16 has the chemical structure of Formula XVI;

Formula XV

Formula XVI

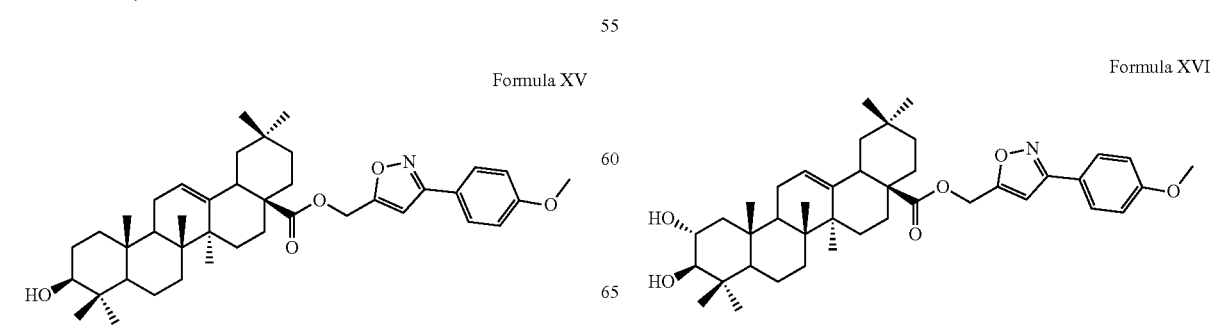

wherein the triterpenoid 17 has the chemical structure of Formula XVII.

Formula XVII

As used herein, the term "severe acute respiratory syndrome coronavirus 2 (SARS-CoV-2)" refers to virus comprising a virion with 50-200 nanometers in diameter and a genomic size of about 30 kilobases, encoding multiple structural proteins, such as the S (spike), E (envelope), M (membrane) and N (nucleocapsid), and non-structural proteins. Coronaviruses are a group of related RNA viruses that cause diseases in mammals and birds. In humans and birds, they cause respiratory tract infections that can range from mild to lethal. Mild illnesses in humans include some cases of the common cold (which is also caused by other viruses, predominantly rhinoviruses), while more lethal varieties can cause SARS, MERS, and COVID-19. Coronaviruses constitute the subfamily Orthocoronavirinae, in the family Coronaviridae, order Nidovirales, and realm Riboviria. Coronaviruses have four genera: alpha-, beta-, gamma-, and delta-coronaviruses. They are enveloped viruses with a positive-sense single-stranded RNA genome and a nucleocapsid of helical symmetry. The genome size of coronaviruses ranges from approximately 26 to 32 kilobases. Exemplary coronaviruses that may be treated with the compositions of the disclosure include, but are not limited to, SARS-Cov, SARS-Cov-2, MERS-Cov, HCoV-OC43, HCoV-HKU1, HCoV-229E, and HCoV-NL63.

The term, "main protease" or "SARS-CoV-2 main protease" refers to $M^{pro}$ (also referred to as $3CL^{pro}$) which is a SARS-CoV-2 specific protease and dissimilar to human proteases. $M^{pro}$ has a critical role of cleaving and processing two overlapping polyproteins (pp1a, pp1ab) that are cleaved into 16 non-structural proteins (nsp1-16).

In preferred embodiment, the triterpenoid compounds of the SARS-CoV-2 therapeutic composition are derivatives of oleanolic acid (OA) and/or maslinic acid (MA). The term "derivative" or "chemical derivative" is used with reference to a first compound (e.g. OA or MA) and indicates a second compound that is structurally related to the first compound for being derivable from the first compound by a modification that introduces a feature that is not present in the first compound while retaining functional properties of the first compound. Accordingly, a derivative compound of OA and/or MA, usually differs from the original compound by modification of the chemical formula that might or might not be associated with an additional function not present in the original compound. A derivative compound of OA and/or MA retains however one or more functional activities that are herein described in connection with compound in association with the ability of OA and/or MA to interfere the function of SARS-CoV-2 main protease.

Accordingly, in various cases, based on the predicted binding site of the triterpenoid compounds, a core structure for a derivative can be defined as the part that interacts with the SARS-CoV-2 main protease and hence shouldn't be modified. This will vary for each different ligand. The nature and efficacy of each derivative are discussed in Example 1-3.

In some embodiments, a method of inhibiting coronavirus growth, comprising: contacting coronavirus particles with a composition comprising a compound selected from the group consisting of triterpenoids 3-17 or combinations thereof, wherein the compound is used in an amount sufficient to inhibit the coronavirus growth is provided. In some embodiments, the composition comprises a compound that is capable of interacting and forming a hydrogen bond with at least one amino acid of the SARS-CoV-2 main protease to suppress anti-viral activities of the interacting protease. In these embodiments, the amount sufficient to inhibit the coronavirus growth is a concentration of the compound to partially or completely inhibit a proteolytic activity of SARS-CoV-2 main protease. In preferred embodiments, the triterpenoids 3-17 are derivatives of oleanolic acid and/or maslinic acid or pharmacologically acceptable salts thereof, wherein the triterpenoid 3 has the chemical structure of Formula III;

Formula III wherein the triterpenoid 4 has the chemical structure of Formula IV;

Formula IV wherein the triterpenoid 5 has the chemical structure of Formula V;

Formula V

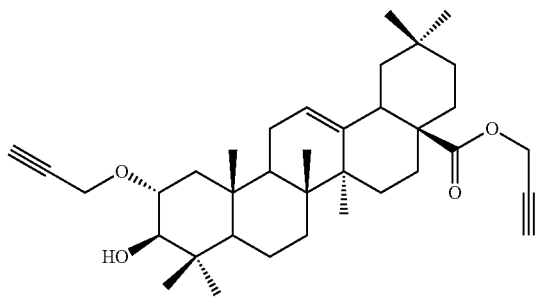

wherein the triterpenoid 6 has the chemical structure of Formula VI;

Formula VI

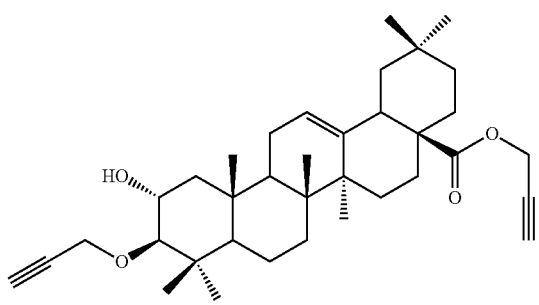

wherein the triterpenoid 7 has the chemical structure of Formula VII;

Formula VII

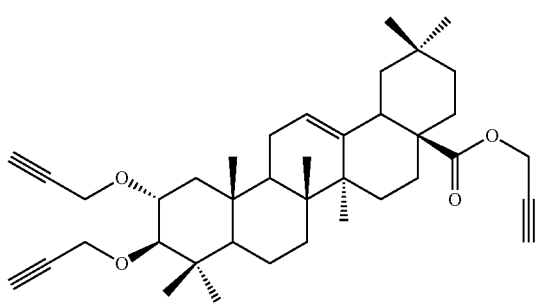

wherein the triterpenoid 8 has the chemical structure of Formula VIII;

Formula VIII

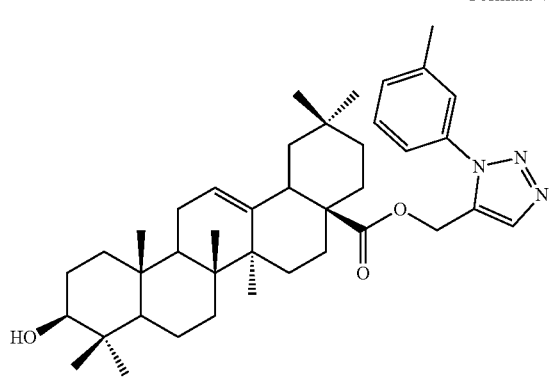

wherein the triterpenoid 9 has the chemical structure of Formula IX;

Formula IX

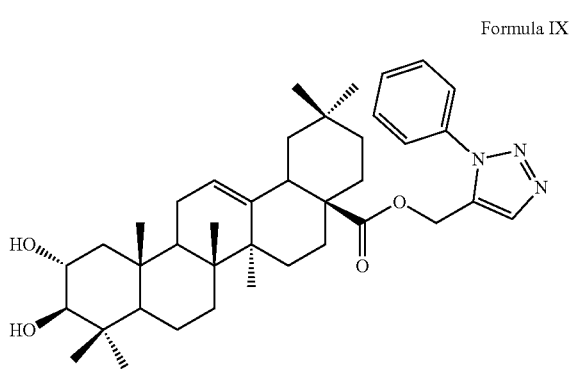

wherein the triterpenoid 10 has the chemical structure of Formula X;

Formula X

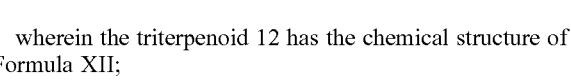

wherein the triterpenoid 11 has the chemical structure of Formula XI;

Formula XI wherein the triterpenoid 12 has the chemical structure of Formula XII;

Formula XII
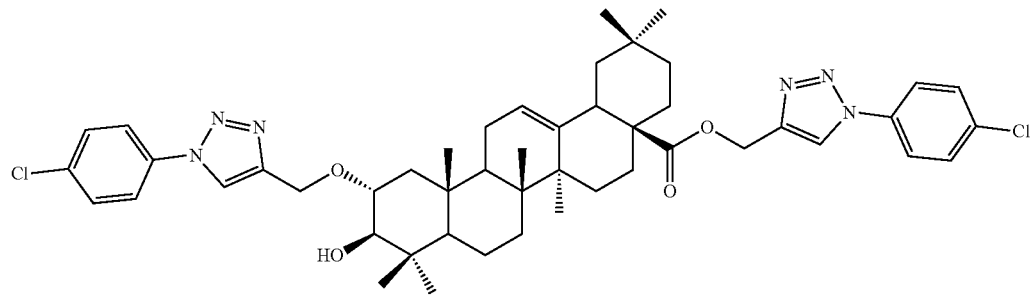
wherein the triterpenoid 13 has the chemical structure of Formula XIII;
Formula XIII
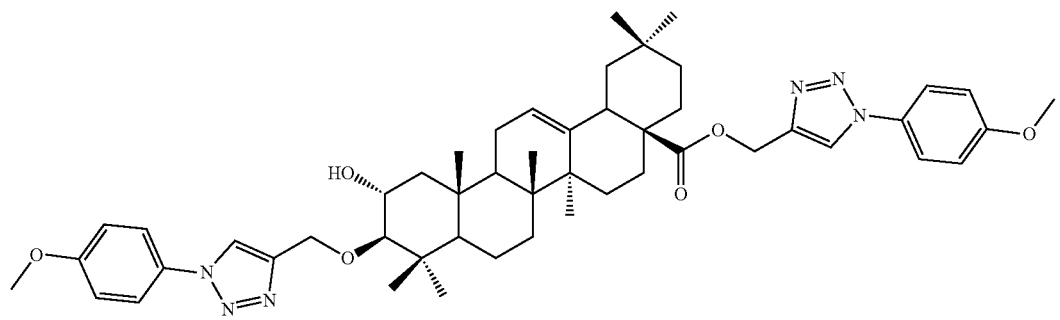
wherein the triterpenoid 14 has the chemical structure of Formula XIV;
Formula XIV
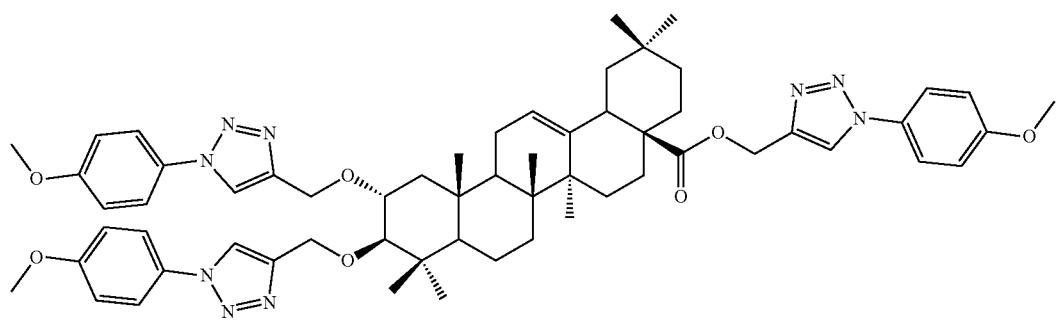
wherein the triterpenoid 15 has the chemical structure of Formula XV;
wherein the triterpenoid 16 has the chemical structure of Formula XVI;
Formula XV
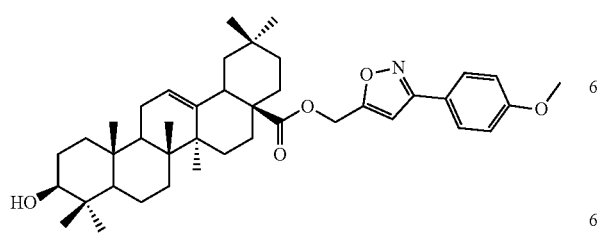
Formula XVI
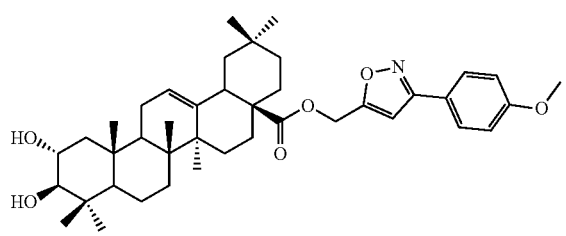

wherein the triterpenoid 17 has the chemical structure of Formula XVII.

Formula XVII

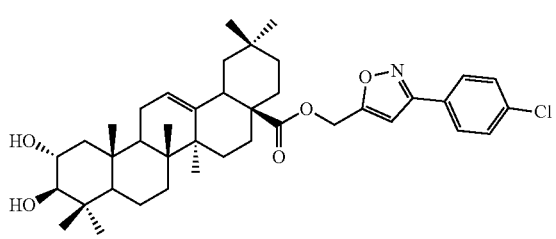

In some embodiments, an effective amount or amount sufficient for treatment of a composition comprising one or more triterpenoid compounds is administered to a subject in need thereof. An effective or sufficient amount is the amount that results in a concentration of a ligand at a cellular level that allows compound binding to the target protease binding site resulting in disturbance of the viral function of the SARS-CoV-2 main protease. In some embodiments, for example, an effective amount comprises a concentration of one or more triterpenoids 3-17 from about 1 micromolar to about 1.25 millimolar. Additional amounts known or expected to be effective for triterpenoids 3-17 herein described comprise from about 0.5 uM to about 1 uM, from about 1 uM to about 2.5 uM, from about 2.5 uM to about 5 uM, from about 5 uM to about 10 uM, from about 10 uM to about 100 uM, from about 100 uM to about 500 uM, from about 500 uM to about 1000 uM, from about 1 mM to about 1.25 mM, from about 1.25 mM to about 2.5 mM, from about 2.5 mM to about 5 mM, from about 5 mM to about 10 mM. Additional effective amounts known or expected to be effective comprise from about 1-2.5 uM, from about 2.6 uM to about 10 uM, from about 11 uM to about 100 uM; from about 101 uM to about 1000 uM; from about 1.25 mM to about 10 mM.

A medicament typically contains from about 0.01 mg to about 500.0 mg of the active ingredient, in particular from 1.0 mg to about 100.0 mg of the active ingredient. An effective amount of the drug is ordinarily supplied at a dosage level from 5 mg/kg to about 45 mg/kg of body weight per day, e.g. 10-40 mg/kg or 20-40 mg/kg.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

The compounds described herein are generally delivered (administered) as a pharmaceutical composition. Such pharmaceutical compositions generally comprise at least one of the disclosed compounds, i.e. one or more than one (a plurality) of different compounds (e.g. 2 or more such as 2, 3, 4, 5, 6, 7, 8, 9, 10 or more) may be included in a single formulation. Accordingly, the present invention encompasses such formulations/compositions. The compositions generally include one or more substantially purified compounds as described herein, and a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies, but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The oleanolic and/or maslinic acid derivatives may be administered in vivo by any suitable route including but not limited to: inoculation or injection (e.g. intravenous, intraperitoneal, intramuscular, subcutaneous, intra-aural, intraarticular, intramammary, and the like), topical application (e.g. on areas such as eyes, skin, in ears or on afflictions such as wounds and burns) and by absorption through epithelial or mucocutaneous linings (e.g., nasal, oral, vaginal, rectal, gastrointestinal mucosa, and the like). Other suitable means include but are not limited to: inhalation (e.g., The compounds described herein are generally delivered (administered) as a pharmaceutical composition. Such pharmaceutical compositions generally comprise at least one of the disclosed compounds, i.e. one or more than one (a plurality)

of different compounds (e.g. 2 or more such as 2, 3, 4, 5, 6, 7, 8, 9, 10 or more) may be included in a single formulation. Accordingly, the present invention encompasses such formulations/compositions. The compositions generally include one or more substantially purified compounds as described herein, and a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies, but is generally from about 1-99%. Still other suitable formulations for use in the present invention are found, for example in Remington's Pharmaceutical Sciences, 22nd ed. (2012; eds. Allen, Adejarem Desselle and Felton).

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like. The sterol liposome entrapped agent may be administered in vivo by any suitable route including but not limited to: inoculation or injection (e.g. intravenous, intraperitoneal, intramuscular, subcutaneous, intra-aural, intraarticular, intramammary, and the like), topical application (e.g. on areas such as eyes, skin, in ears or on afflictions such as wounds and burns) and by absorption through epithelial or mucocutaneous linings (e.g., nasal, oral, vaginal, rectal, gastrointestinal mucosa, and the like). Other suitable means include but are not limited to: inhalation (e.g. as a mist or spray), orally (e.g. as a pill, capsule, liquid, etc.), intravaginally, intranasally, rectally, by ingestion of a food or probiotic product containing the antimicrobial peptide, as eye drops, incorporated into dressings or bandages (e.g. lyophilized forms may be included directly in the dressing), etc. In preferred embodiments, the mode of administration is topical or oral or by injection. In addition, the compositions may be administered in conjunction with other treatment modalities such as substances that boost the immune system, various chemotherapeutic agents, other antibiotic agents, and the like.

The following descriptions and examples illustrate some exemplary embodiments of the disclosed invention in detail. Those of the skill in the art will recognize that there are numerous variations and modifications of this invention that are encompassed by its scope. Accordingly, the description of a certain exemplary embodiment should not be deemed to limit the scope of the present invention.

Example 1

Respiratory viruses represent a major public health concern, as they are highly mutated, resulting in the emergence of new strains with high pathogenicity. Currently, the whole world is suffering from a new evolving severe acute respiratory syndrome coronavirus 2 (SARS-CoV-2), which originated from the Hubei region, concisely in Wuhan City in early December 2019, and subsequently spread globally. Due to the increasing rate of SARS-CoV-2-infected confirmed cases associated with relatively high mortality rate, the WHO raised awareness and declared an emergency, claiming a potentially pandemic lethal infectious disease named COVID-19. Initially, SARS-CoV-2 was considered as a zoonotic disease, based on a high number of infected people exposed to a wet animal market in the Wuhan Chinese city; however, transmission from person to person was confirmed, making the situation even worse. This condition resulted in quarantines in many places worldwide, cancelling flights and suspending travel, with the consequence of huge economic burden. The perceived threat of this pandemic has led many researchers and academic institutions all over the world to dissect COVID-19 from different perspectives, including but not limited to the route of virus transmission, diagnosis, virus inhibition treatments, and vaccine preparation. Apparently, no complete treatment option for patients with severe symptoms has been discovered. To date, two monoclonal antibody treatments (bamlanivimab and a combination of casirivimab and imdevimab) for emergency use for non-hospitalized adults with mild to moderate COVID-19 symptoms have been approved by the FDA. Special consideration for more susceptible people such as elderly people, patients with chronic diseases, and health care takers should be applied. This study is considered as a serious attempt to synthesize a unique series of (1) oleanolic acid and (2) maslinic acid derivatives as anti-SARS-CoV-2 candidates.

Green Chemistry Extraction of Compounds 1 and 2

The ultrasound-assisted extraction of triterpenoids 1 and 2 from pomace olive of Olea europaea L. was optimized compared to previous methods used. The triterpenoid yield was 3.6 and 9.2 mg/g dry weight (DW), respectively, under optimal conditions. As shown in Table 1, the present study is the first report on the simultaneous extraction of triterpenoids 1 and 2 from pomace olive (Olea europaea L.) cultivar: Chemlali with a large amount under green chemistry conditions (ultrasonic-assisted extractions followed by centrifugation and purification), compared with those of previous works. This developed process could be useful in the preparation of a triterpenoid-rich ingredient that holds great promise for application in the therapeutic industry.

TABLE 1

Methods and extraction yield of oleanolic acid and maslinic acid from different pomace olive cultivars.

| Cultivar | Extraction Methods | Oleanolic acid (mg/g DW) | Maslinic acid (mg/g DW) |
| --- | --- | --- | --- |
| Picual | Solid-liquid extraction (maceration) | 0.500 | 1.200 |
| Hojiblanca | Solid-liquid extraction (maceration) | 0.500 | 1.300 |
| Arbequina | Solid-liquid extraction (maceration) | 0.400 | 1.500 |
| Non-indicated | Solid-liquid extraction (maceration) | 0.015 | 0.034 |
| Manzanilla | Solid-liquid extraction (maceration) | 0.274 | 0.824 |
| Hojiblanca | Solid-liquid extraction (centrifugation) | 0.565 | 0.904 |
| Cacerena | Solid-liquid extraction (centrifugation) | 0.185 | 0.295 |
| Kalamata | Solid-liquid extraction (centrifugation) | 0.841 | 1.318 |
| Picual | Ultrasonic-assisted extraction | 1.003 | 2.440 |
| Kalamon | Ultrasonic-assisted extraction | 0.838 | 2.100 |
| Chemlali | Solid-liquid, then ultrasonic-assisted extractions | 3.400 | 8.500 |
| Chemlali | Ultrasonic-assisted extractions, then centrifugation isolation | 3.6 | 9.2 |

Synthesis of Propargylated Triterpene Derivatives

Figure 4:
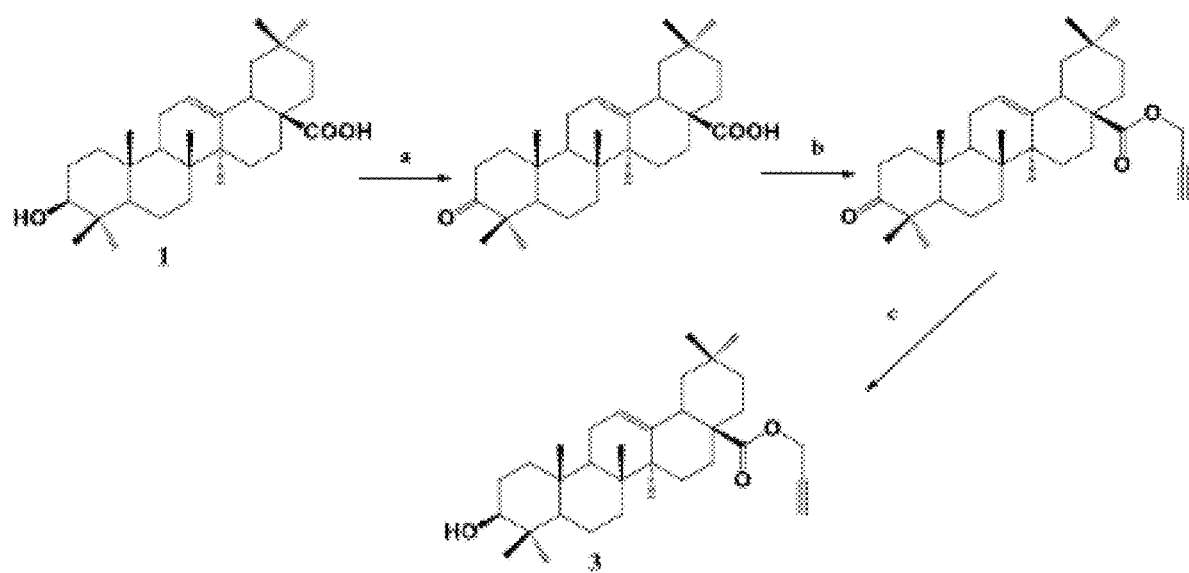
FIG. 4 shows a reaction scheme of oleanolic acid propargylation (1) with reagents and under the reaction conditions of (a) Jones oxidation ($CrO_3$, $H_2SO_4$/acetone), 0° C., (b) propargyl bromide, NaH, dry DMF, rt and (c) $NaBH_4$, CH3OH/THF, Microwave (250 W, 3 min).

To prepare the propargylated ester 3, derived from oleanolic acid 1, we started by the protection of the hydroxyl group at C-3 via its oxidation in order to direct the propargylation towards the carboxylic acid function in C-17 (FIG. 4). Then, we subjected the oxidized intermediate to the propargylation in dry N,N-Dimethylformamide (DMF) at room temperature in the presence of NaH and propargyl bromide for 2 h, yielding the desired propargylated intermediate which was reduced with sodium borohydride under microwave irradiation, to obtain the propargyl-(3β)-3-hydroxyolean-12-en-28-oate (compound 3). Similarly, maslinic acid 2 was subjected to the same reaction of propargylation [16,17], without oxidation beforehand, yielding a mixture of differently propargylated compounds which were separated over silica gel column chromatography to afford compounds 4-7 (Table 2).

TABLE 2

Oleanolic acid, maslinic acid and their derivatives 3-17 screened for their anti- SARS-CoV-2 activity in addition to N3 (the co-crystallized native inhibitor of SARS-CoV-2).

| Code | Nomenclature | Chemical Structures | Yield (%) |
| --- | --- | --- | --- |
| 1 | Oleanic acid | 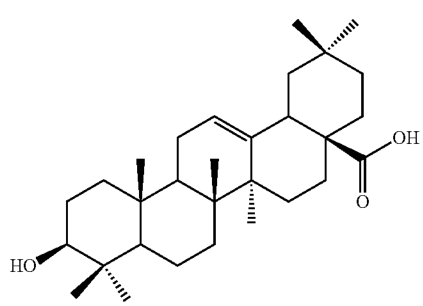 | — |

TABLE 2-continued

Oleanolic acid, maslinic acid and their derivatives 3-17 screened for their anti- SARS-CoV-2 activity in addition to N3 (the co-crystallized native inhibitor of SARS-CoV-2).

| Code | Nomenclature | Chemical Structures | Yield (%) |
|---|---|---|---|
| 2 | Maslinic acid | 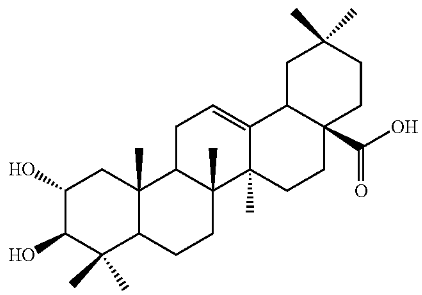 | — |
| 3 | Propargyl-(3β)-3-hydroxyolean-12-en-28-oate | 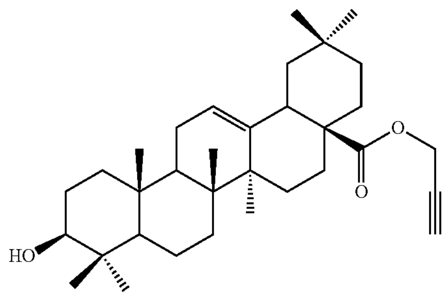 | 99 |
| 4 | Propargyl-(2α,3β)-2,3-dihydroxyolean-12-en-28-oate | 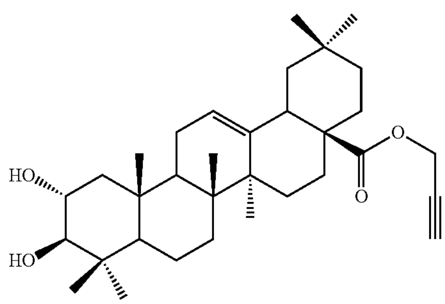 | 25 |
| 5 | Propargyl-(2α)-2-(propargyloxy)-(3β)-3-hydroxy-olean-12-en-28-oate | 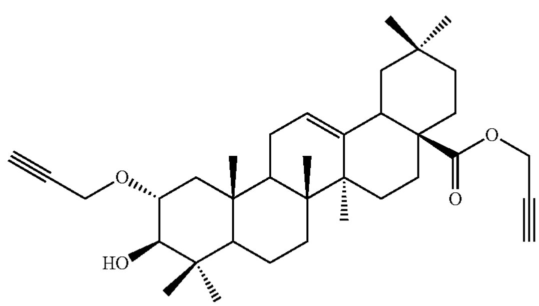 | 23 |
| 6 | Propargyl-(3α)-3-(propargyloxy)-(2β)-2-hydroxy-olean-12-en-28-oate | 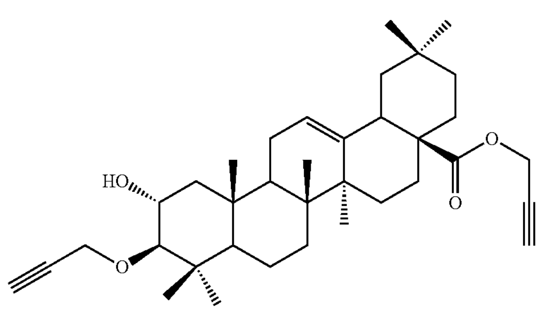 | 20 |

TABLE 2-continued

Oleanolic acid, maslinic acid and their derivatives 3-17 screened for their anti- SARS-CoV-2 activity in addition to N3 (the co-crystallized native inhibitor of SARS-CoV-2).

| Code | Nomenclature | Chemical Structures | Yield (%) |
|---|---|---|---|
| 7 | Propargyl-(2α,3β)-2,3-bis(propargyloxy)-olean-12-en-28-oate | 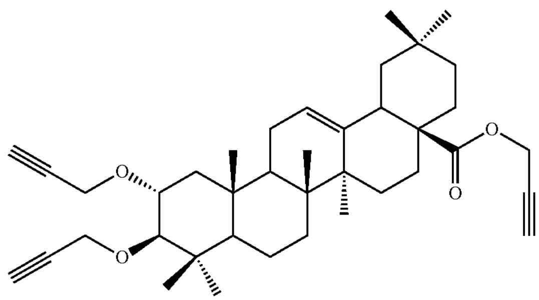 | 31 |
| 8 | (1-(3-methylphenyl)-1H-1,2,3-triazol-5-yl)methyl-(3β)-3-hydroxyolean-12-en-28-oate | 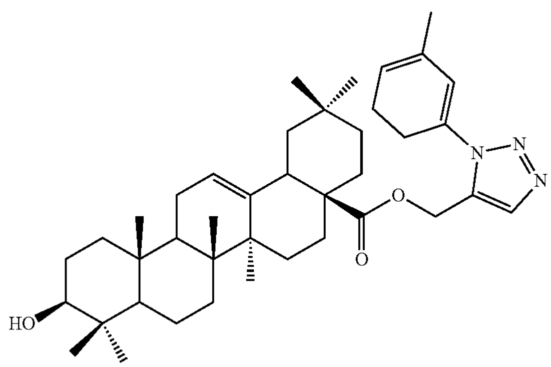 | 90 |
| 9 | (1-(3-methylphenyl)-1H-1,2,3-triazol-5-yl)methyl-(2α,3β)-2,3-dihydroxyolean-12-en-28-oate | 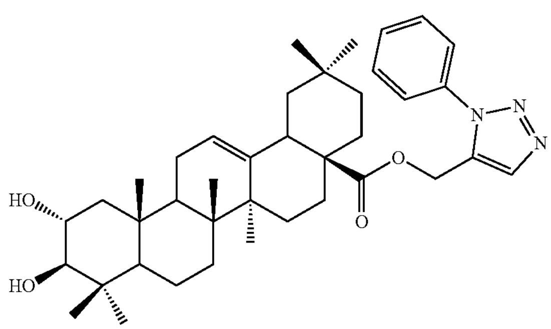 | 92 |
| 10 | (1-(3-methylphenyl)-1H-1,2,3-triazol-4-yl)methyl-(3β)-3-hydroxyolean-12-en-28-oate | 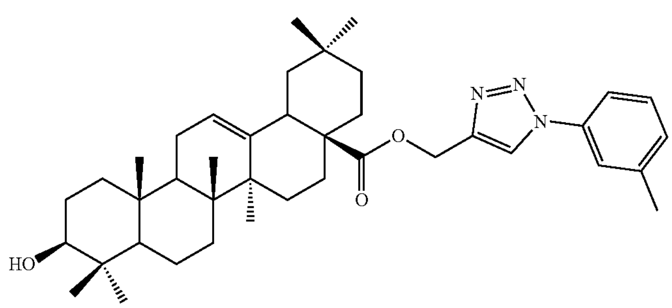 | 98 |

TABLE 2-continued

Oleanolic acid, maslinic acid and their derivatives 3-17 screened for their anti- SARS-CoV-2 activity in addition to N3 (the co-crystallized native inhibitor of SARS-CoV-2).

| Code | Nomenclature | Chemical Structures | Yield (%) |
|---|---|---|---|
| 11 | (1-Phenyl-1H-1,2,3-triazol-4-yl)methyl-(2α,3β)-2,3-dihydroxyolean-12-en-28-oate | 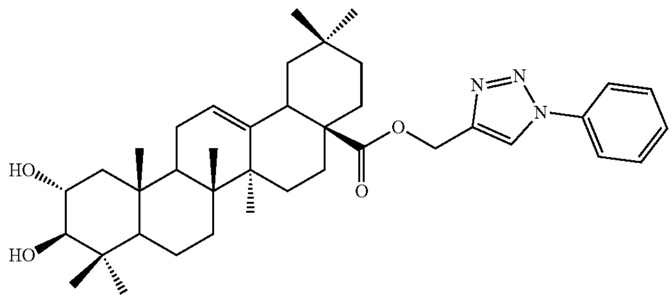 | 96 |
| 12 | (1-(4-Chlorophenyl)-1H-1,2,3-triazol-4-yl)methyl-(2α,3β)-2-((1-(4-chlorophenyl)-1H-1,2,3-triazol-4-yl)methoxy)-3-hydroxyolean-12-en-28-oate | 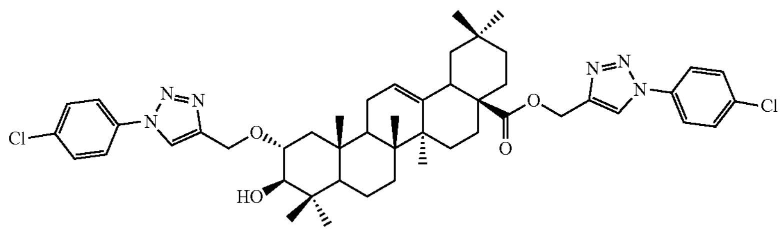 | 94 |
| 13 | (1-(4-Methoxyphenyl)-1H-1,2,3-triazol-4-yl)methyl-(2α,3β)-2-hydroxy-3-((1-(4-methoxyphenyl)-1H-1,2,3-triazol-4-yl)methoxy)-olean-12-en-28-oate | 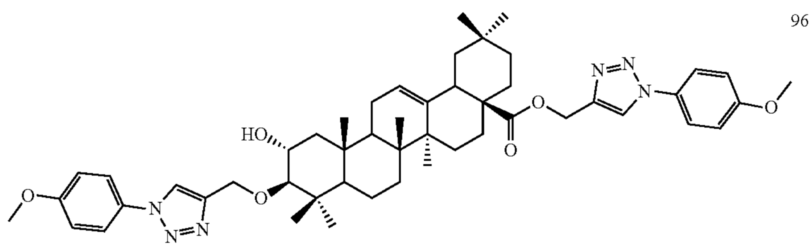 | 96 |
| 14 | (1-(4-Methoxyphenyl)-1H-1,2,3-triazol-4-yl)methyl-(2α,3β)-2,3-bis((1-(4-methoxyphenyl)-1H-1,2,3-triazol-4-yl)methoxy)-olean-12-en-28-oate | 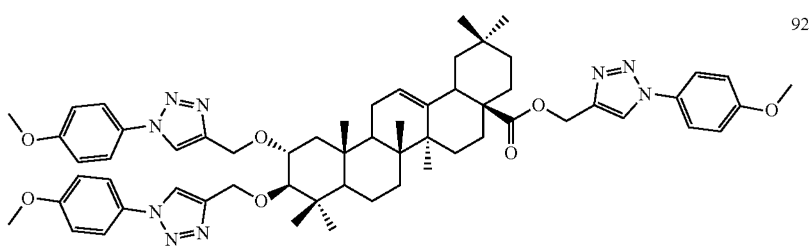 | 92 |
| 15 | (3-(4-methoxyphenyl)isoxazol-5-yl) methyl-(3β)-3-hydroxyolean-12-en-28-oate | 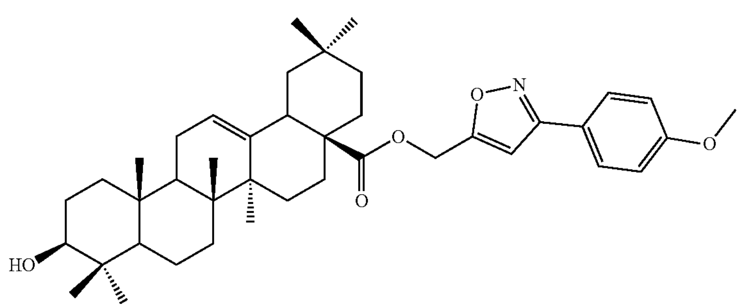 | 98 |

TABLE 2-continued

Oleanolic acid, maslinic acid and their derivatives 3-17 screened for their anti- SARS-CoV-2 activity in addition to N3 (the co-crystallized native inhibitor of SARS-CoV-2).

| Code | Nomenclature | Chemical Structures | Yield (%) |
|---|---|---|---|
| 16 | (3-(4-methoxyphenyl)isoxazol-5-yl) methyl-(2α,3β)-2,3-dihydroxyolean-12-en-28-oate | 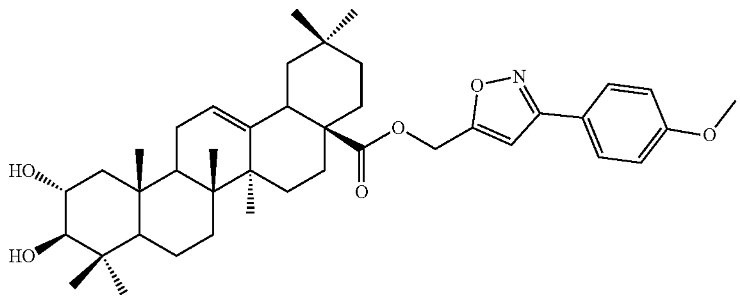 | 87 |
| 17 | (3-(4-chlorophenyl)isoxazol-5-yl) methyl-(2α,3β)-2,3-dihydroxyolean-12-en-28-oate | 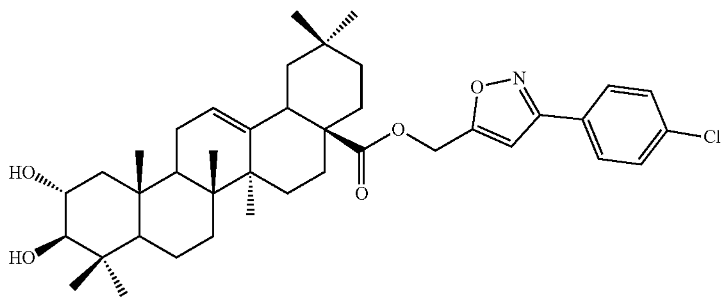 | 96 |
| 18 | N3 (co-crystallized native inhibitor of SARS-CoV-2) | 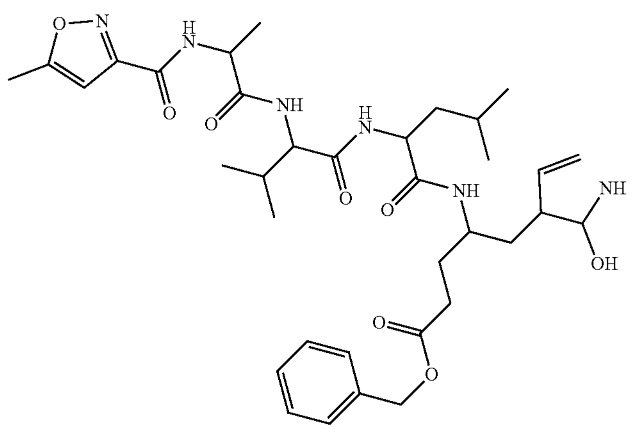 [SMILES: C=CC(CC(CCC(=O)OCc1ccccc1)NC(=O)C(CC(C)C)NC(=O)C(NC(=O)C(C)NC(=O)c1cc(C)on1)C(C)C)C(N)O] | — |

Figure 5A:
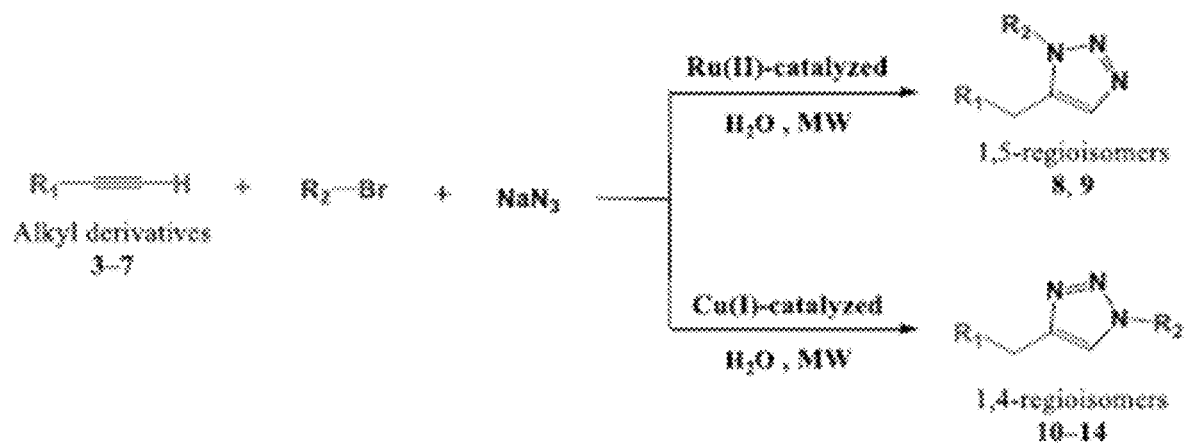
FIGS. 5A-B show reaction schemes of (A) synthesis of the 1,4- and 1,5-triazolyl derivatives (compounds 8-14 of the present disclosure) and (B) synthesis of the 3,5-disubstituted isoxazols (compounds 15-17 of the present disclosure).
Figure 5B:
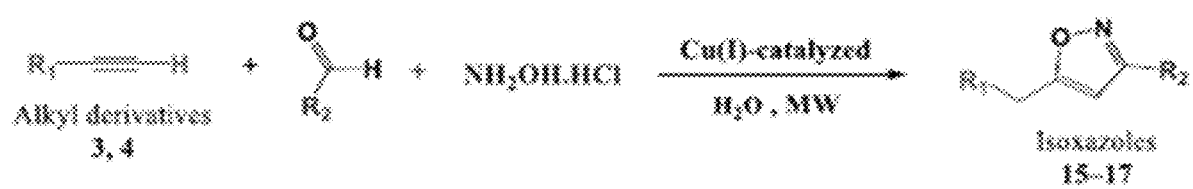

A regiospecific, facile and practical multicomponent synthesis of 1,5-triazolyl derivatives 8 and 9) by Ru(II)-catalyzed, and mono-, bis- and tri-1,4-triazolyl derivatives 10-14 by Cu(I)-catalyzed were carried out as shown in FIG. 5A. According to the same method as mentioned above, the dipolarophiles 3 and 4 were found to be readily cyclized to the 3,5-disubstituted isoxazoles 15-17 (Scheme 3). In fact, copper-catalyzed microwave-assisted multicomponent 1,3-dipolar cycloaddition between pentacyclic triterpenoid alkyne derivatives 3 and 4, and the appropriate aldehyde, regiospecifically afforded 3,5-disubstituted isoxazoles 15-17 in quantitative yields (Table 2). All the reactions were assisted by microwave irradiation avoiding toxic reagents and solvents. The products were obtained from the reaction mixture by simple purification in quantitative yields (Table 2). $^1$H NMR and $^{13}$C NMR spectra of the triterpenoid compounds 1-17 of the present disclosure are shown in FIGS. 12-28.

Molecular Docking of Compounds for Determining Anti-SARS-CoV-2 Activity

Figure 6:
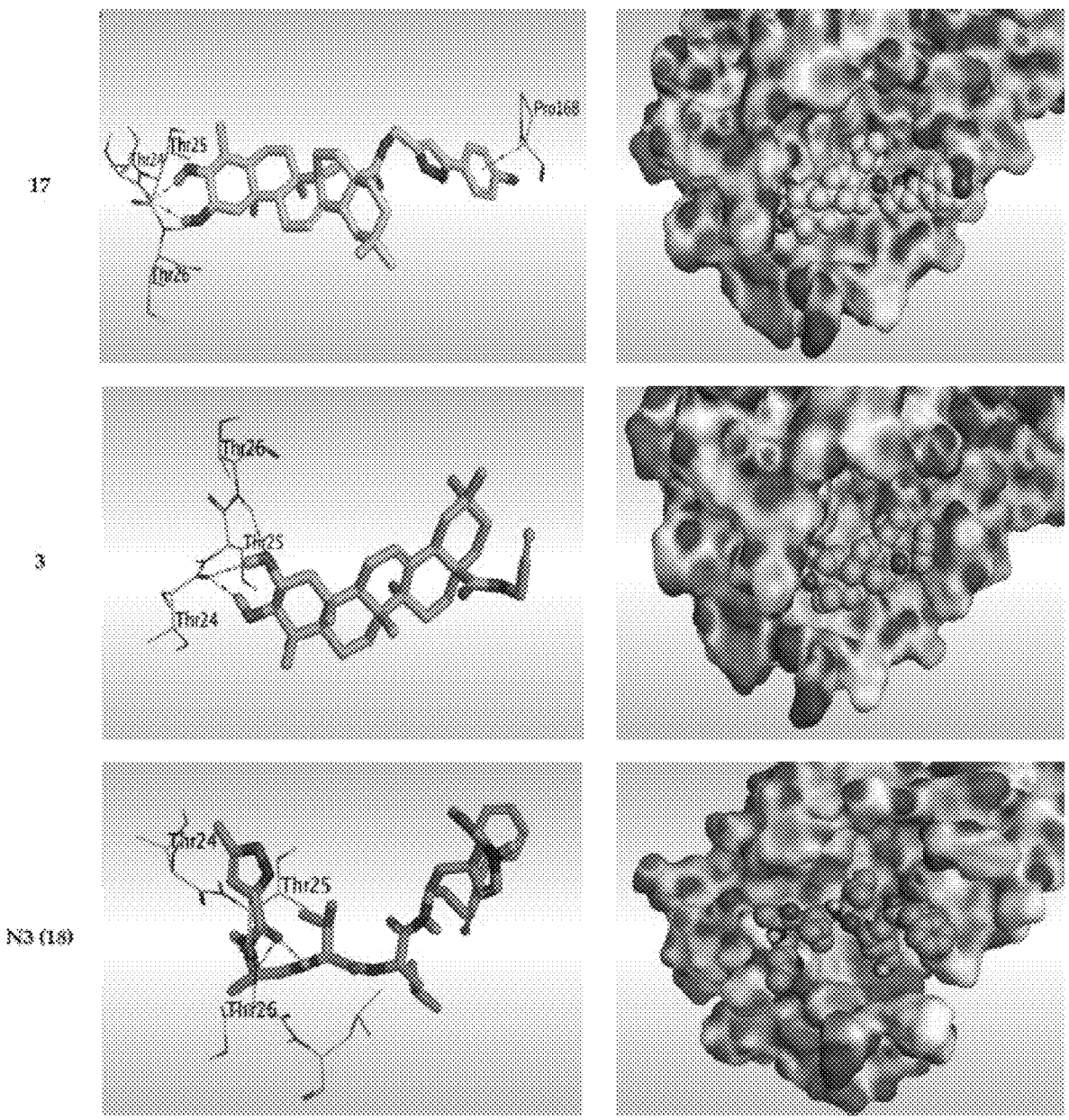
FIG. 6 shows 3D representations of the binding interactions and positioning between the two promising tested compounds (compounds 3 and 17 of the present disclosure) and the N3-binding pocket in comparison to the docked N3 inhibitor (compound 18 of the present disclosure).

By studying the binding pocket of the SARS-CoV-2Mpro, it was found that the cocrystallized native inhibitor (N3) fitted inside its binding pocket of the main protease receptor asymmetrically. N3 is a designed inhibitor for SARS-CoV-2 Mpro that was built from amino acids based on the Mpro pocket amino acids and cannot used medicinally (Table 2). Molecular docking of oleanolic acid 1, maslinic acid 2, and other oleanolic acid and maslinic acid derivatives 3-17 (Table 2), and N3 inhibitor 18 into the main protease binding site was performed. Almost all the tested compounds 1-17 were stabilized inside the Mpro binding site by variable scores and binding interactions with the amino acids of the receptor pocket. It is worth mentioning that, especially for both compounds 17 and 3, the obtained binding scores and modes were greatly similar to that of the docked N3 inhibitor 18, as depicted in FIG. 6. Additionally, the 2 D binding modes of the tested compounds 1-17 with the amino acids of the SARS-CoV-2 Mpro pocket are presented in FIGS. 30-38. All of the tested compounds 1-17 achieved promising binding scores (from −6.55 to −10.20 kcal/mol), compared to the docked co-crystallized N3 inhibitor 18 with a binding score of −9.70 kcal/mol. The RMSD refine values of the selected poses were within the acceptable range (from 0.9 to 2.25).

The docked N3 inhibitor 18 was stabilized inside the SARS-CoV-2 Mpro pocket through a hydrogen bond formation with Thr26 amino acid at 3.08 A°. Additionally, the most promising cytotoxic compound 17 fitted inside the binding site of the SARS-CoV-2 Mpro by three hydrogen bond formations, two of them with Thr24 at 2.71 and 3.19 A°, respectively, and the third one was formed with Thr26 at 3.28 A°. Moreover, compound 3 formed three hydrogen bonds with the previously mentioned two amino acids as well. The compound 3 formed two hydrogen bonds with Thr24 at 2.80 and 3.18 A°, respectively, and the third one with Thr26 at 3.37 A°. Additionally, it is worth mentioning that the achieved binding scores for compounds 17 and 3 were −8.00 and −7.55 kcal/mol, respectively, compared to the docked co-crystallized N3 inhibitor (18) (−9.70 kcal/mol) (Table 3).

By considering the docking findings of the selected tested compounds 1-17 against the binding pocket of the SARS-CoV-2 main protease compared to its co-crystallized inhibitor (N3) as a reference standard, and its great matching with the cytotoxicity studies applied, we can build a very promising and recommended idea about their mechanism of action.

Figure 7A:
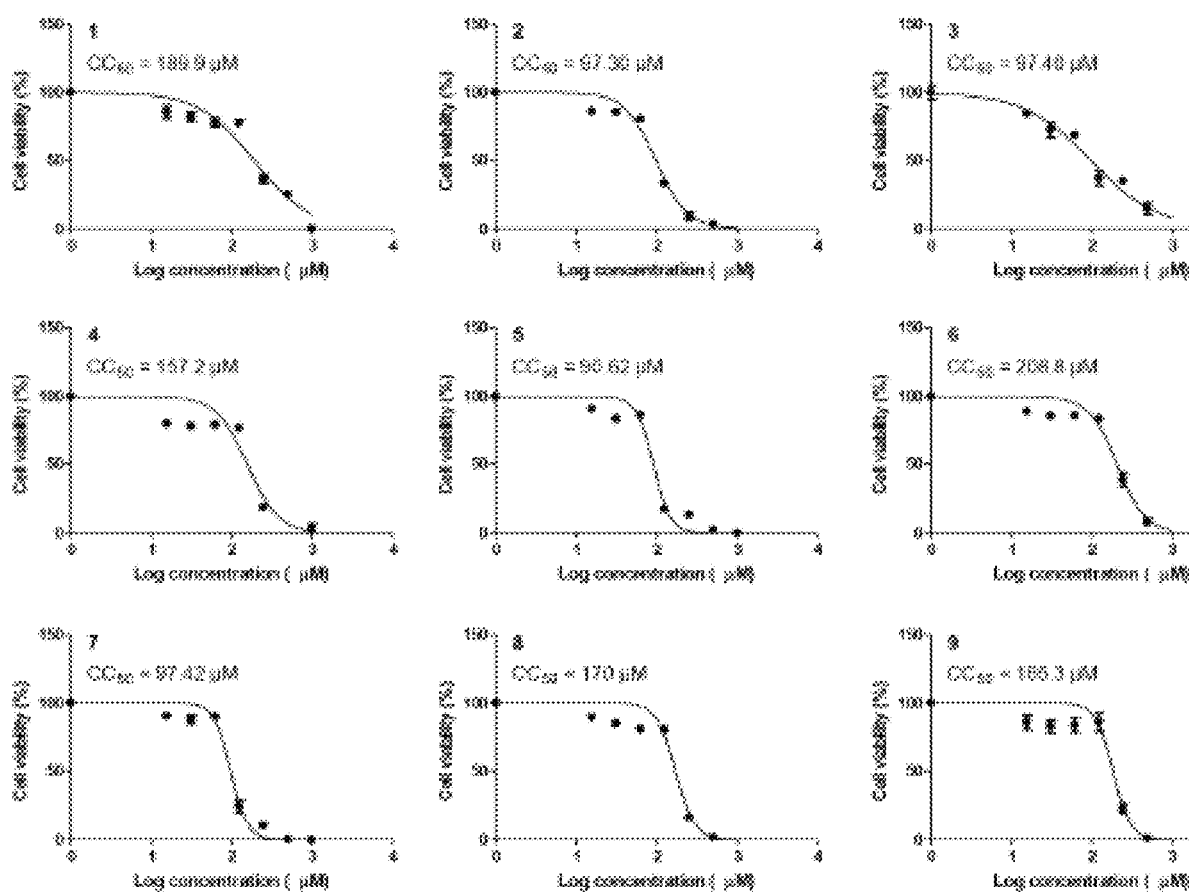
FIGS. 7A-B show (A) anti-SARS-CoV-2 activities of the tested compounds 1-9 and (B) anti-SARS-CoV-2 activities of the tested compounds 10-17.
Figure 7B:
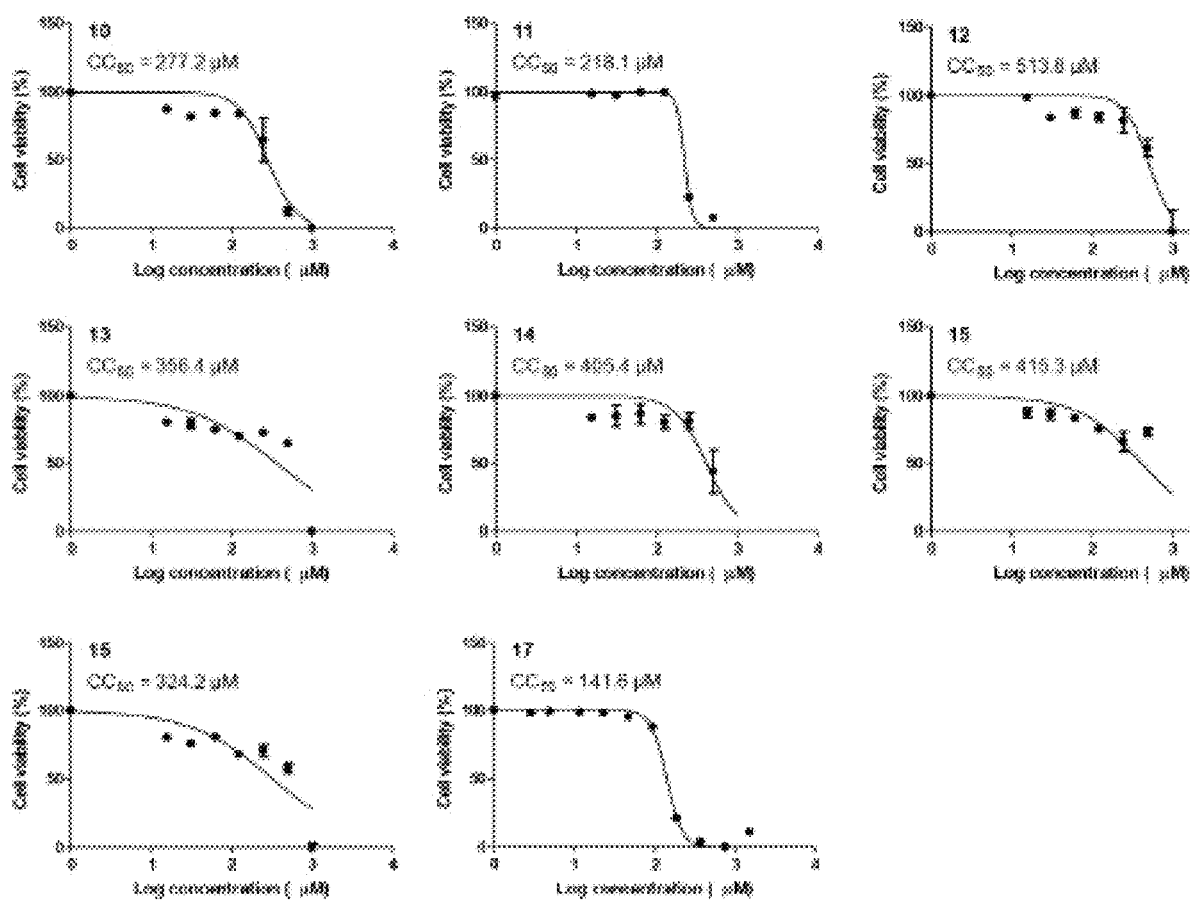
Figure 8A:
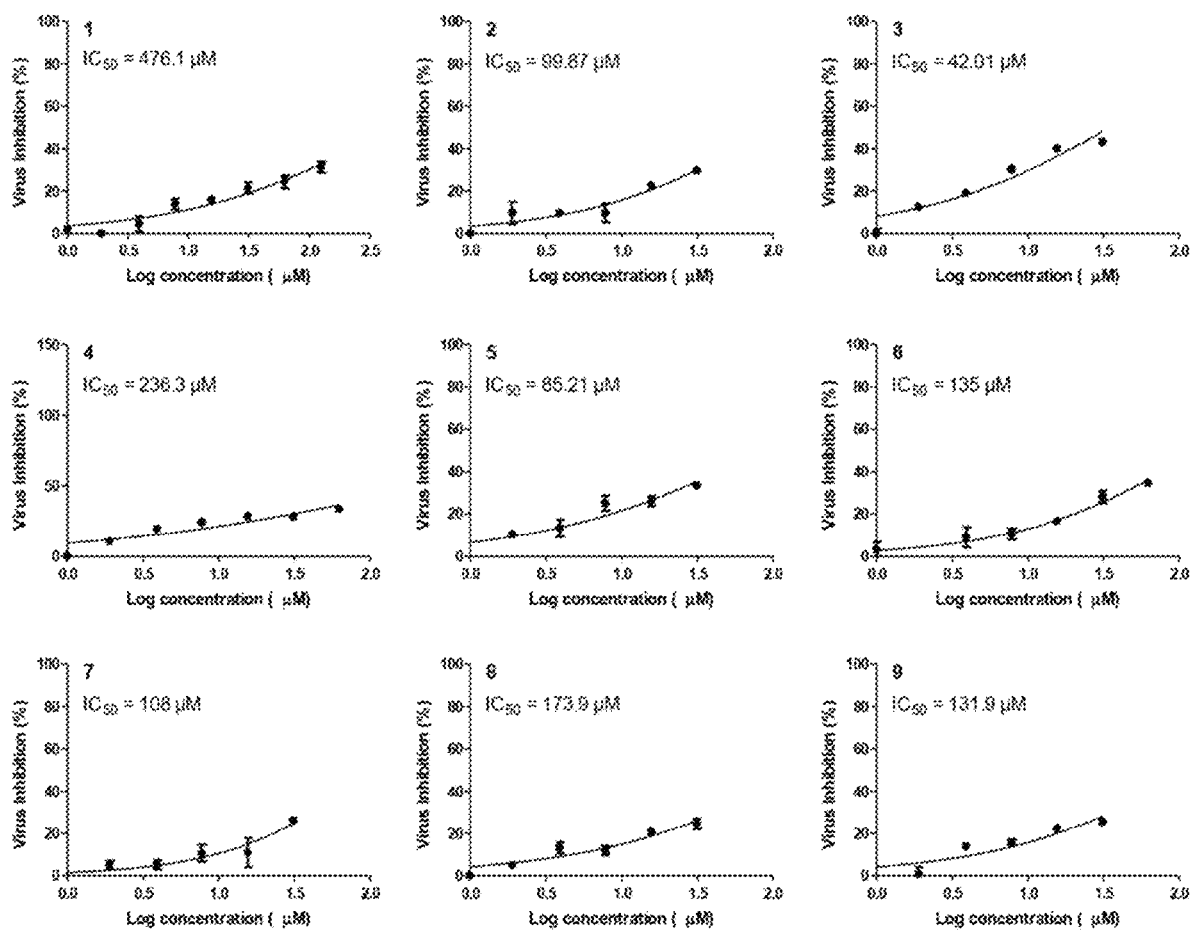
FIGS. 8A-B show (A) half-maximal cytotoxic concentrations of the tested compounds (1-9) (CC50) on Vero E6 cells, and (B) half-maximal inhibitory concentrations ($IC_{50}$) against NRC-03-nhCoV in Vero E6. Inhibitory concentration 50% ($IC_{50}$) values were calculated using nonlinear regression analysis of GraphPad Prism software version 5.01 by plotting log inhibitor versus normalized response (variable slope).
Figure 8B:
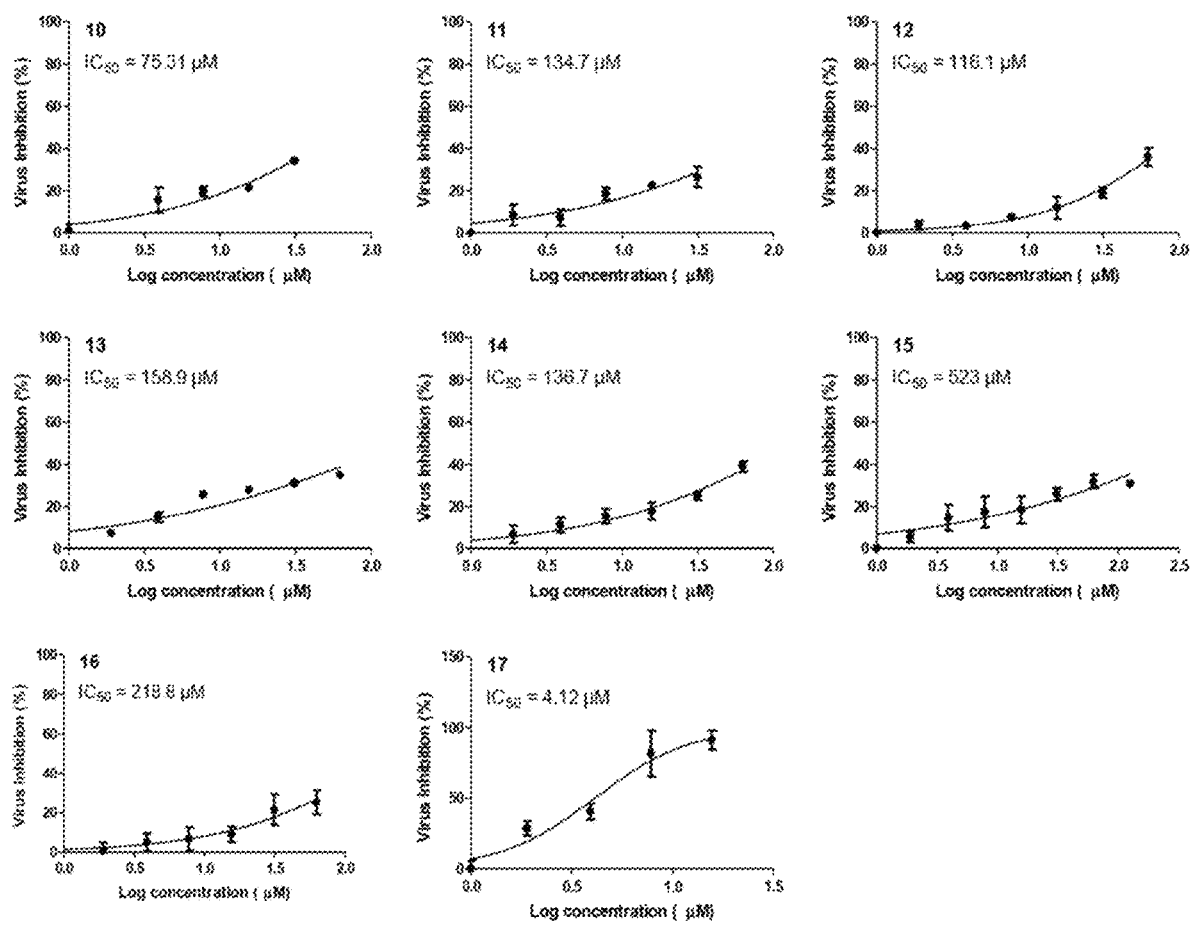

Compound 17 showed promising anti-SARS-CoV-2 activity at non-toxic concentrations. To identify the proper concentrations to define the antiviral activity of the selected compounds, half maximal cytotoxic concentration "CC50" was calculated for each individual drug (FIGS. 7A-B). The antiviral screening revealed that one compound "17" out of the tested panel compounds exhibits a promising in vitro activity against SARS-CoV-2 "NRC 03-nhCoV" (IC50=4.12 µM) with a satisfactory selectivity index (>7.5) (FIG. 7A-B and Table 4).

TABLE 4

Selectivity index of tested compounds 1-17.

| Compound | $CC_{50}$ | $IC_{50}$ | Selectivity Index ($CC_{50}/IC_{50}$) |
| --- | --- | --- | --- |
| 1 | 189.9 | 476.1 | 0.39 |
| 2 | 97.3 | 99.87 | 0.97 |
| 3 | 97.4 | 42.01 | 2.32 |
| 4 | 157.2 | 236.3 | 0.67 |
| 5 | 90.62 | 85.21 | 1.06 |
| 6 | 208.8 | 135 | 1.55 |
| 7 | 97.42 | 108 | 0.9 |
| 8 | 170 | 173.9 | 0.98 |
| 9 | 185.3 | 131.9 | 1.4 |
| 10 | 277.2 | 75.31 | 3.68 |
| 11 | 218.1 | 134.7 | 1.62 |
| 12 | 513.8 | 116.1 | 4.42 |
| 13 | 356.4 | 158.9 | 2.24 |
| 14 | 405.4 | 136.7 | 2.96 |
| 15 | 415.3 | 523 | 0.79 |
| 16 | 324.2 | 218.6 | 1.48 |
| 17 | 141.6 | 4.12 | 34.36 |

Figure 9:
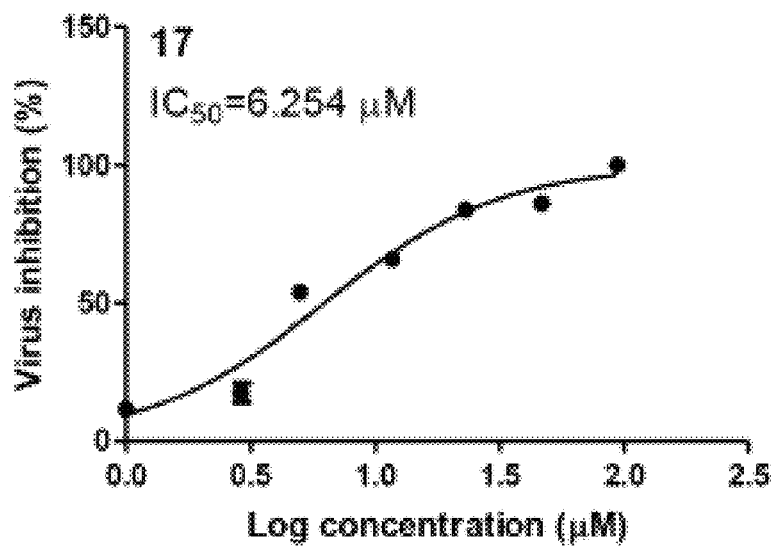
FIG. 9 shows half-maximal inhibitory concentrations (IC50) against Middle East Respiratory Syndrome related coronavirus isolate of NRCE-HKU270 (accession number: KJ477103.2). NRCE-HKU270 was obtained from CSEIVs [45] in Vero E6 cells using crystal violet assay. Inhibitory concentration 50% ($IC_{50}$) values were calculated using nonlinear regression analysis of GraphPad Prism software version 5.01 by plotting log inhibitor versus normalized response (variable slope).

Compound 17 showed promising anti-MERS-CoV activity and non-toxic concentrations To assess the antiviral activity of compound 17 against other highly pathogenic coronaviruses, we assayed its activity against MERS-CoV virus "NRCE-HKU270". Interestingly, compound 17 showed promising antiviral activity against NRCE-HKU270 at micromolar concentrations (FIG. 9).

Structure-Activity Relationship (SAR) Analysis

Figure 10:
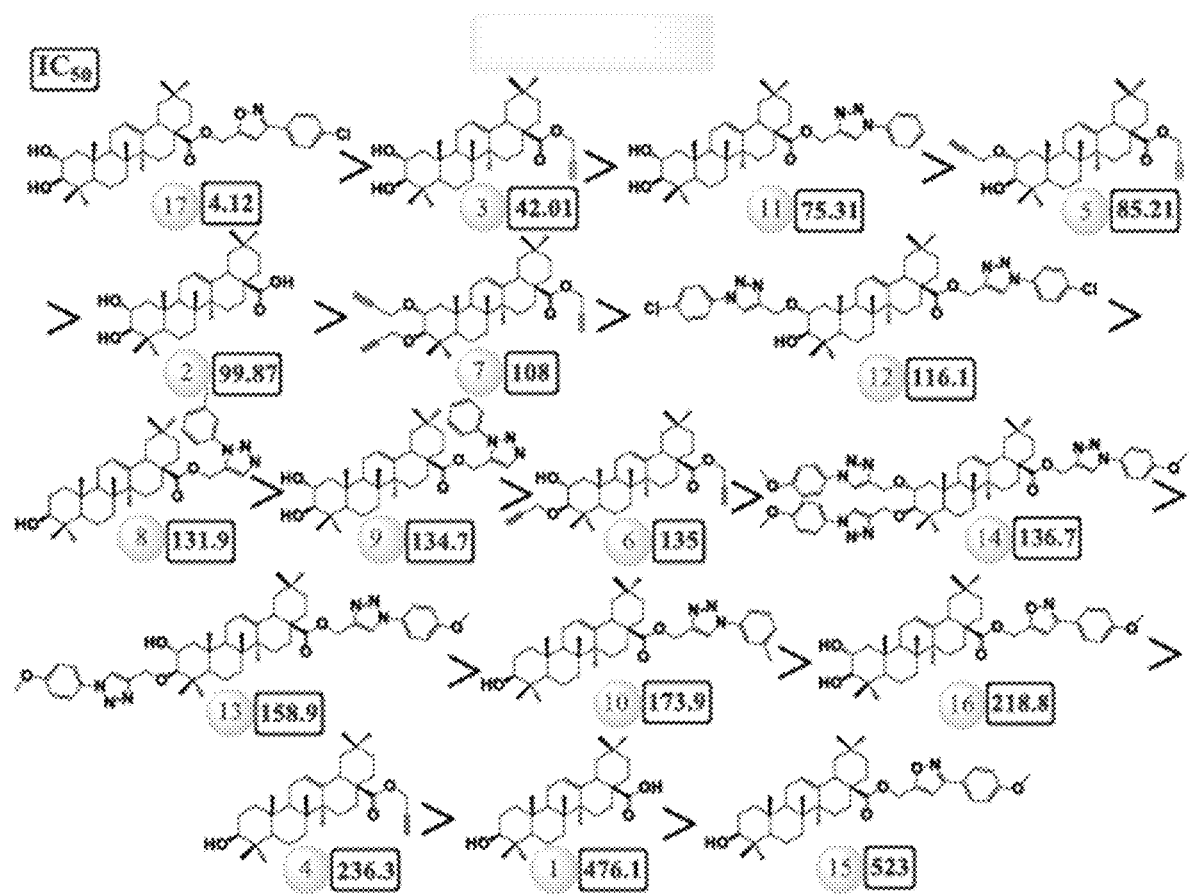
FIG. 10 shows a structure-activity relationship (SAR) of the selected tested compounds (1-17) based on both their cytotoxic and docking studies against SARS-CoV-2.

By analyzing the relationship between the structures of the selected tested compounds 1-17 and their cytotoxic $IC_{50}$ values (FIG. 10) and using the molecular docking results as a way to relate their activities to their binding affinities as SARS-CoV-2 main protease inhibitors, we may conclude that; (a) The common shared steroidal nucleus of the selected tested compounds 1-17 appeared to be very promising for their antiviral activities. Molecular docking revealed the great stabilization of the tested compounds inside the branched large pocket of SARS-CoV-2 main protease as a proposed mechanism of action. (b) The presence of OH groups at positions 2 and 3 of the steroidal nucleus seems to be very crucial for the antiviral activity. Most compounds 3, 17, and 10 containing both 2- and 3-OH groups achieved high to moderate activities (4.12-99.87 µM). Docking studies referred to the involvement of both OH groups in hydrogen bond formations with Thr24 and/or Thr26 amino acids of the binding pocket. (c) Compound 17 containing the isoxazole side chain with a p-chlorophenyl substitution (an electron withdrawing lipophilic group) achieved a very high cytotoxic activity (IC50=4.12 µM). However, both compounds 15 and 16 that contain the isoxazole side chain with a p-methoxyphenyl substitution (an electron donating hydrophilic group) provided low cytotoxic activities ($IC_{50=218.8}$ and 523 µM, respectively). Therefore, the lipophilic p-chloro group is very important for the antiviral activity. Again, compound 16 containing both 2- and 3-OH groups showed a higher cytotoxic activity compared to that of compound 15 with only 3-OH group as mentioned above. (d) The presence of the acetyl methylene group at positions 2 and/or 3 in compounds 5, 6 and 7 gave better cytotoxic activities compared to that of the heteroaromatic ring substitutions at the same positions in compounds 12, 14, and 13. I The cytotoxic activity of compound 17 containing the isoxazole side chain with a pchlorophenyl substitution (IC50=4.12 11M) was clearly higher than the respective same compound 10 with a phenyl triazole side chain instead (IC50=75.31 µM).

Collectively, these studies greatly suggested the very promising affinities of the selected tested compounds 1-17 against SARS-CoV-2, especially compounds 3 and 17. Accordingly, we recommend such compounds for more advanced in vitro and in vivo studies to obtain an effective therapeutic against the pandemic SARS-CoV-2. Moreover, the aforementioned studied compounds could be used alone or in combinations for inhibiting SARS-CoV-2 anti-viral activities.

Figure 11:
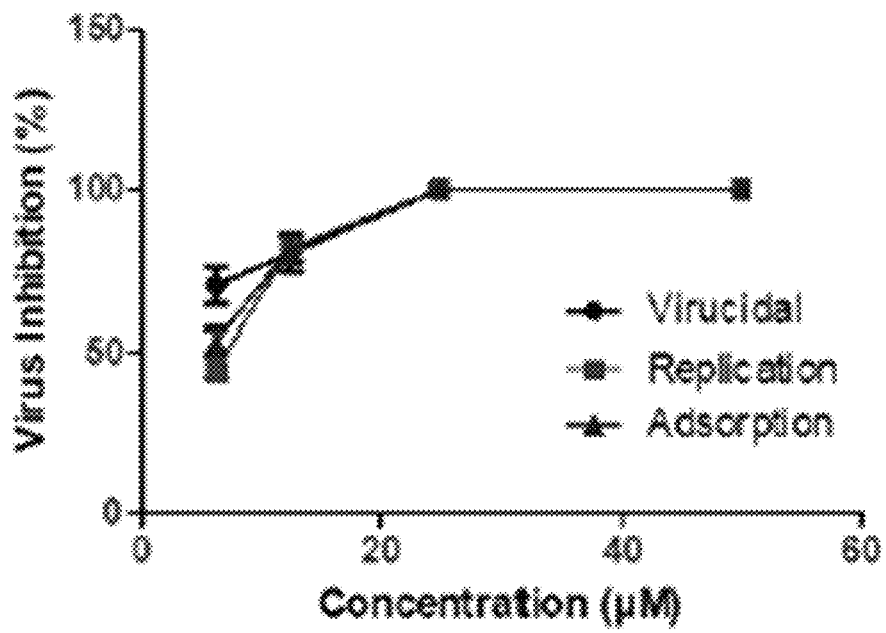
FIG. 11 shows mode of antiviral action of compound 17 of the present disclosure against SARS-CoV-2 in Vero E6 cells as measured by plaque reduction assay. Inhibitory percent values were calculated and plotted against inhibitor concentration using GraphPad Prism software version 5.01.
Figure 12A:
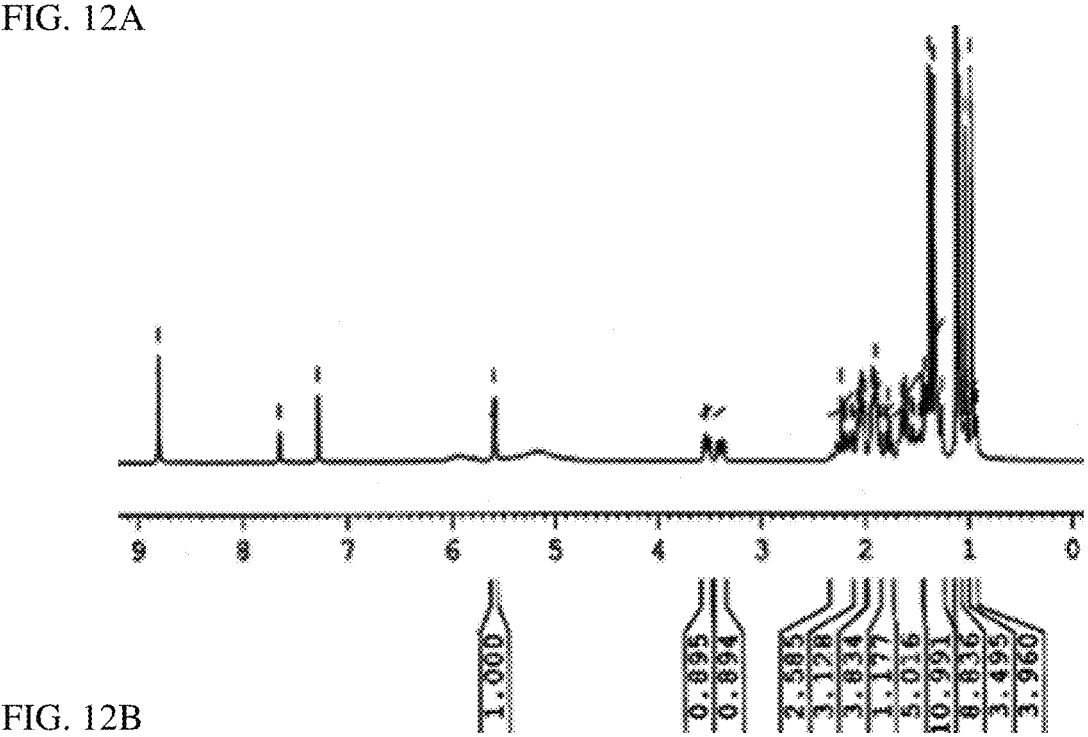
FIGS. 12A-B show (A)$^1$H NMR and (B)$^{13}$C NMR spectra of oleanolic acid.
Figure 12B:
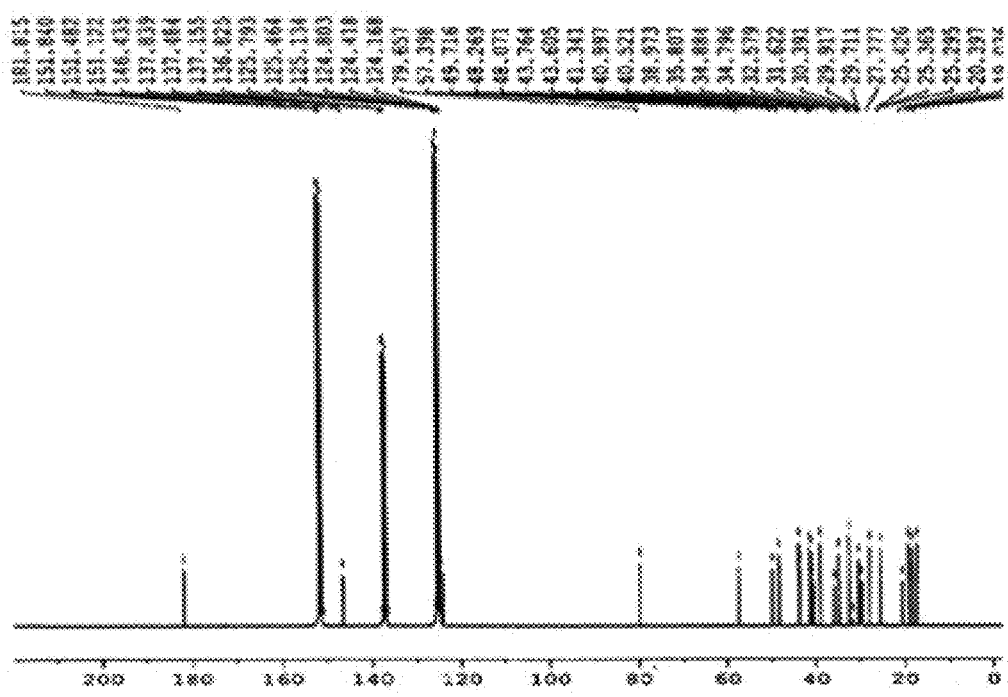
Figure 13A:
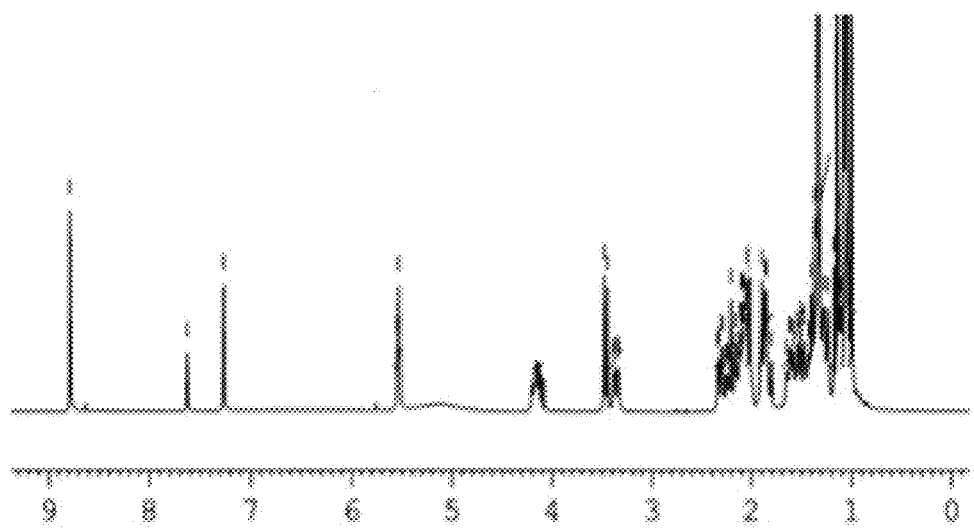
FIGS. 13A-B show (A)$^1$H NMR and (B)$^{13}$C NMR spectra of maslinic acid.
Figure 13B:
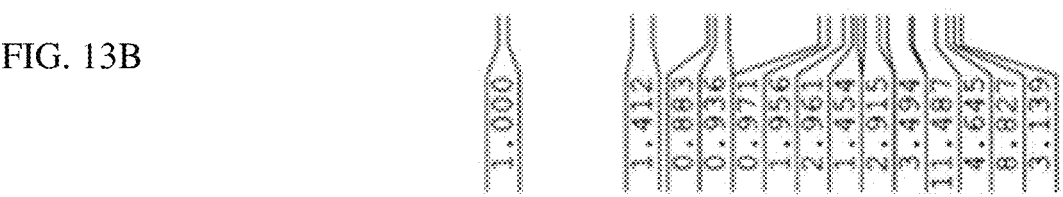
Figure 13B:
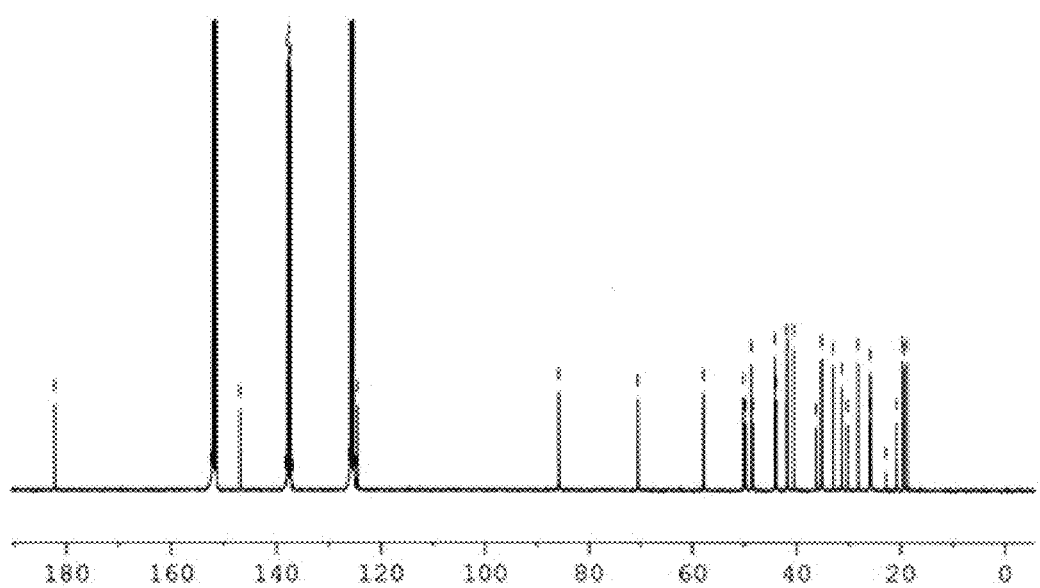
Figure 14A:
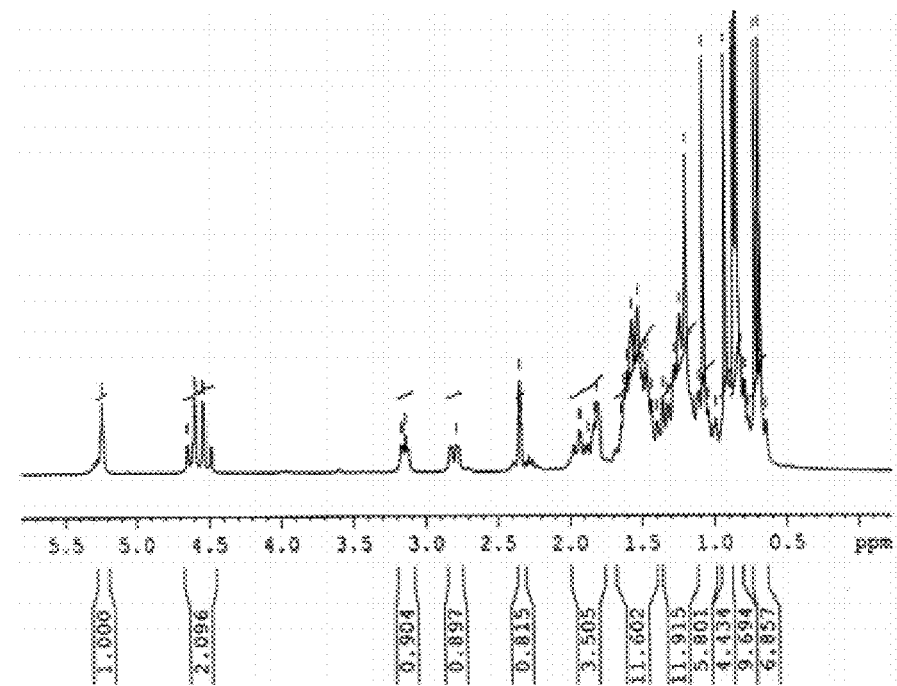
FIGS. 14A-B show (A)$^1$H NMR and (B)$^{13}$C NMR spectra of triterpenoid compound 3 of the present disclosure.
Figure 14B:
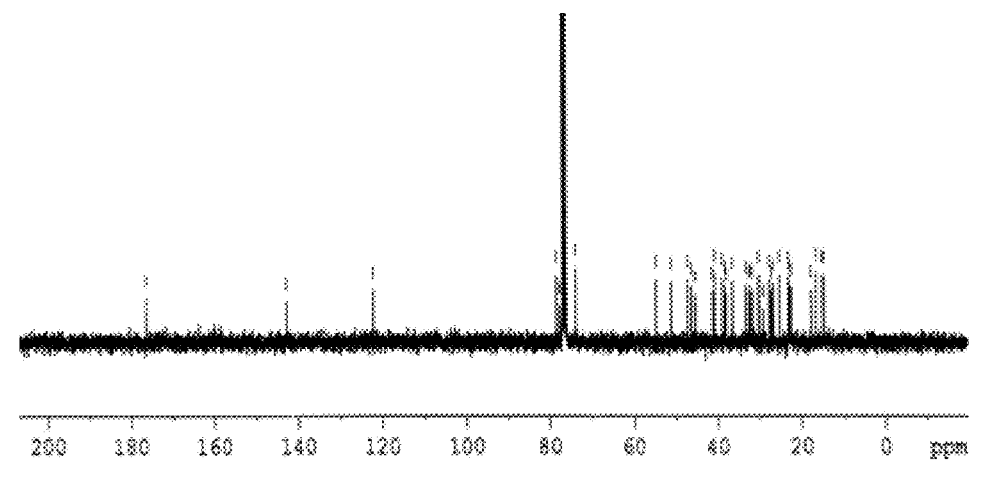
Figure 15A:
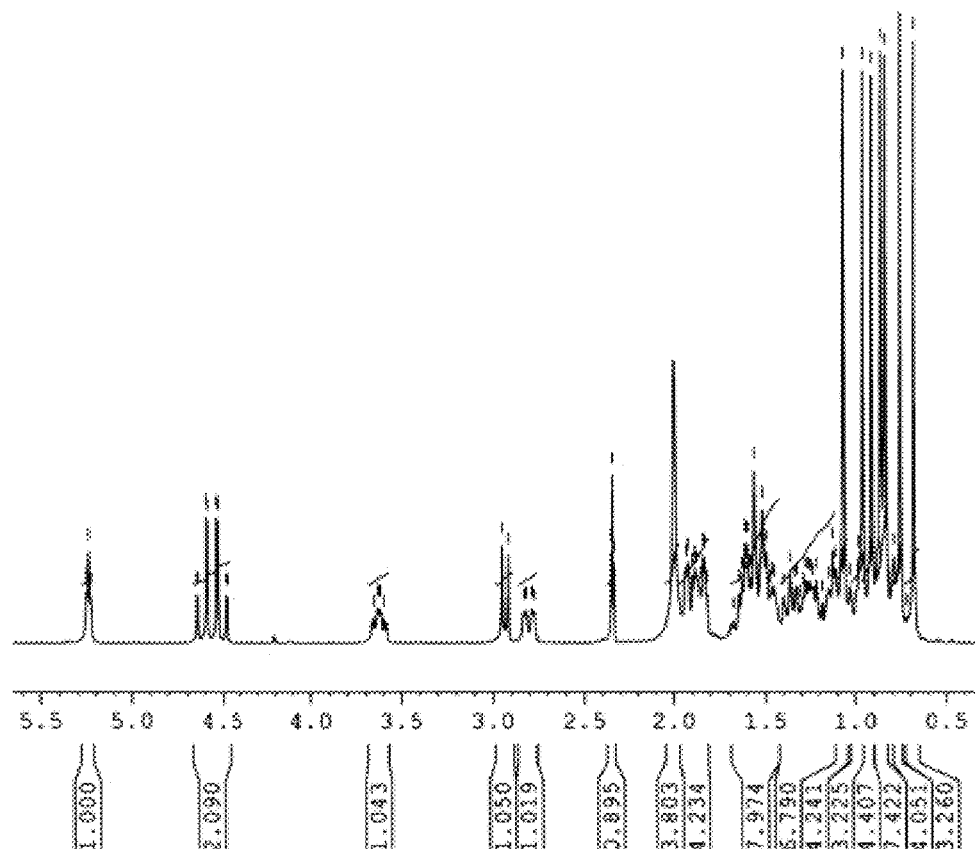
FIGS. 15A-B show (A)$^1$H NMR and (B)$^{13}$C NMR spectra of triterpenoid compound 4 of the present disclosure.
Figure 15B:
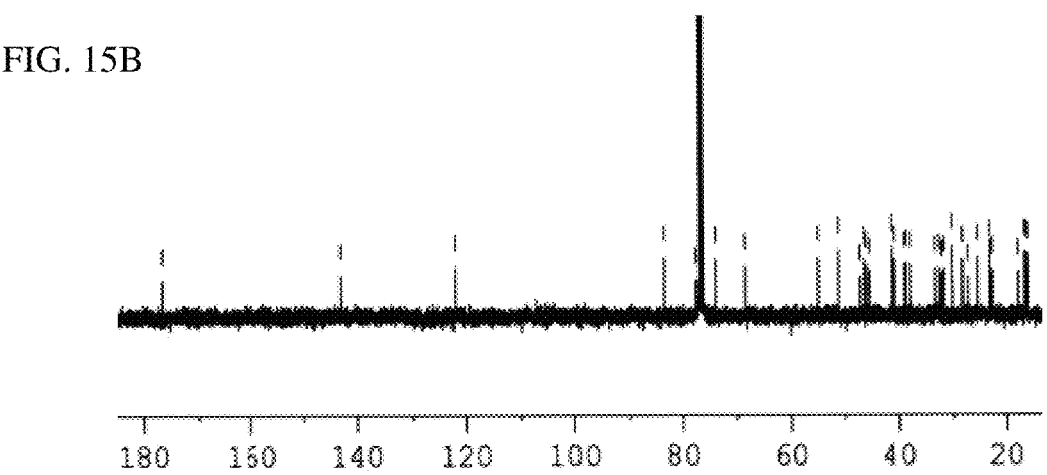
Figure 16A:
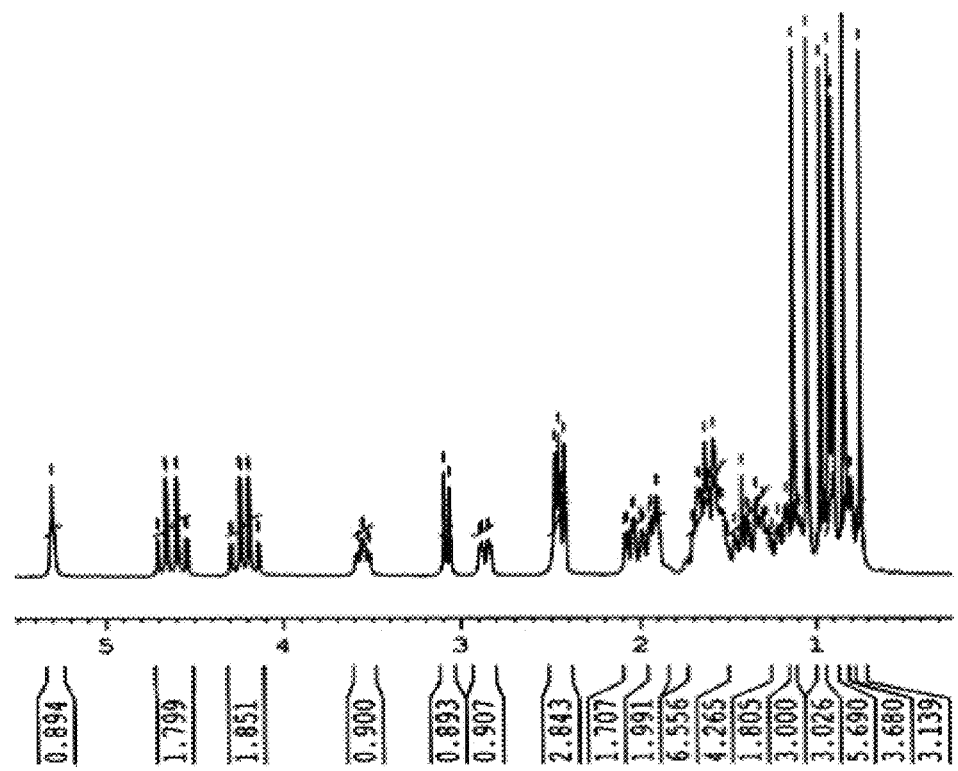
FIGS. 16A-B show (A)$^1$H NMR and (B)$^{13}$C NMR spectra of triterpenoid compound 5 of the present disclosure.
Figure 16B:
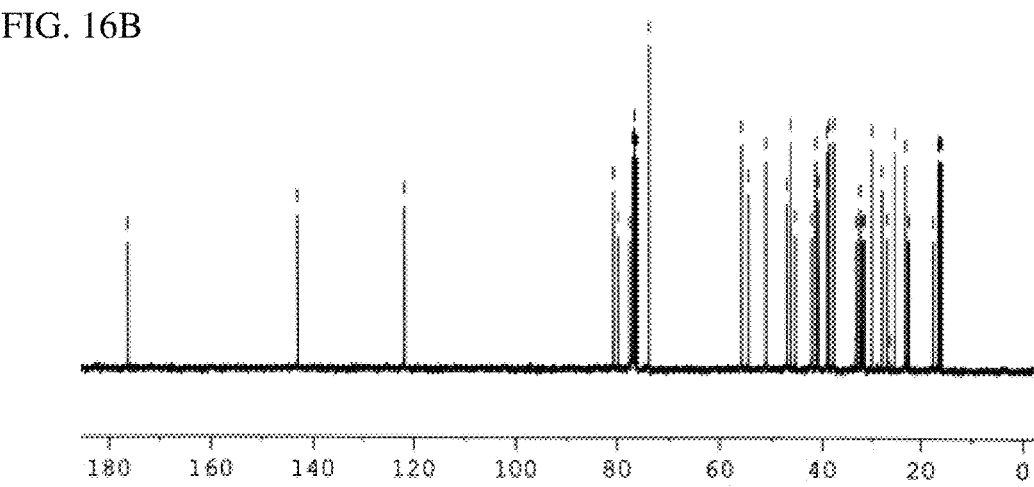
Figure 17A:
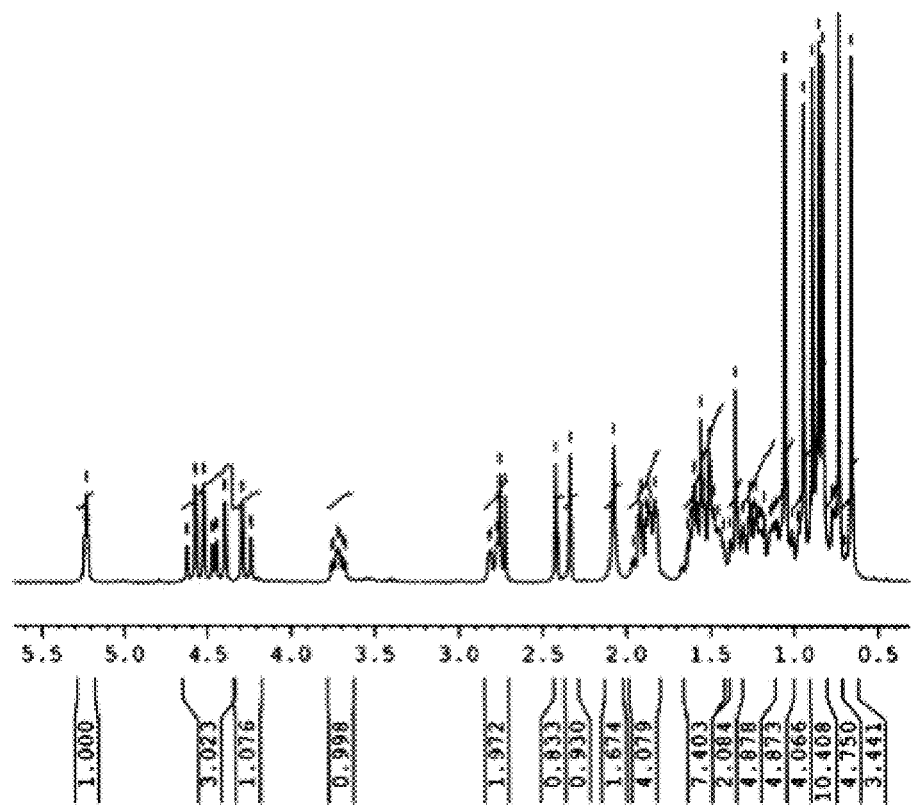
FIGS. 17A-B show (A)$^1$H NMR and (B)$^{13}$C NMR spectra of triterpenoid compound 6 of the present disclosure.
Figure 17B:
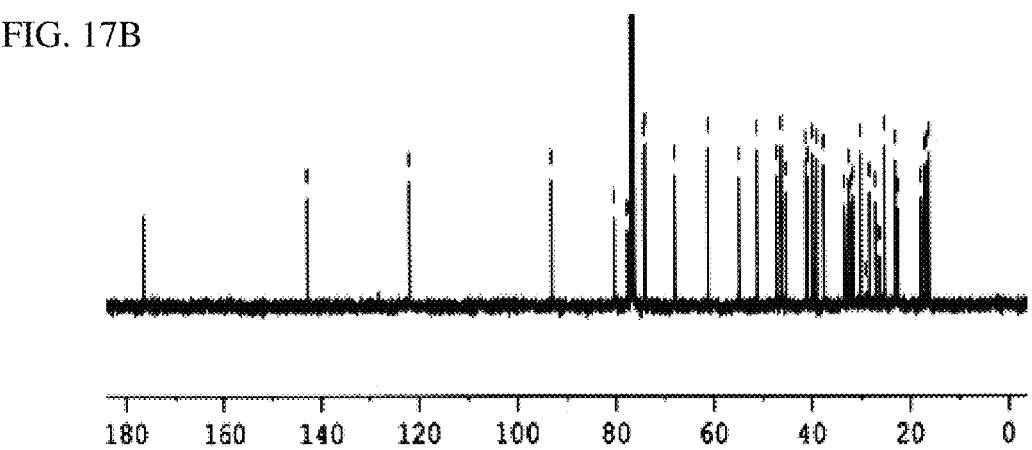
Figure 18A:
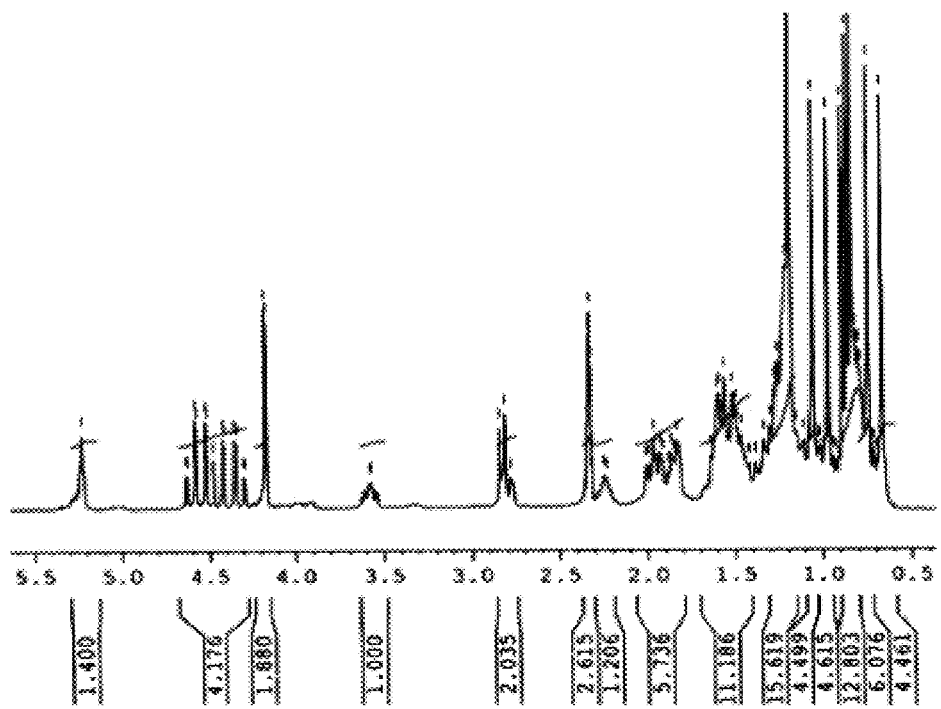
FIGS. 18A-B show (A)$^1$H NMR and (B)$^{13}$C NMR spectra of triterpenoid compound 7 of the present disclosure.
Figure 18B:
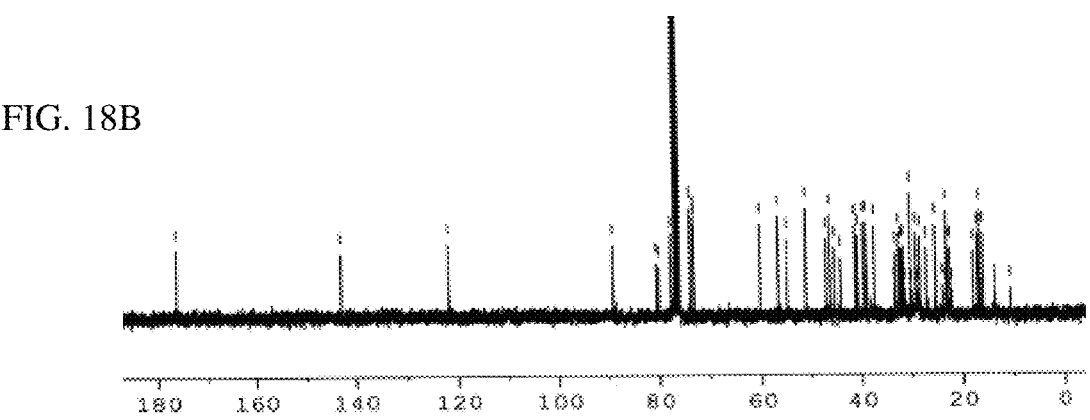
Figure 19A:
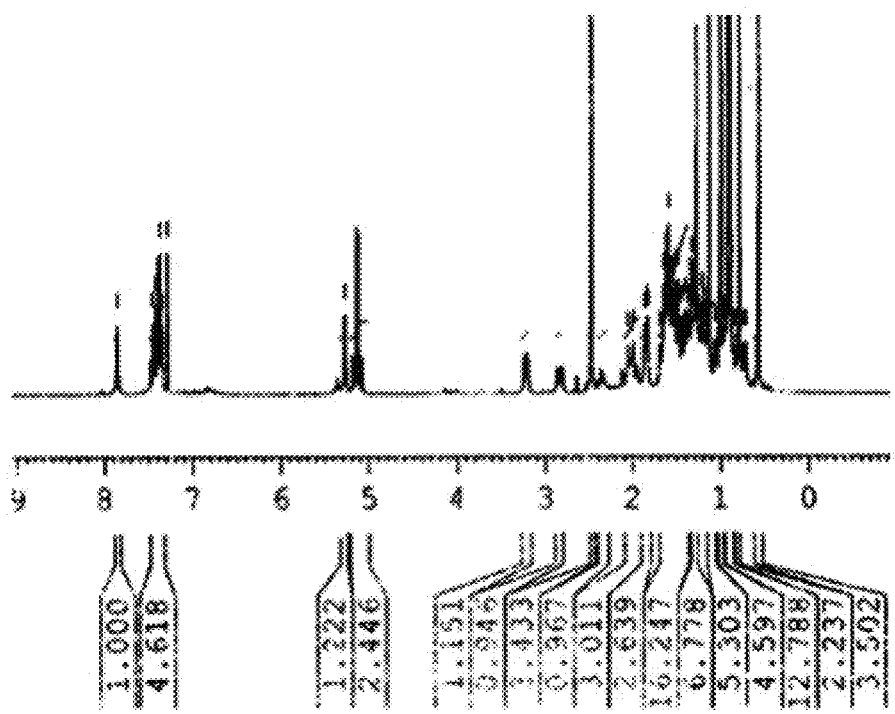
FIGS. 19A-B show (A)$^1$H NMR and (B)$^{13}$C NMR spectra of triterpenoid compound 8 of the present disclosure.
Figure 19B:
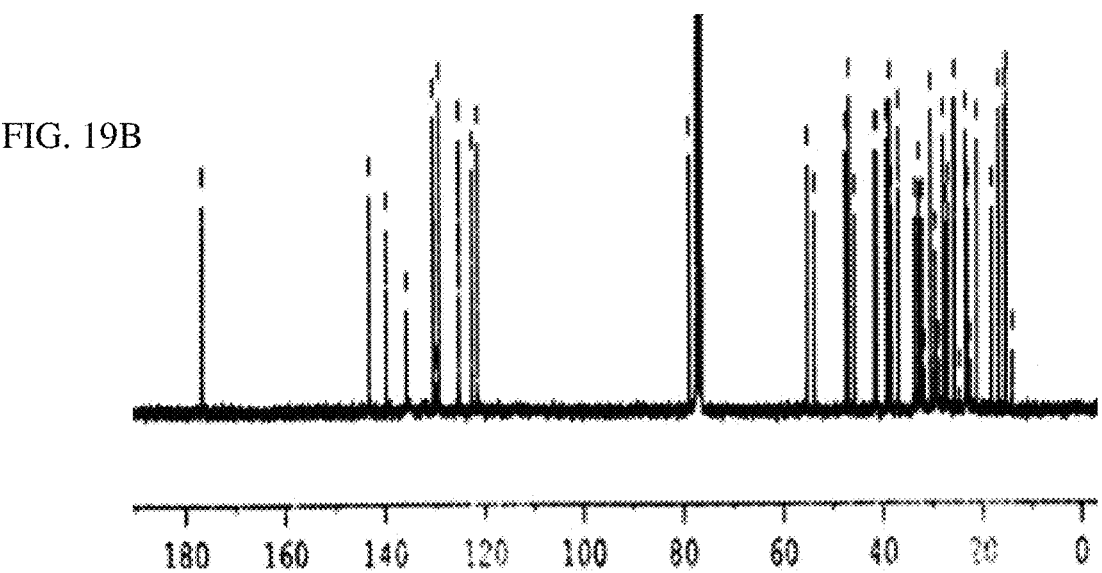
Figure 20A:
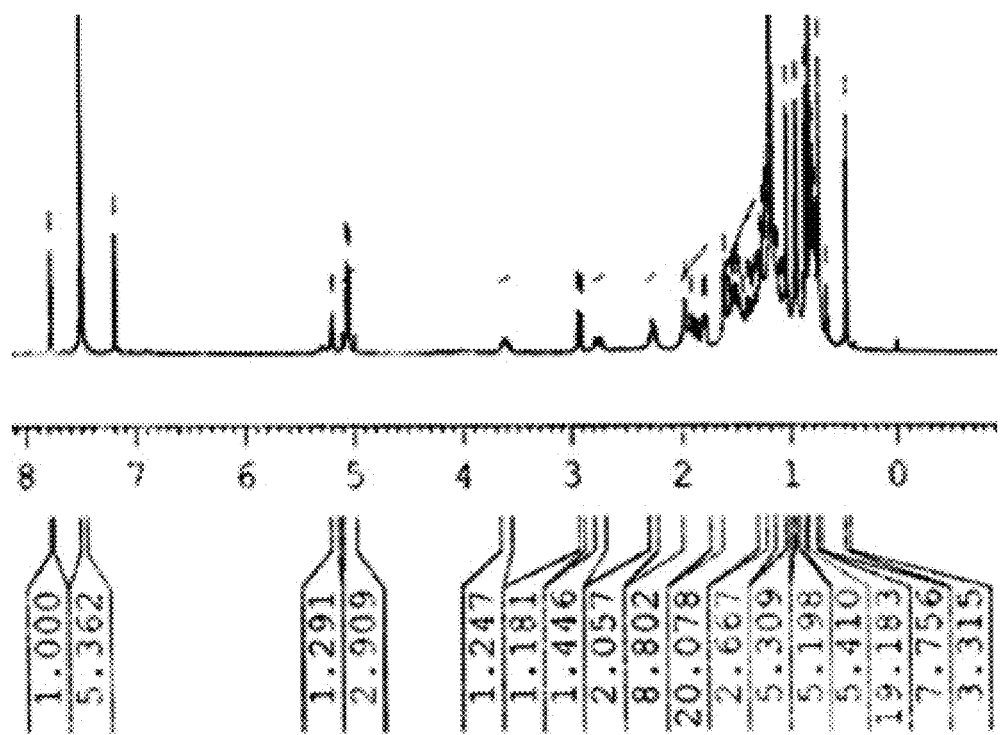
FIGS. 20A-B show (A)$^1$H NMR and (B)$^{13}$C NMR spectra of triterpenoid compound 9 of the present disclosure.
Figure 20B:
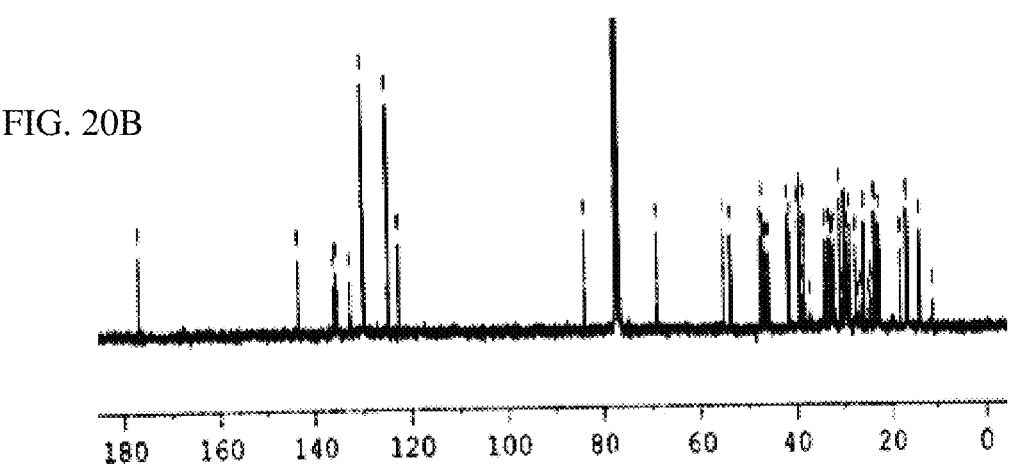
Figures 21A, 21B:
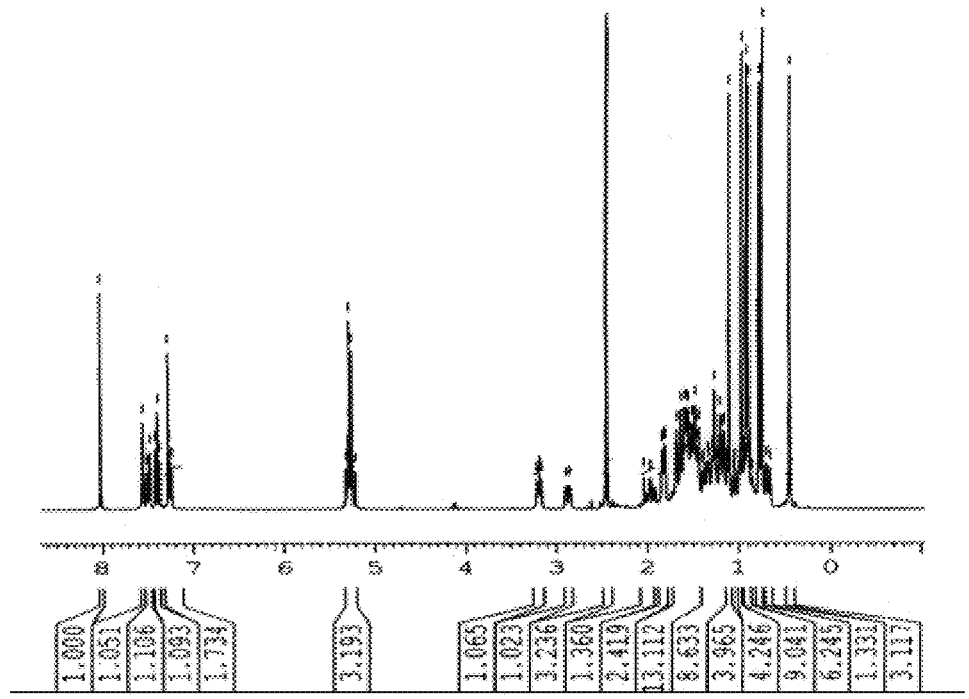
FIGS. 21A-B show (A)$^1$H NMR and (B)$^{13}$C NMR spectra of triterpenoid compound 10 of the present disclosure.
Figure 22A:
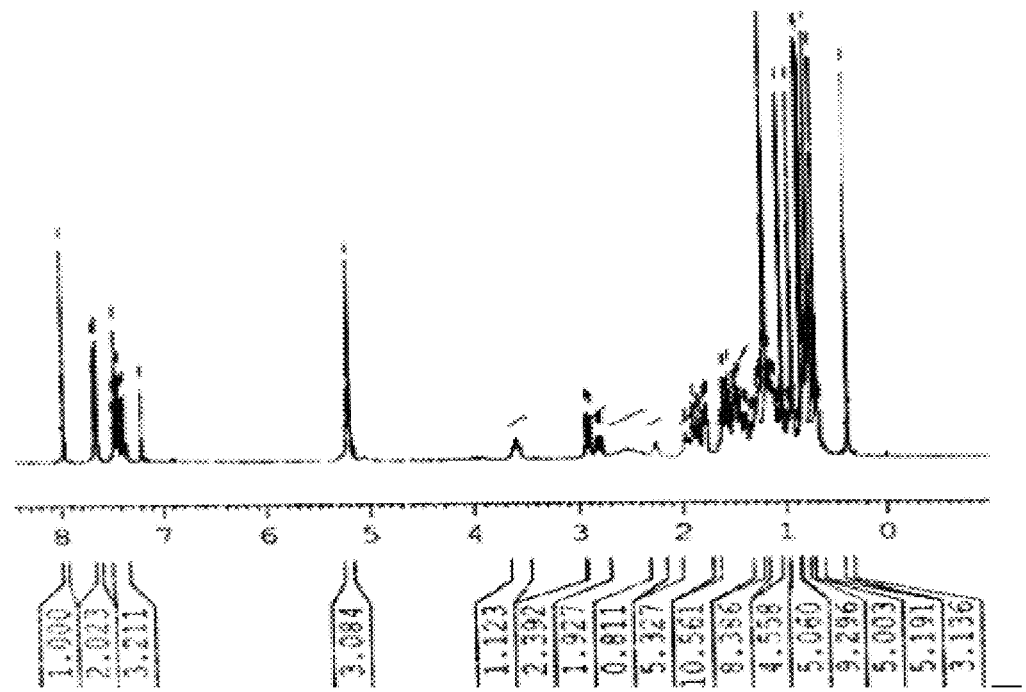
FIGS. 22A-B show (A)$^1$H NMR and (B)$^{13}$C NMR spectra of triterpenoid compound 11 of the present disclosure.
Figure 22B:
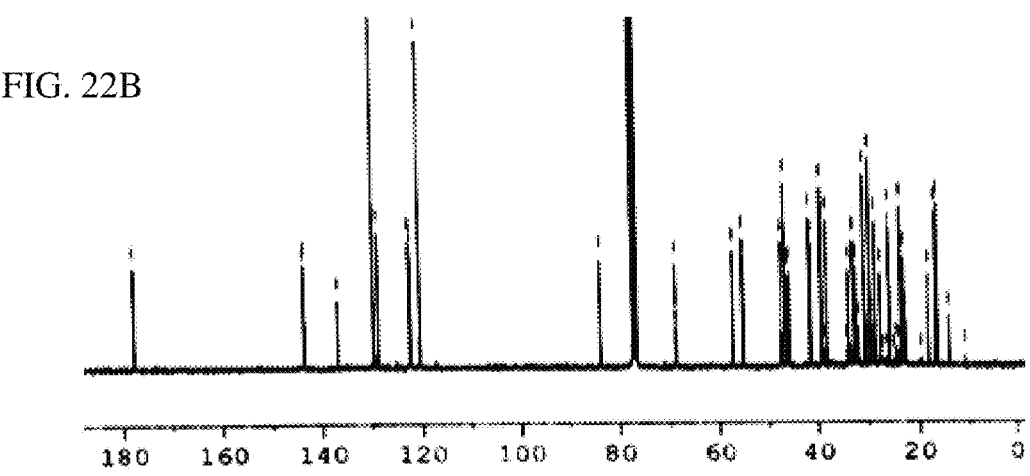
Figure 23A:
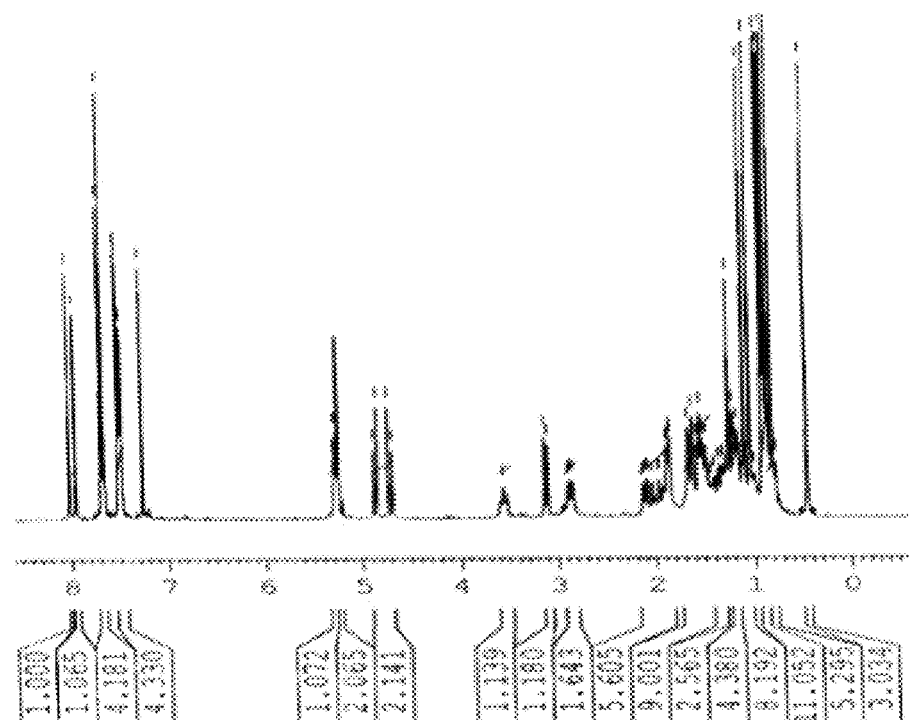
FIGS. 23A-B show (A)$^1$H NMR and (B)$^{13}$C NMR spectra of triterpenoid compound 12 of the present disclosure.
Figure 23B:
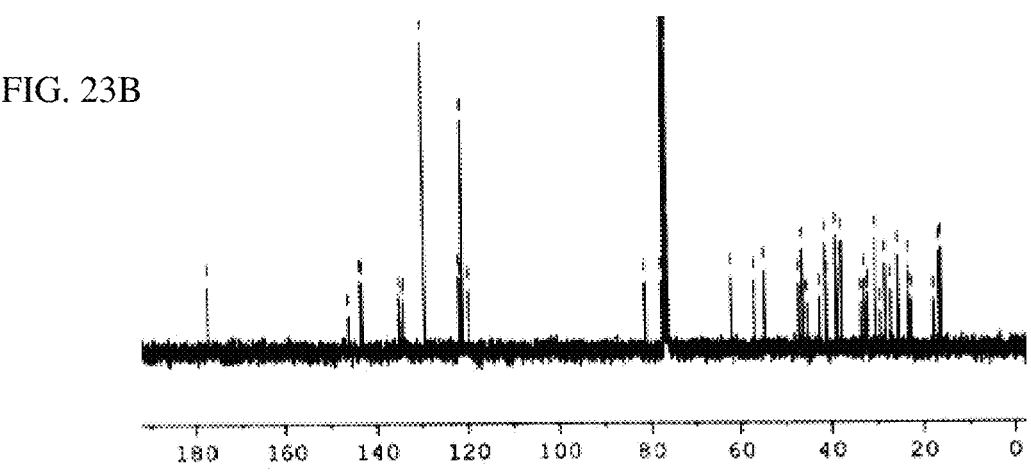
Figure 24A:
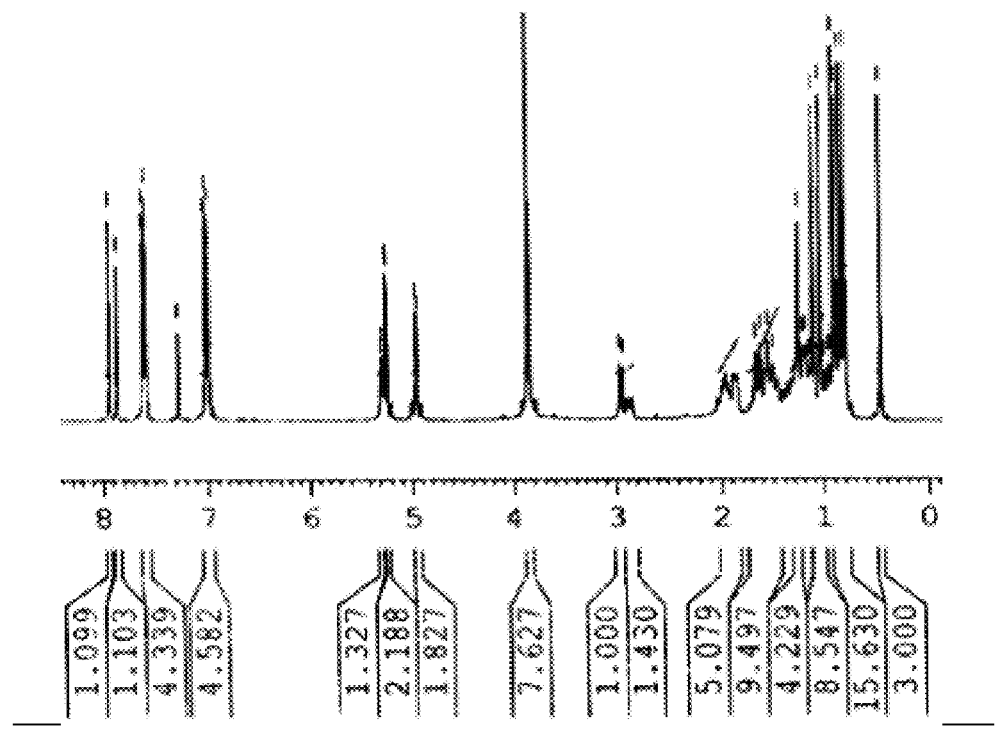
FIGS. 24A-B show (A)$^1$H NMR and (B)$^{13}$C NMR spectra of triterpenoid compound 13 of the present disclosure.
Figure 24B:
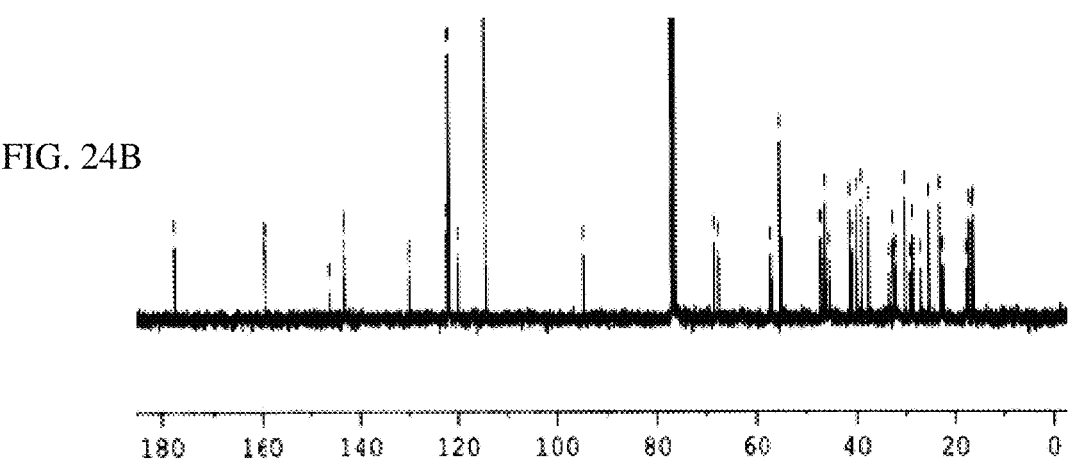
Figure 25A:
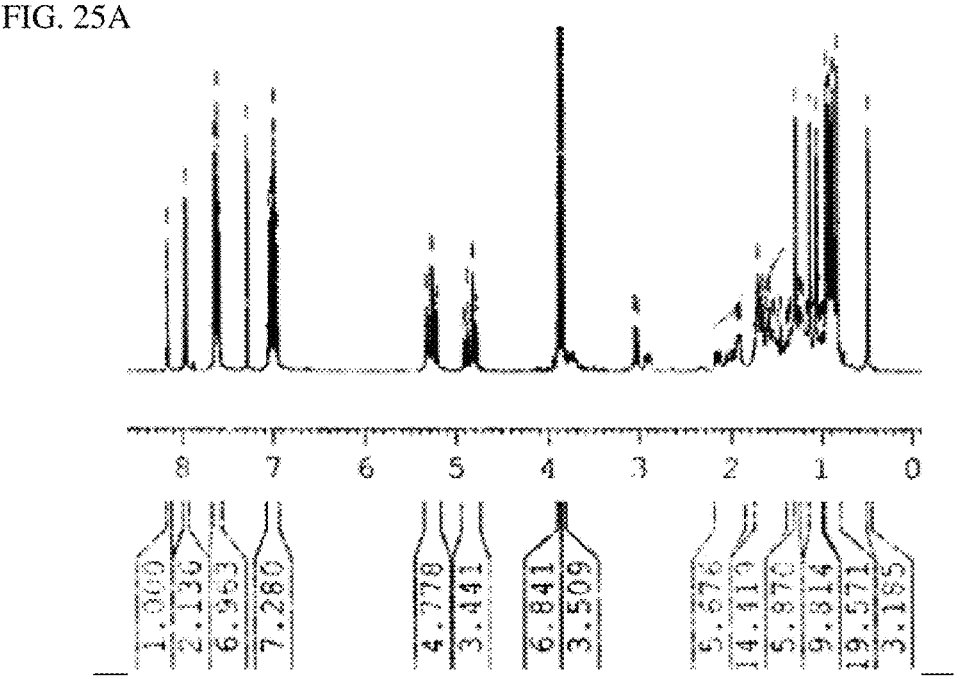
FIGS. 25A-B show (A)$^1$H NMR and (B)$^{13}$C NMR spectra of triterpenoid compound 14 of the present disclosure.
Figure 25B:
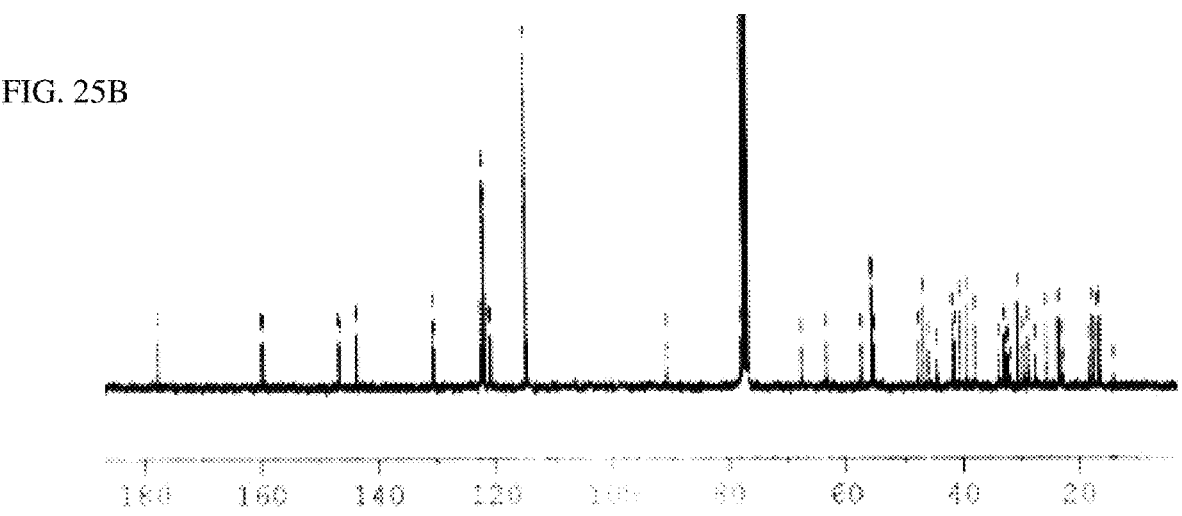
Figure 26A:
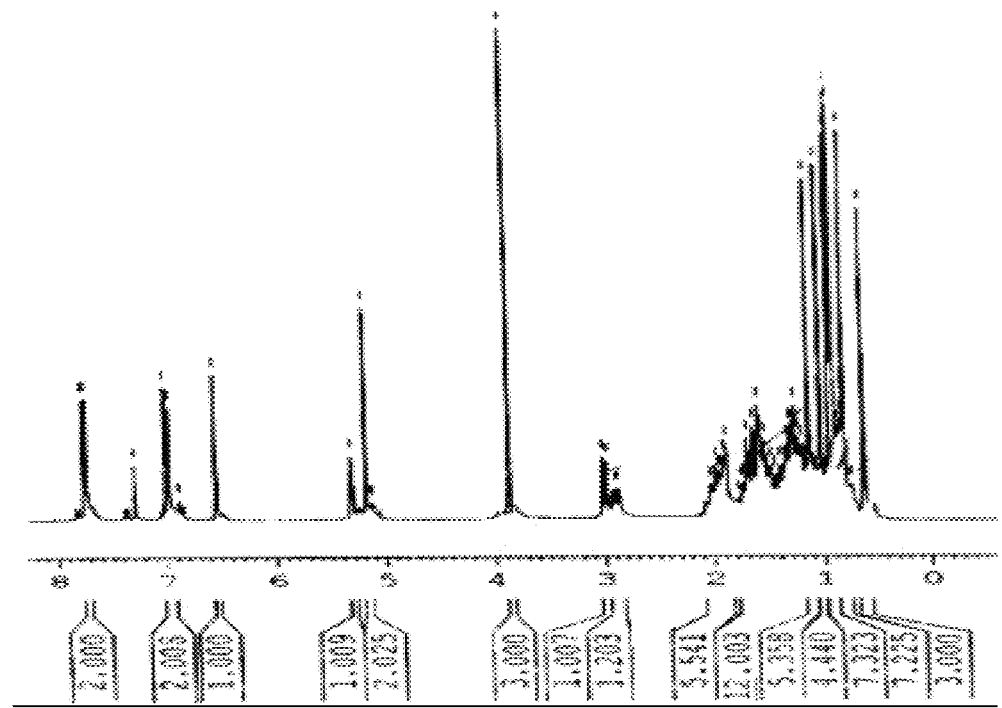
FIGS. 26A-B show (A)$^1$H NMR and (B)$^{13}$C NMR spectra of triterpenoid compound 15 of the present disclosure.
Figure 26B:
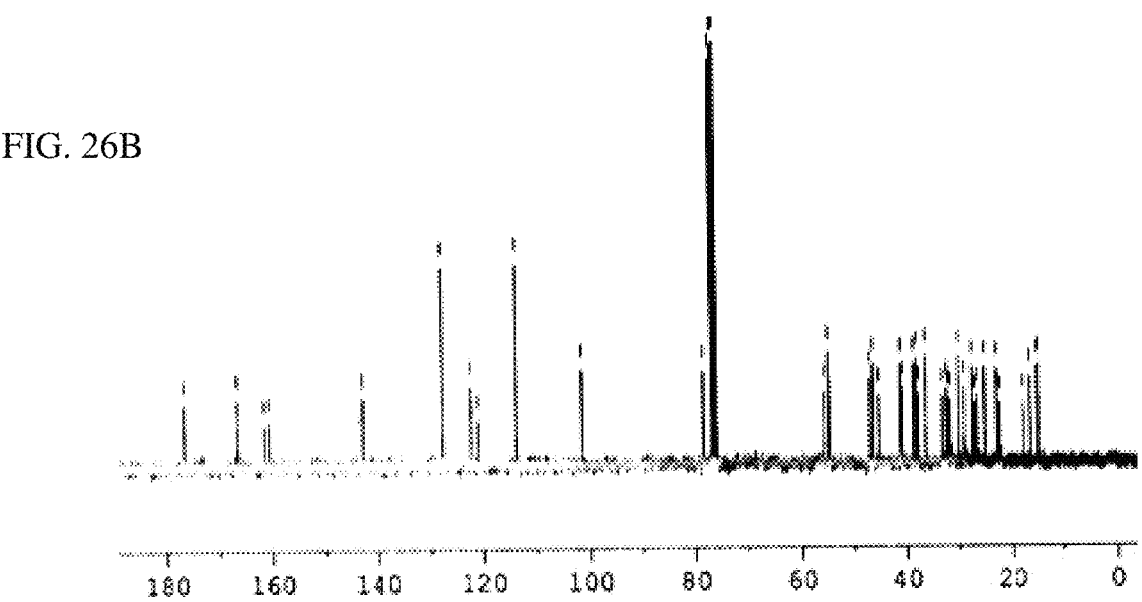
Figure 27A:
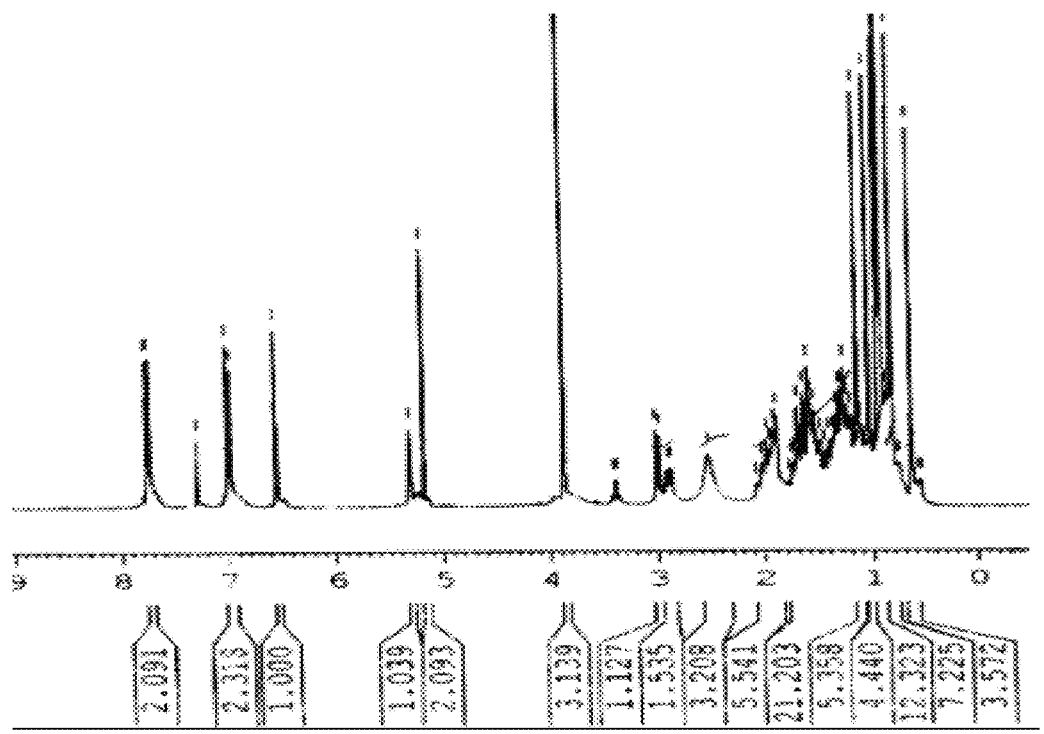
FIGS. 27A-B show (A)$^1$H NMR and (B)$^{13}$C NMR spectra of triterpenoid compound 16 of the present disclosure.
Figure 27B:
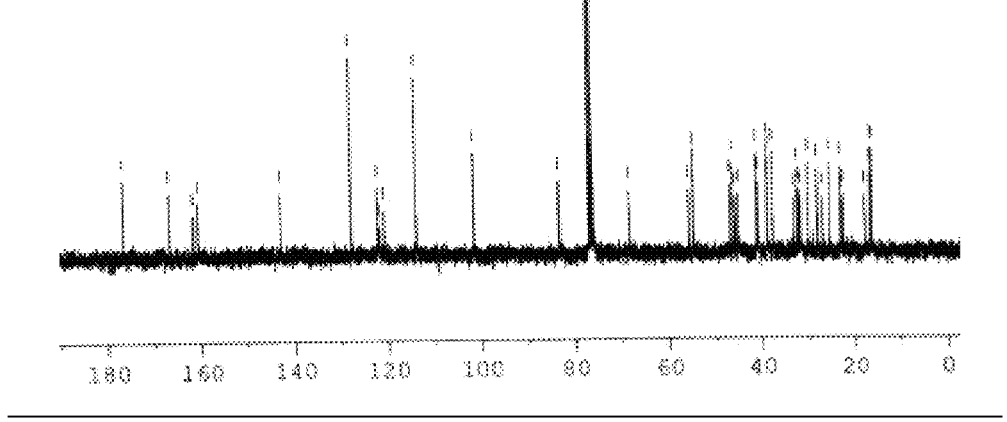
Figure 28A:
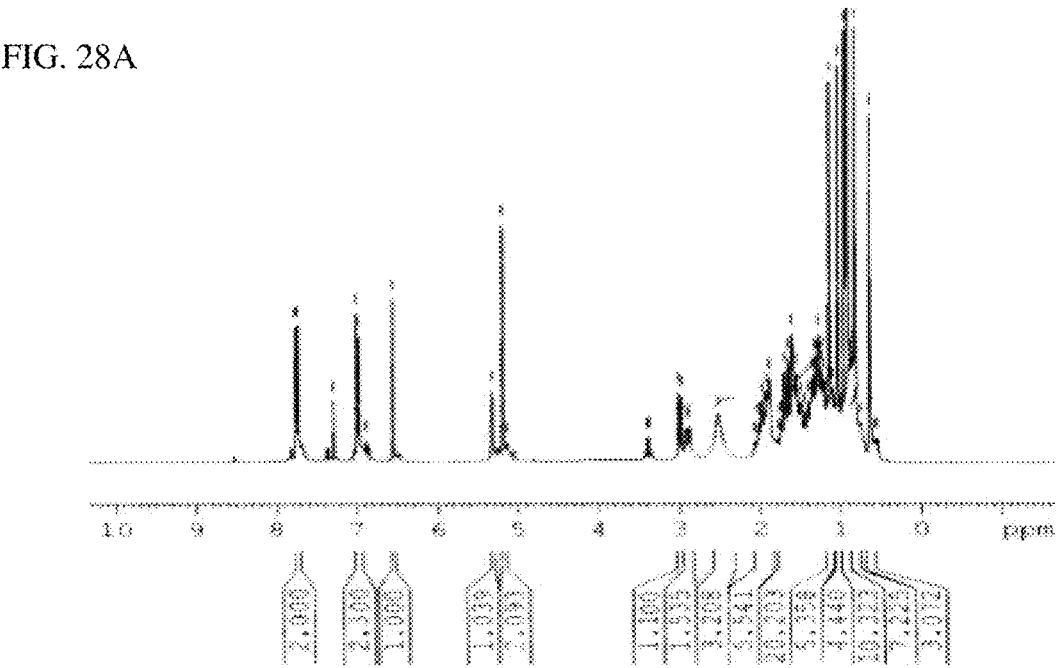
FIGS. 28A-B show (A)$^1$H NMR and (B)$^{13}$C NMR spectra of triterpenoid compound 17 of the present disclosure.
Figure 28B:
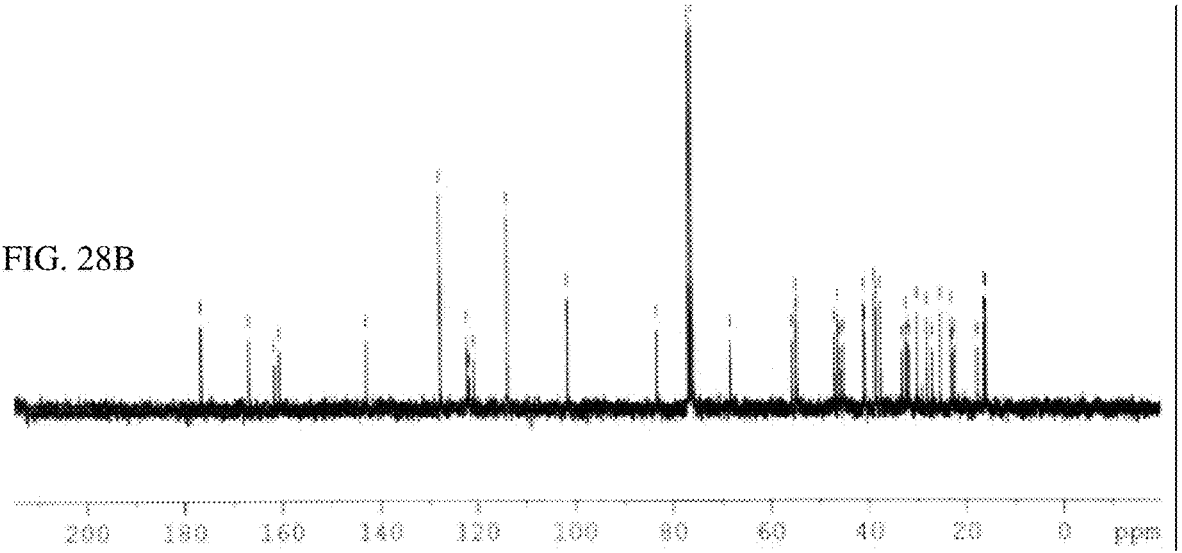

The virucidal effect of the antiviral compound 17 against SARS-CoV-2 virus has been studied, and interference with viral adsorption and replication was demonstrated. Besides the virucidal effect of compound 17, it could efficiently impair viral replication and adsorption (FIG. 11).

Example 2

Green Chemistry Condition for Extraction and Purification of OA 1 and MA 2 from the Pomace Olive of *Olea europaea* L.

Using cultivar Chemlali pomace olive resulting from olive fruit pressing as a natural substance, the most suitable conditions to carry out the extraction and purification of compounds 1 and 2 were explored. The optimal conditions were determined to be the ultrasonic power of 250 W, extraction temperature of 60° C., ratio of liquid to solid of 30 mL/g, and 60 min extraction time, using aqueous ethanol (concentration of 70%) as the extracting solvent. After the evaporation of the ethanol under reduced pressure, the extract was precipitated at +4° C. for 48 h. After filtration, the extract was centrifuged at 5000 rpm/5 min, yielding a mixture of compounds 1 and 2 according to TLC analysis (13.5% w/w). The crude mixture was recrystallized from the mixture EtOH/AcOEt (8:2, v/v) to obtain pure maslinic acid 2 (9.2 mg/g DW). The filtrate was concentrated and recrystallized from ethanol to obtain pure oleanolic acid 1 (3.6 mg/g DW).

Multicomponent Synthesis of 1,5-Disubstituted Triazoles in Water Catalyzed by Cp*RuCl (PPh3)2

To a solution of alkyne 3 or 4 (0.1 g) and NaN3 (1.1 mmol) in water, Cp*RuCl(PPh3)2 (5 mol %) was added at room temperature. To this mixture, alkyl halide (1.0 mmol) was added, and the reaction mixture was subjected to microwave irradiations at 250 W until total conversion of the starting alkyne (TLC). The crude mixture was extracted with EtOAc (3×30 mL). The organic layer was dried over $Na_2SO_4$. After the removal of solvent under reduced pressure, the resulting residue was purified by recrystallization from ethanol, to afford the desired products 8 and 9 in 90% and 92% yields, respectively [46,47].

Cu(I))-Catalyzed Multicomponent Huisgen 1,3-Dipolar Cycloaddition Reaction

To a suspension of the corresponding terminal alkyne (100 mg) and $NaN_3$ (1.1 mmol) in water (3 mL), the corresponding alkyl halide (1.0 mmol) was added, followed by the addition of the CuI catalyst (0.1 equiv) (FIG. 4). The reaction mixture was subjected to microwave irradiations at 250 W, which was completed within 4-6 min (TLC). The crude mixture was extracted with EtOAc (3×30 mL) and the combined organic layer was dried over sodium sulfate, concentrated under reduced pressure and purified through recrystallization from ethanol, to give pure 1,4-triazolyl derivatives 10-14 in 90-98% yields [48].

Multicomponent Synthesis of 3,5-Disubstituted Isoxazoles in Water Catalyzed by CuI At room temperature and stirring, to a mixture of alkyl derivatives 3 or 4 (0.1 g), $NH_2OH.HCl$ (1.2 equiv) and 0.1 equiv copper (I) iodide (CuI) in water, the appropriate aldehyde (1.1 equiv) was added, and the mixture was subjected to microwave irradiations at 250 W for 5-10 min (FIG. 5A). The crude mixture was diluted with water and then extracted with EtOAc (3×30 mL). The organic layer was dried over $Na_2SO_4$. After the removal of solvent in vacuo, the resulting residue was purified by recrystallization from ethanol, to obtain the desired products 15-17 in 98, 87 and 96% yield, respectively [49]. The spectral data of all the synthesized compounds are in agreement with the literature data [16-18,50].

Example 3

Molecular Docking Analysis

Molecular docking studies using MOE 2019.012 suite [51] were performed to propose the expected mechanism of action for the 17 tested compounds as SARS-CoV-2 Mpro inhibitors through evaluating their binding scores and interaction modes at the SARS-CoV-2 Mpro receptor active site. The co-crystallized native inhibitor (N3) was extracted from the protein complex and inserted in our calculations as a reference standard.

Preparation of the Selected Tested Compounds

Each member of the previously mentioned selected compounds 1-17 was sketched using the ChemDraw program, transferred to MOE, and then subjected to the preparation process for the docking step as described earlier [52]. Then, all the prepared compounds 1-17 were imported in one database together with the co-crystallized native inhibitor (N3, 18) and saved as an MDB file to be used during the docking procedure.

Preparation of the Active Site of the Applied SARS-CoV-2 Mproreceptor

The Protein Data Bank website was used to extract the X-ray structure of the SARS CoV-2 Mpro receptor (PDB ID: 6LU7) [53]. Then, all default steps for its preparation were run as described earlier in detail [54, 55].

Validation of the Applied MOE Program

Figure 29A:
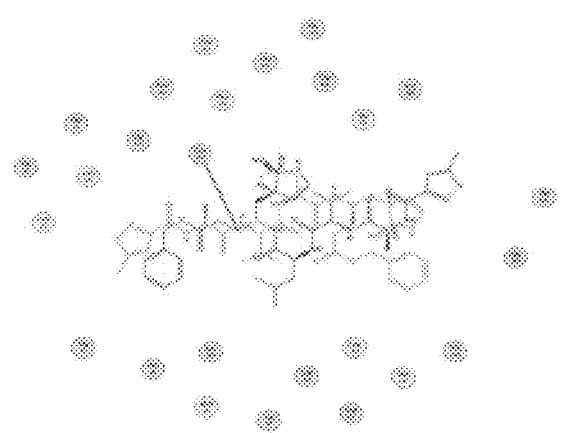
FIGS. 29A-B show a (A) 2D and (B) 3D representations of the redocking process between the native co-crystalized N3 inhibitor (red) and the docked compound (green).
Figure 29B:
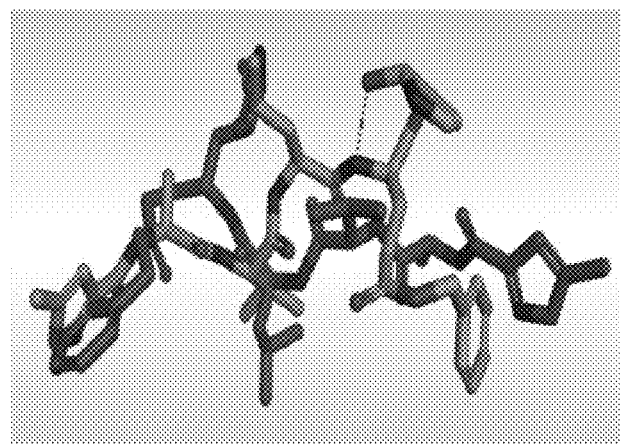
Figure 30A:
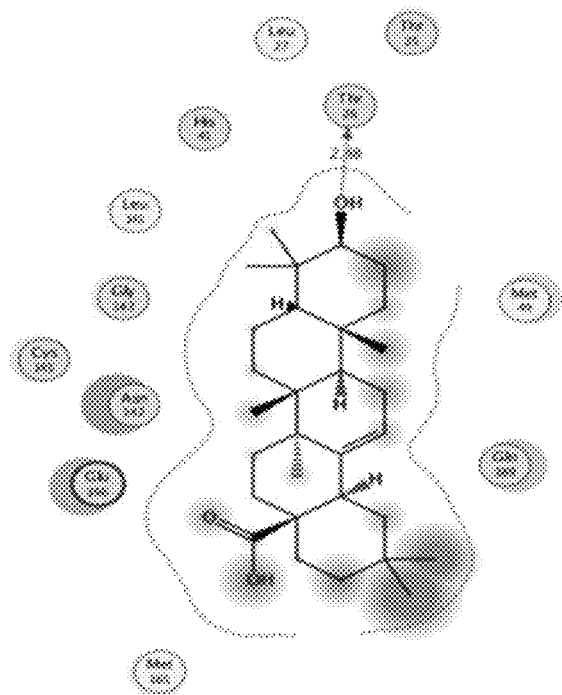
FIGS. 30A-B show a 2D representation of the binding interaction between (A) oleanolic acid or (B) maslinic acid at the N3-binding pocket in comparison to the docked N3 inhibitor.
Figure 30B:
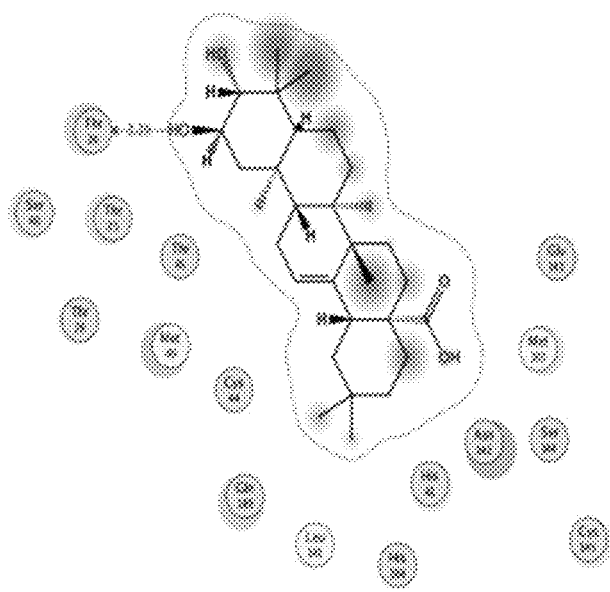
Figure 31A:
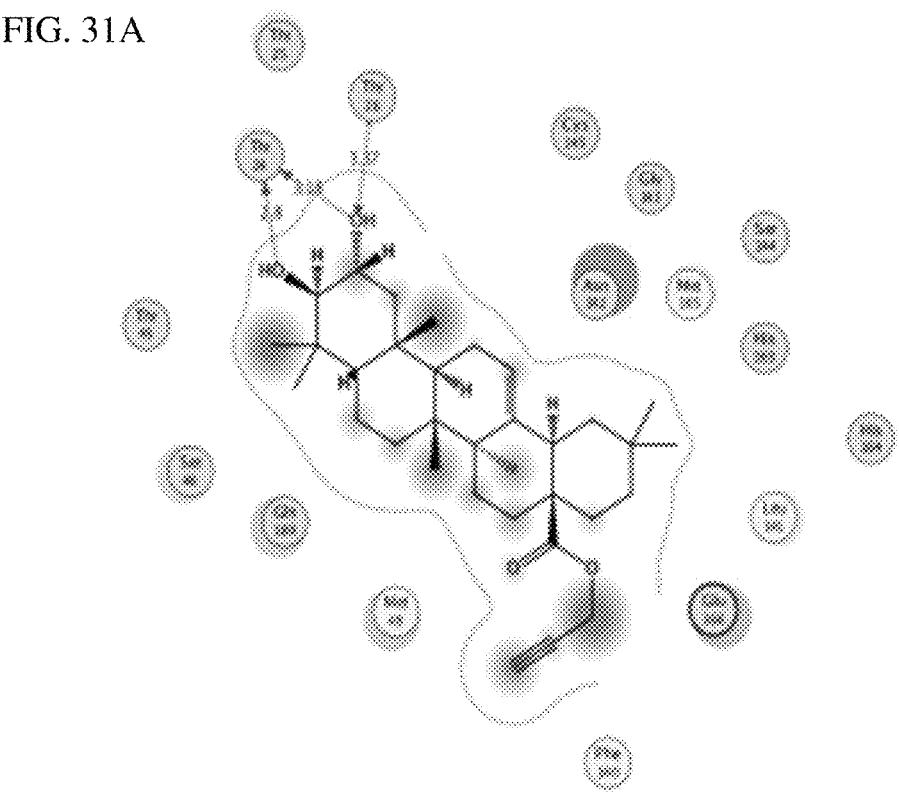
FIGS. 31A-B show a 2D representation of the binding interaction between (A) compound 3 or (B) compound 4 of the present disclosure at the N3-binding pocket in comparison to the docked N3 inhibitor.
Figure 31B:
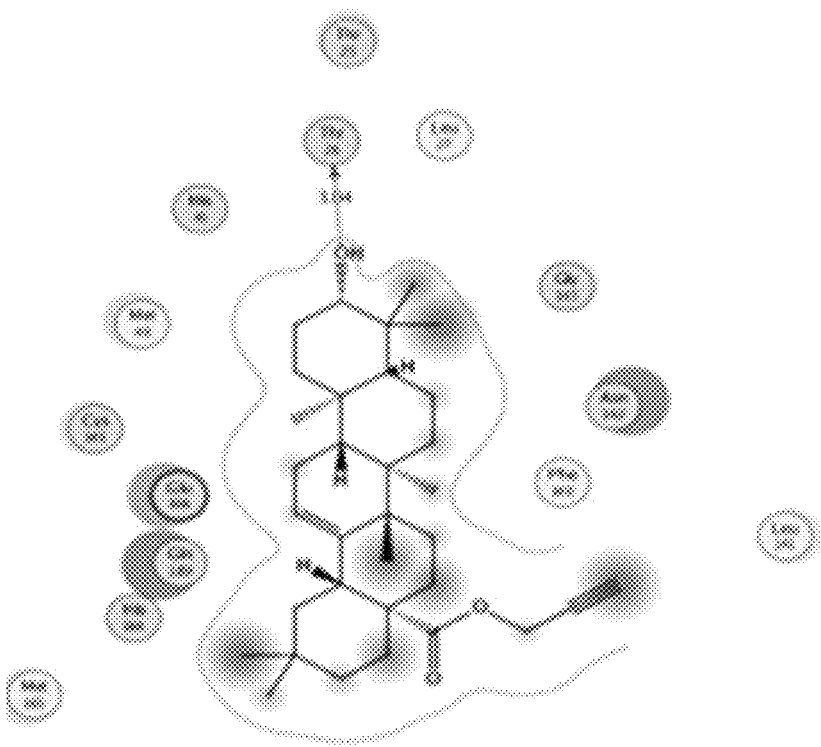
Figure 32A:
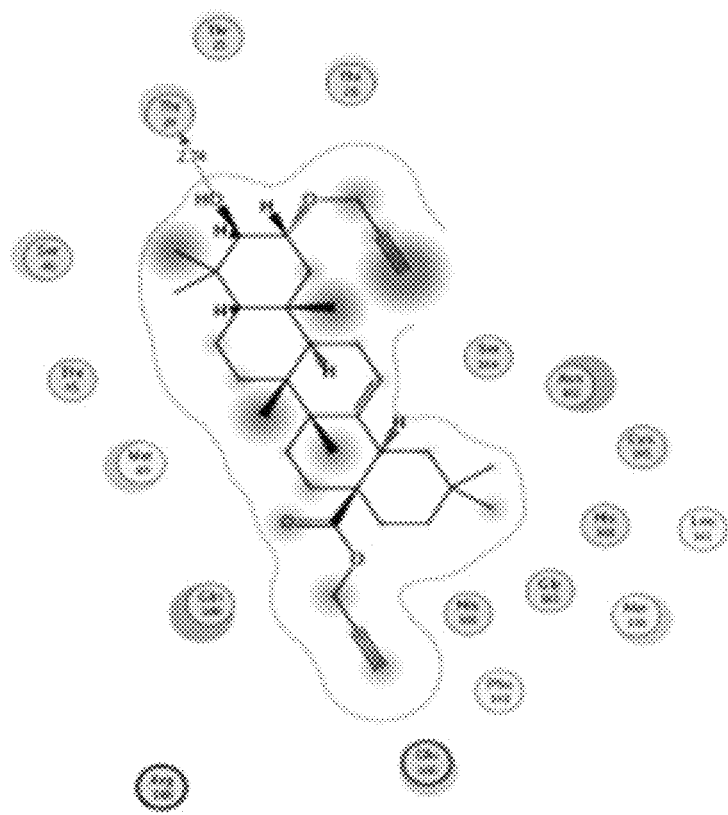
FIGS. 32A-B show a 2D representation of the binding interaction between (A) compound 5 or (B) compound 6 of the present disclosure at the N3-binding pocket in comparison to the docked N3 inhibitor.
Figure 32B:
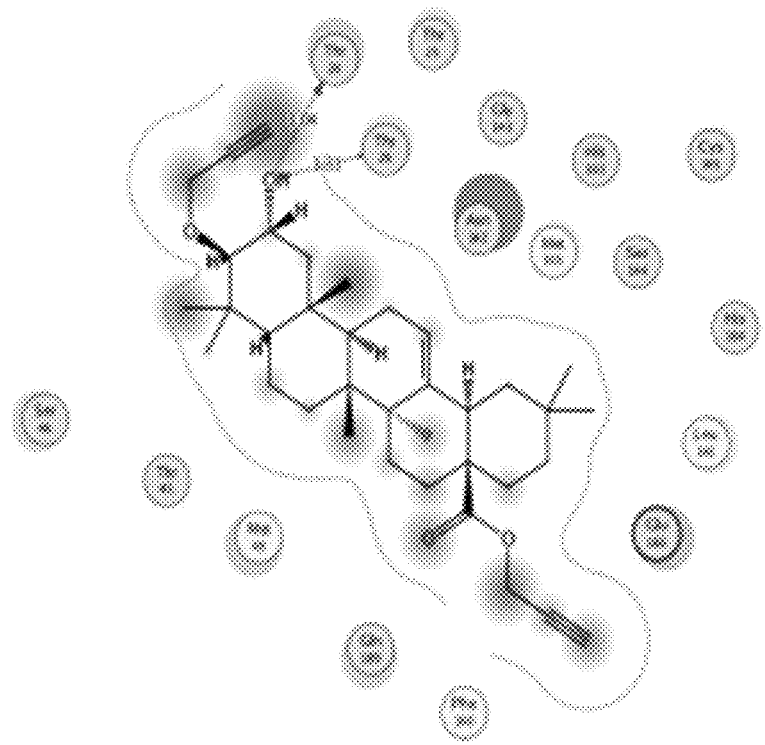
Figure 33A:
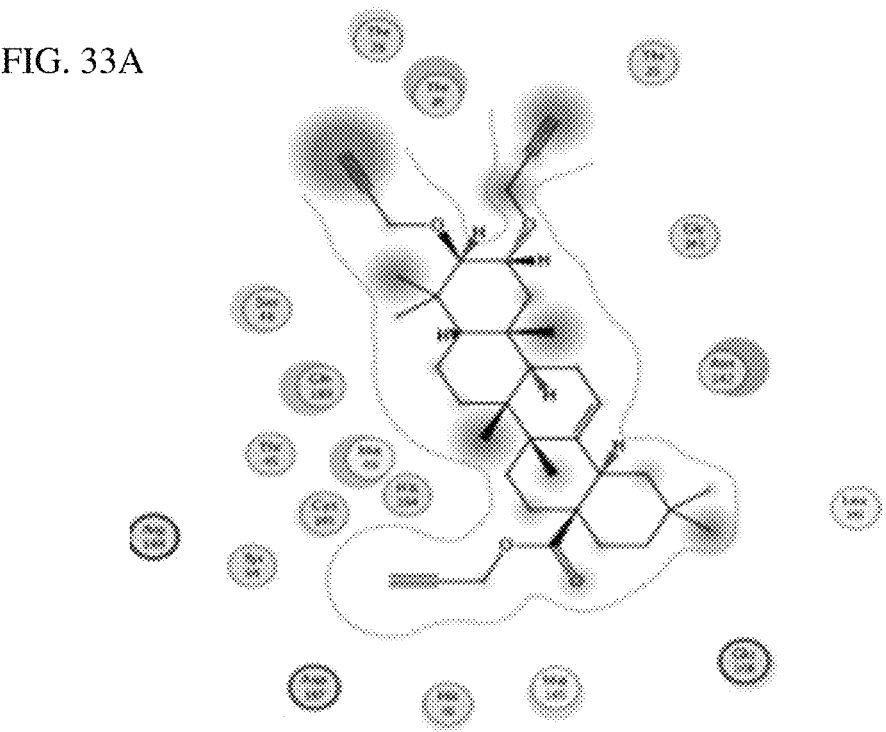
FIGS. 33A-B show a 2D representation of the binding interaction between (A) compound 7 or (B) compound 8 of the present disclosure at the N3-binding pocket in comparison to the docked N3 inhibitor.
Figure 33B:
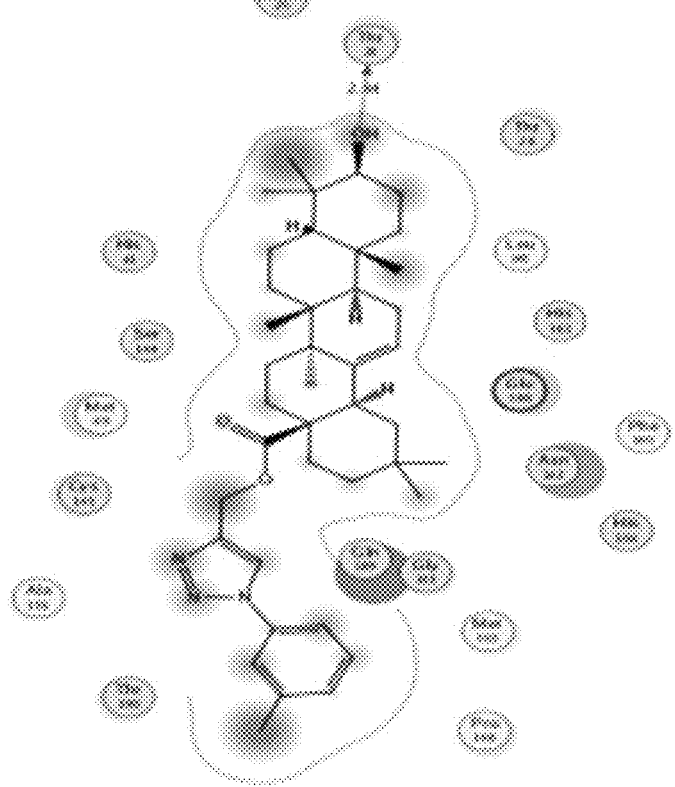
Figure 34A:
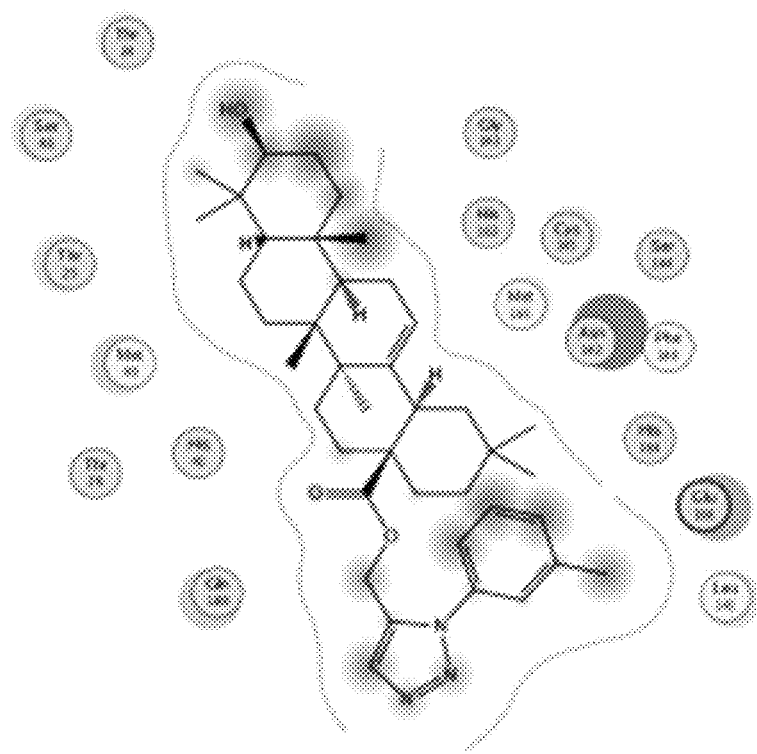
FIGS. 34A-B show a 2D representation of the binding interaction between (A) compound 9 or (B) compound 10 of the present disclosure at the N3-binding pocket in comparison to the docked N3 inhibitor.
Figure 34B:
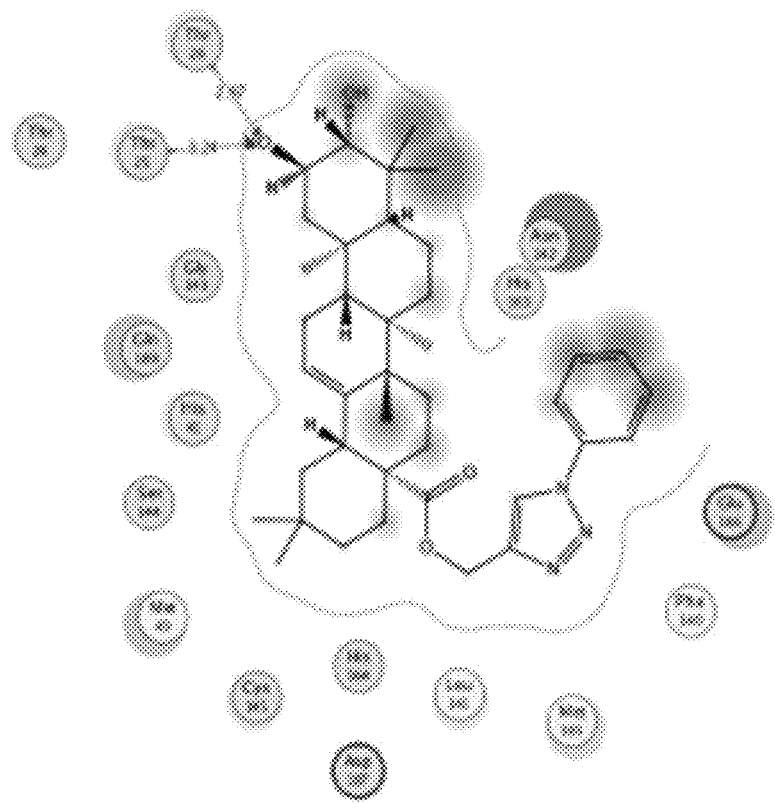
Figure 35A:
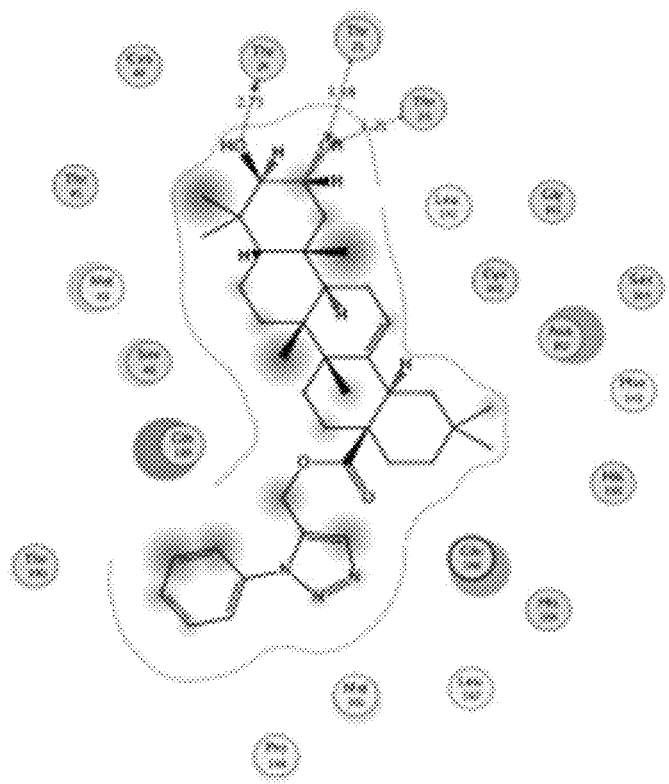
FIGS. 35A-B show a 2D representation of the binding interaction between (A) compound 11 or (B) compound 12 of the present disclosure at the N3-binding pocket in comparison to the docked N3 inhibitor.
Figure 35B:
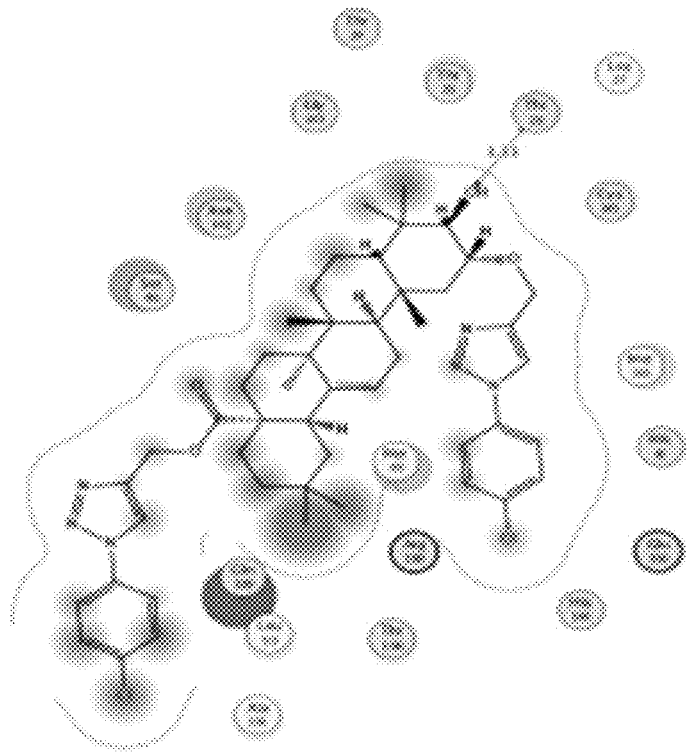
Figure 36A:
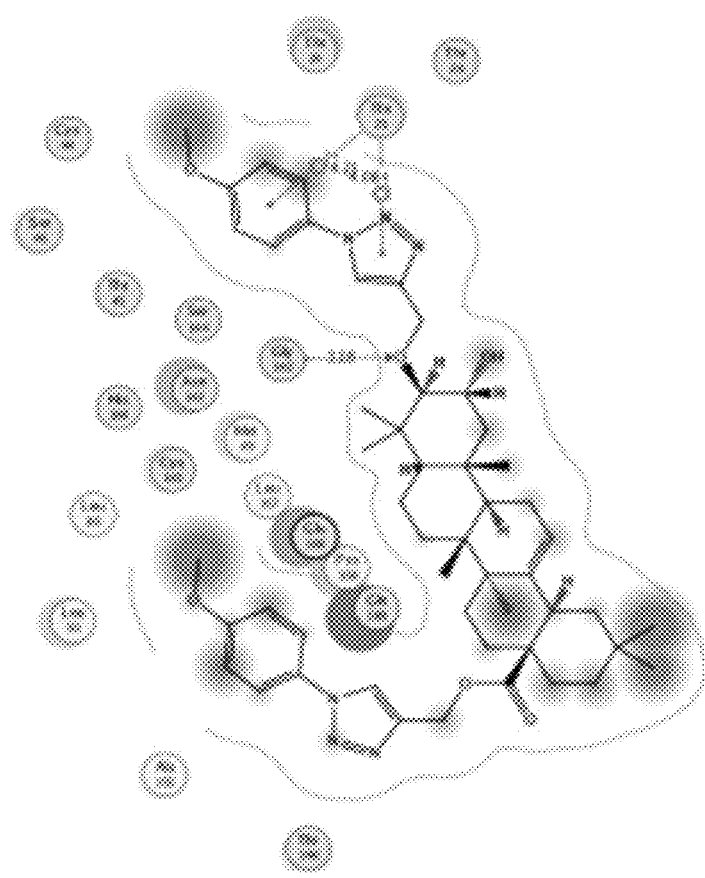
FIGS. 36A-B show a 2D representation of the binding interaction between (A) compound 13 or (B) compound 14 of the present disclosure at the N3-binding pocket in comparison to the docked N3 inhibitor.
Figure 36B:
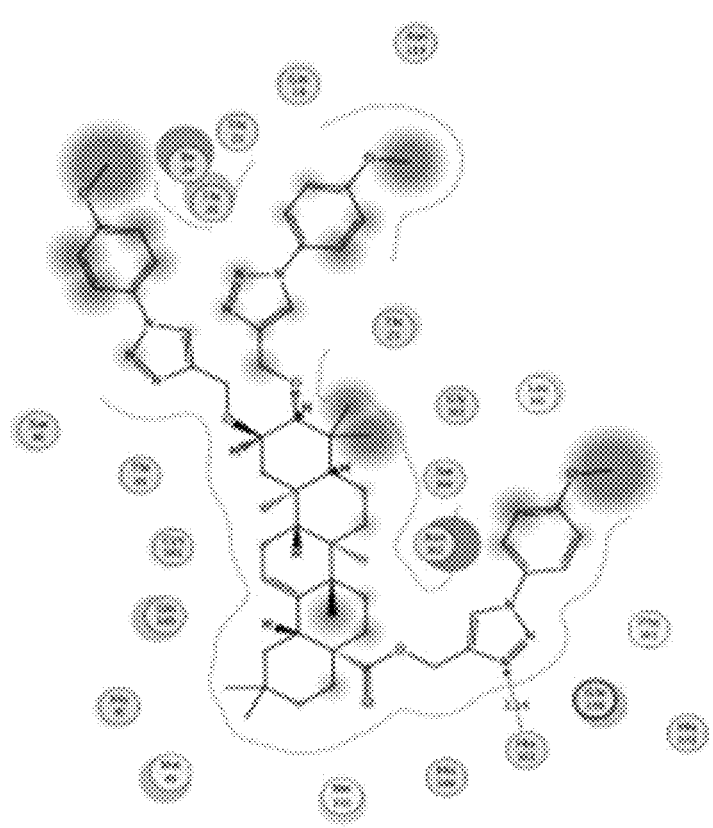
Figure 37A:
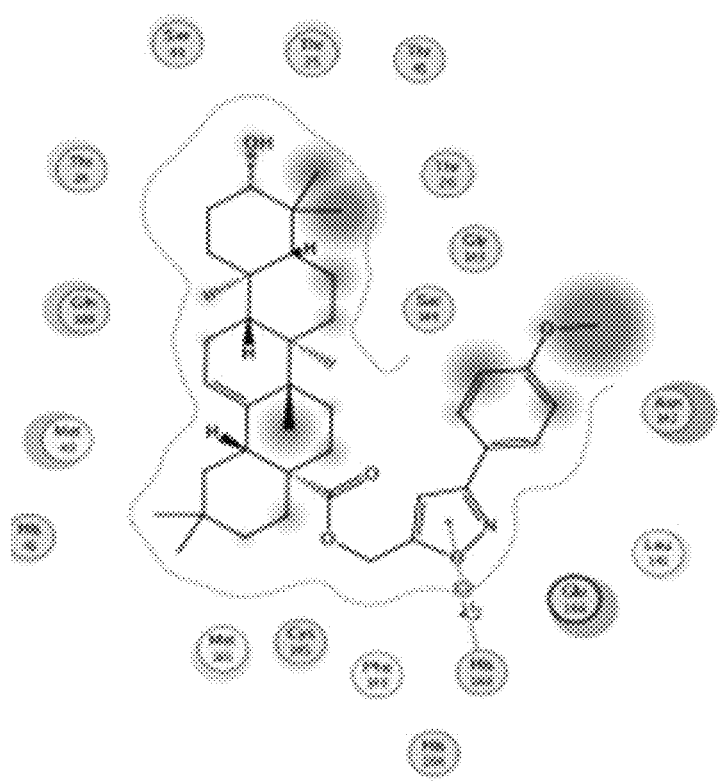
FIGS. 37A-B show a 2D representation of the binding interaction between (A) compound 15 or (B) compound 16 of the present disclosure at the N3-binding pocket in comparison to the docked N3 inhibitor.
Figure 37B:
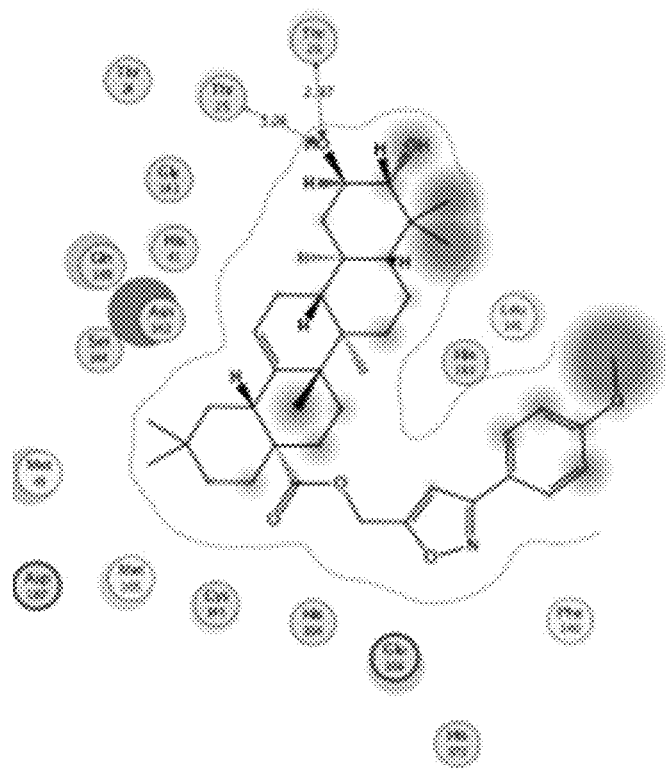
Figure 38A:
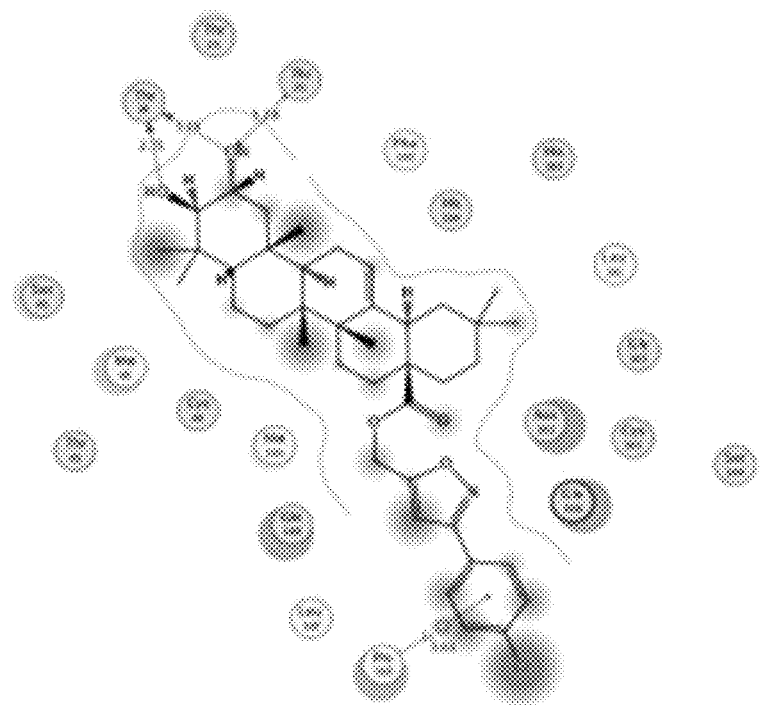
FIGS. 38A-B show a 2D representation of the binding interaction between (A) compound 17 of the present disclosure or (B) N3 inhibitor at the N3-binding pocket in comparison to the docked N3 inhibitor.
Figure 38B:
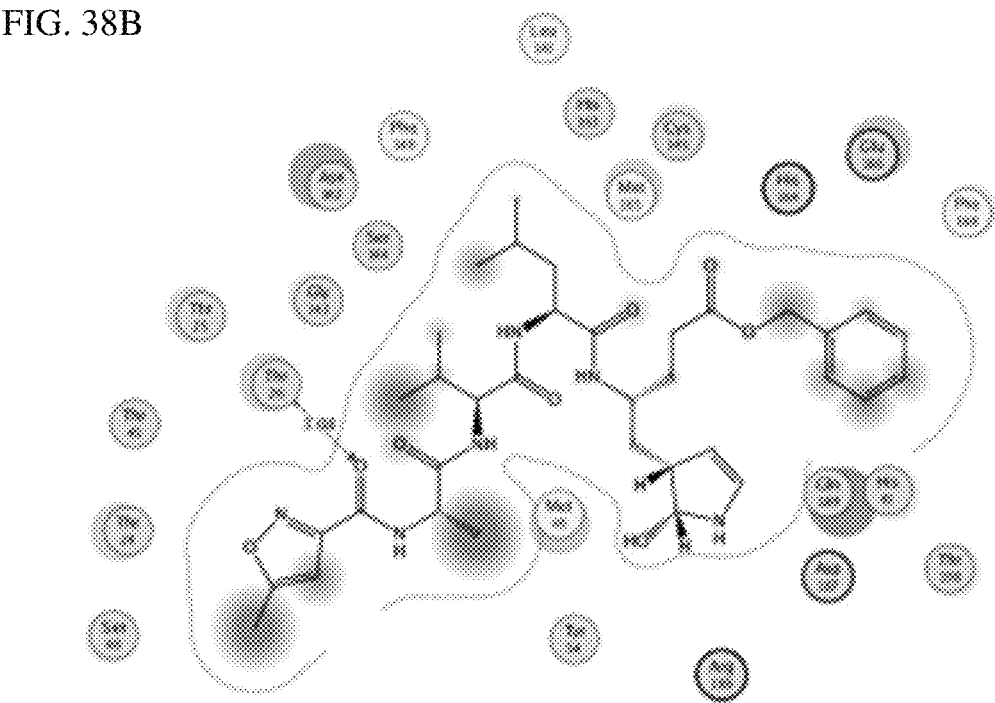

Before applying the docking process, we first performed a validation process for the prepared target SARS-CoV-2 Mpro receptor by redocking its co-crystallized native inhibitor (N3) inside its active site and comparing the resulted RMSD values between the co-crystallized (native) and docked N3 molecules. The obtained low RMSD value (1.20) indicated a promised valid performance (FIG. 29A-B) [56].

Docking of the Prepared Database to the Binding Pocket of SARS-CoV-2 Mpro Receptor The previously discussed database was selected and inserted at the site of ligand at the beginning of the general docking process and the default methodology was performed as described before [57]. Finally, we selected the best poses according to their binding scores, RMSD values, and binding modes for further considerations.

In Vitro Antiviral Bioassay

Cytotoxicity ($CC_{50}$) determination bioassay was performed as described below. To assess the half maximal cytotoxic concentration (COO, stock solutions of the test compounds were prepared in 10% DMSO in $ddH_2O$ and diluted further to the working solutions with DMEM. The cytotoxic activity of the extracts was tested in VERO-E6 cells by using crystal violet assay as previously described [58,59] with minor modifications. Briefly, the cells were seeded in 96-well plates (100 µL/well at a density of 3×105 cells/mL) and incubated for 24 h at 37° C. in a humidified 5% CO2 incubator. After 24 h, cells were treated with various concentrations of the tested compounds in triplicates. 72 hours later, the supernatant was discarded, and cell monolayers were fixed with 10% formaldehyde for 1 h at room temperature (RT). The fixed monolayers were then dried and stained with 50 µL of 0.1% crystal violet for 20 min on a bench rocker at RT. The monolayers were then washed, dried and the crystal violet dye in each well was then dissolved with 200 µL of methanol for 20 min on a bench rocker at RT. The absorbance of crystal violet solutions was measured at λmax 570 nm as a reference wavelength using a multiwell plate reader. Cytotoxic concentration 50% ($CC_{50}$) values were calculated using nonlinear regression analysis of GraphPad Prism software (version 5.01) by plotting log inhibitor versus normalized response (variable slope).

Inhibitory Concentration 50 ($IC_{50}$) Determination

The $IC_{50}$ values for the tested compounds were determined as previously described [2, 3], with minor modifications. Briefly, in 96-well tissue culture plates, 2.4×104 Vero-E6 cells were distributed in each well and incubated overnight at a humidified 37° C. incubator under 5% CO2 condition. The cell monolayers were then washed once with 1×PBS. An aliquot of the SARS-CoV-2 "NRC-03-nhCoV" virus [40] containing 100 TCID50 was incubated with serial diluted compounds and kept at 37° C. for 1 h. The Vero-E6 cells were treated with virus/compound mix and co-incubated at 37° C. in a total volume of 200 µL per well.

Untreated cells infected with virus represented the virus control; however, cells that were not treated and not infected were the cell control. Following incubation at 37° C. in 5% CO2 incubator for 72 h, the cells were fixed with 100 μL of 10% paraformaldehyde for 20 min and stained with 0.5% crystal violet in distilled water for 15 min at RT. The crystal violet dye was then dissolved using 100 μL of absolute methanol per well and the optical density of the color was measured at 570 nm using the Anthos Zenyth 200 rt plate reader (Anthos Labtec Instruments, Heerhugowaard, the Netherlands). The $IC_{50}$ of the compound refers to a concentration of the compound required to reduce the virus-induced cytopathic effect (CPE) by 50%, relative to the virus control.

Mechanism of Action(s) for Compound 17

To investigate whether the tested compound with high selectivity index and antiviral activity against NRC-03-nhCoV affect (a) viral adsorption, (b) viral replication or (c) viricidal effect, a plaque infectivity reduction assay was performed according to the following protocols:

(a) Viral Adsorption Mechanism

The viral adsorption mechanism was assayed according to a protocol by Zhang et al. [60] with modifications. Vero-E6 cells were cultivated in a 6-well plate (105 cells/mL) for 24 h at 37° C. Each tested drug was applied in 500 μL of medium without supplements and co-incubated with the cells for 2 h at 4° C. The non-absorbed drug in the applied inocula was removed by washing cells three times with 1×PBS. The NRC-03-nhCoV was diluted to a countable range "10-4" and co-incubated with the pretreated cells. About 1 h post-incubation, the inocula were removed and 3 mL of agarose overlay (1:1 mixture of warmed 2× plaque media and a stock solution of heated 2% agarose) were added. The plates were kept at room temperature to solidify and then incubated at 37° C. to allow the formation of viral plaques. The plaques were fixed using 10% formaldehyde, stained using crystal violet (1% crystal violet in 20% ethanol and distilled H2O), washed with rinse water and dried to calculate the percentage reduction in plaque formation compared to control wells, which comprised untreated Vero-E6 cells directly infected with NRC-03-nhCoV.

(b) Viral Replication Mechanism

The impact of the tested drug on viral replication was determined as previously described [50]. Vero-E6 cells were cultivated in a 6-well plate (105 cell/mL) for 24 h at 37° C. The NRC-03-nhCoV of the countable range was inoculated directly to the cells and incubated for 1 h at 37° C. The inocula containing the non-adsorbed virus were removed by washing the infected cell monolayers three times with 1×PBS. The analyzed compound was then applied in varying concentrations to infected cells for another 1 h contact time at 37° C. After removing the inocula containing the tested drug, agarose overlay was added to the cells. The plates were kept at room temperature to solidify and then incubated at 37° C. to allow the formation of viral plaques. The plaques were fixed using 10% formaldehyde, stained using 1% crystal violet washed with rinse water and dried to calculate the percentage reduction in plaque formation compared to control wells, which comprised untreated Vero-E6 cells directly infected with NRC-03-nhCoV.

I Virucidal Mechanism

The virucidal mechanism was analyzed [61]. Briefly, Vero-E6 cells (105 cells/mL) were cultivated for 24 h at 37° C. in a 6-well plate. In an imonium, 200 μL of stock NRC-03-nhCoV were mixed with the tested compound at different concentrations. The mixture was kept for 1 h at room temperature against the control untreated virus. After 1 h of incubation, the mixture was ten-fold serial diluted four times using serum-free medium to obtain a countable range of the virus. An aliquot of 100 μL of each dilution were added to the Vero-E6 cell monolayer. After 1 h contact time, the agarose overlay was added to the cell monolayer. The plates were kept at room temperature to solidify and then incubated at 37° C. to allow the formation of viral plaques. The plaques were fixed using 10% formaldehyde, stained using 1% crystal violet washed with rinse water and dried to calculate the percentage reduction in plaque formation compared to control wells, which comprised untreated Vero-E6 cells directly infected with NRC-03-nhCoV.

Oleanolic acid 1 and maslinic acid 2, isolated from pomace olive oil, and a series of their synthesized structural analogues 3-17 were first evaluated using molecular docking for their proposed expected inhibitory activities against SARS-CoV-2 main protease, and then were screened for the same activity. Most of the tested compounds showed promising affinities towards SARS-CoV-2 main protease, especially for the most active member 17. Accordingly, we recommend such compounds for more advanced in vitro and in vivo studies to obtain an effective therapeutic against the pandemic SARS-CoV-2. Moreover, the aforementioned studied compounds could be used alone or in combinations for treating SARS-CoV-2 infection.

REFERENCES

1. Kumar, S.; Singh, R.; Kumari, N.; Karmakar, S.; Behera, M.; Siddiqui, A. J.; Rajput, V. D.; Minkina, T.; Bauddh, K.; Kumar, N. Current understanding of the influence of environmental factors on sars-cov-2 transmission, persistence, and infectivity. *Environmental science and pollution research international* 2021, 28, 6267-6288.
2. Mostafa, A.; Kandeil, A.; Y, A. M. M. E.; Kutkat, O.; Moatasim, Y.; Rashad, A. A.; Shehata, M.; Gomaa, M. R.; Mahrous, N.; Mahmoud, S. H., et al. Fda-approved drugs with potent in vitro antiviral activity against severe acute respiratory syndrome coronavirus 2. *Pharmaceuticals* 2020, 13.
3. Alnajjar, R.; Mostafa, A.; Kandeil, A.; Al-Karmalawy, A. A. Molecular docking, molecular dynamics, and in vitro studies reveal the potential of angiotensin ii receptor blockers to inhibit the covid-19 main protease. *Heliyon* 2020, 6, e05641.
4. Mahmoud, D. B.; Shitu, Z.; Mostafa, A. Drug repurposing of nitazoxanide: Can it be an effective therapy for covid-19? *J Genet Eng Biotechnol* 2020, 18, 35-35.
5. Surti, M.; Patel, M.; Adnan, M.; Moin, A.; Ashraf, S. A.; Siddiqui, A. J.; Snoussi, M.; Deshpande, S.; Reddy, M. N. Ilimaquinone (marine sponge metabolite) as a novel inhibitor of sars-cov-2 key target proteins in comparison with suggested covid-19 drugs: Designing, docking and molecular dynamics simulation study. *RSC Advances* 2020, 10, 37707-37720.
6. Alzahrani, F. A.; Saadeldin, I. M.; Ahmad, A.; Kumar, D.; Azhar, E. I.; Siddiqui, A. J.; Kurdi, B.; Sajini, A.; Alrefaei, A. F.; Jahan, S. The potential use of mesenchymal stem cells and their derived exosomes as immunomodulatory agents for covid-19 patients. *Stem Cells International* 2020, 2020, 8835986.
7. Fayed, M. A. A.; El-Behairy, M. F.; Abdallah, I. A.; Abdel-Bar, H. M.; Elimam, H.; Mostafa, A.; Moatasim, Y.; Abouzid, K. A. M.; Elshaier, Y. A. M. M. Structure- and ligand-based in silico studies towards the repurposing of marine bioactive compounds to target sars-cov-2. *Arabian Journal of Chemistry* 2021, 14, 103092-103092.

8. Xu, R.; Fazio, G. C.; Matsuda, S. P. T. On the origins of triterpenoid skeletal diversity. *Phytochemistry* 2004, 65, 261-291.
9. Bruneton, J. *Pharmacognosie, phytochimie, plantes medicinales*. Technique et Documentation Lavoisier: Paris, France, 1999.
10. Muffler, K.; Leipold, D.; Scheller, M.-C.; Haas, C.; Steingroewer, J.; Bley, T.; Neuhaus, H. E.; Mirata, M. A.; Schrader, J.; Ulber, R. Biotransformation of triterpenes. *Process Biochemistry* 2011, 46, 1-15.
11. Hisham Shady, N.; Youssif, K. A.; Sayed, A. M.; Belbahri, L.; Oszako, T.; Hassan, H. M.; Abdelmohsen, U. R. Sterols and triterpenes: Antiviral potential supported by in-silico analysis. *Plants* 2021, 10, 41.
12. Dzubak, P.; Hajduch, M.; Vydra, D.; Hustova, A.; Kvasnica, M.; Biedermann, D.; Markova, L.; Urban, M.; Sarek, J. Pharmacological activities of natural triterpenoids and their therapeutic implications. *Natural product reports* 2006, 23, 394-411.
13. Sparg, S. G.; Light, M. E.; van Staden, J. Biological activities and distribution of plant saponins. *Journal of Ethnopharmacology* 2004, 94, 219-243.
14. Cheng, K.; Liu, J.; Liu, X.; Li, H.; Sun, H.; Xie, J. Synthesis of glucoconjugates of oleanolic acid as inhibitors of glycogen phosphorylase. *Carbohydrate research* 2009, 344, 841-850.
15. Chouaib, K.; Hichri, F.; Nguir, A.; Daami-Remadi, M.; Elie, N.; Touboul, D.; Ben Jannet, H.; Hamza, M. A. Semi-synthesis of new antimicrobial esters from the natural oleanolic and maslinic acids. *Food chemistry* 2015, 183, 8-17.
16. Chouaib, K.; Delemasure, S.; Dutartre, P.; Jannet, H. B. Microwave-assisted synthesis, anti-inflammatory and antiproliferative activities of new maslinic acid derivatives bearing 1,5- and 1,4-disubstituted triazoles. *Journal of Enzyme Inhibition and Medicinal Chemistry* 2016, 31, 130-147.
17. Chouaib, K.; Romdhane, A.; Delemasure, S.; Dutartre, P.; Elie, N.; Touboul, D.; Ben jannet, H.; Ali Hamza, M. h. Regiospecific synthesis, anti-inflammatory and anticancer evaluation of novel 3,5-disubstituted isoxazoles from the natural maslinic and oleanolic acids. *Industrial Crops and Products* 2016, 85, 287-299.
18. 20 18. Chouaib, K.; Romdhane, A.; Delemasure, S.; Dutartre, P.; Elie, N.; Touboul, D.; Ben Jannet, H. Regiospecific synthesis by copper- and ruthenium-catalyzed azide-alkyne 1,3-dipolar cycloaddition, anticancer and anti-inflammatory activities of oleanolic acid triazole derivatives. *Arabian Journal of Chemistry* 2019, 12, 3732-3742.
19. Chen, P.; Zeng, H.; Wang, Y.; Fan, X.; Xu, C.; Deng, R.; Zhou, X.; Bi, H.; Huang, M. Low dose of oleanolic acid protects against lithocholic acid-induced cholestasis in mice: Potential involvement of nuclear factor-e2-related factor 2-mediated upregulation of multidrug resistance-associated proteins. *Drug metabolism and disposition: the biological fate of chemicals* 2014,
20. 42, 844-852.
21. Sheng, H.; Sun, H. Synthesis, biology and clinical significance of pentacyclic triterpenes: A multi-target approach to prevention and treatment of metabolic and vascular diseases. *Natural product reports* 2011, 28, 543-593.
22. Chen, D.-F.; Zhang, S.-X.; Wang, H.-K.; Zhang, S.-Y.; Sun, Q.-Z.; Cosentino, L. M.; Lee, K.-H. Novel anti-hiv lancilactone c and related triterpenes from kadsura lancilimba. *Journal of Natural Products* 1999, 62, 94-97.
23. Kashiwada, Y.; Wang, H. K.; Nagao, T.; Kitanaka, S.; Yasuda, I.; Fujioka, T.; Yamagishi, T.; Cosentino, L. M.; Kozuka, M.; Okabe, H., et al. Anti-aids agents. 30. Anti-hiv activity of oleanolic acid, pomolic acid, and structurally related triterpenoids. *J Nat Prod* 1998, 61, 1090-1095.
24. Zhu, Y. M.; Shen, J. K.; Wang, H. K.; Cosentino, L. M.; Lee, K. H. Synthesis and anti-hiv activity of oleanolic acid derivatives. *Bioorganic & medicinal chemistry letters* 2001, 11, 3115-3118.
25. Shanmugam, M. K.; Dai, X.; Kumar, A. P.; Tan, B. K.; Sethi, G.; Bishayee, A. Oleanolic acid and its synthetic derivatives for the prevention and therapy of cancer: Preclinical and clinical evidence. *Cancer letters* 2014, 346, 206-216.
26. Hichri, F.; Jannet, H. B.; Cheriaa, J.; Jegham, S.; Mighri, Z. Antibacterial activities of a few prepared derivatives of oleanolic acid and of other natural triterpenic compounds. *Comptes Rendus Chimie* 2003, 6, 473-483.
27. Tsuji, M.; Sriwilaijaroen, N.; Inoue, H.; Miki, K.; Kinoshita, K.; Koyama, K.; Furuhata, K.; Suzuki, Y.; Takahashi, K. Synthesis and anti-influenza virus evaluation of triterpene-sialic acid conjugates. *Bioorganic & Medicinal Chemistry* 2018, 26, 17-24.
28. Blanco-Cabra, N.; Vega-Granados, K.; Moya-Anderico, L.; Vukomanovic, M.; Parra, A.; Alvarez de Cienfuegos, L.; Torrents, E. Novel oleanolic and maslinic acid derivatives as a promising treatment against bacterial biofilm in nosocomial infections: An in vitro and in vivo study. *ACS Infectious Diseases* 2019, 5, 1581-1589.
29. Wen, X.; Zhang, P.; Liu, J.; Zhang, L.; Wu, X.; Ni, P.; Sun, H. Pentacyclic triterpenes. Part 2: Synthesis and biological evaluation of maslinic acid derivatives as glycogen phosphorylase inhibitors. *Bioorganic & medicinal chemistry letters* 2006, 16, 722-726.
30. Qiu, W.-W.; Shen, Q.; Yang, F.; Wang, B.; Zou, H.; Li, J.-Y.; Li, J.; Tang, J. Synthesis and biological evaluation of heterocyclic ring-substituted maslinic acid derivatives as novel inhibitors of protein tyrosine phosphatase 1b. *Bioorganic & medicinal chemistry letters* 2009, 19, 6618-6622.
31. Taniguchi, S.; Imayoshi, Y.; Kobayashi, E.; Takamatsu, Y.; Ito, H.; Hatano, T.; Sakagami, H.; Tokuda, H.; Nishino, H.; Sugita, D., et al. Production of bioactive triterpenes by imoniuma japonica calli. *Phytochemistry* 2002, 59, 315-323.
32. Parra, A.; Rivas, F.; Lopez, P. E.; Garcia-Granados, A.; Martinez, A.; Albericio, F.; Marquez, N.; Munoz, E. Solution- and solid-phase synthesis and anti-hiv activity of maslinic acid derivatives containing amino acids and peptides. *Bioorganic & Medicinal Chemistry* 2009, 17, 1139-1145.
33. Agrawal, N.; Mishra, P. The synthetic and therapeutic expedition of isoxazole and its analogs. *Medicinal Chemistry Research* 2018, 27, 1309-1344.
34. Konya, B.; Docsa, T.; Gergely, P.; Somsak, L. Synthesis of heterocyclic n-(β-d-glucopyranosyl) carboxamides for inhibition of glycogen phosphorylase. *Carbohydrate research* 2012, 351, 56-63.
35. Koufaki, M.; Tsatsaroni, A.; Alexi, X.; Guerrand, H.; Zerva, S.; Alexis, M. N. Isoxazole substituted chromans against oxidative stress-induced neuronal damage. *Bioorg Med Chem* 2011, 19, 4841-4850.
36. Filali, I.; Romdhane, A.; Znati, M.; Jannet, H. B.; Bouajila, J. Synthesis of new harmine isoxazoles and evaluation of their potential anti-alzheimer, anti-inflam- 36. matory, and anticancer activities. *Medicinal chemistry (Shariqah (United Arab Emirates))* 2016, 12, 184-190.
37. Agalave, S. G.; Maujan, S. R.; Pore, V. S. Click chemistry: 1,2,3-triazoles as pharmacophores. *Chemistry, an Asian journal* 2011, 6, 2696-2718.
38. Gonzaga, D. T. G.; Souza, T. M. L.; Andrade, V. M. M.; Ferreira, V. F.; de, C. d. S. F. Identification of 1-aryl-1h-1,2,3-triazoles as potential new antiretroviral agents. *Medicinal chemistry (Shariqah (United Arab Emirates))* 2018, 14, 242-248.
39. El-Sebaey, S. A. Recent advances in 1,2,4-triazole scaffolds as antiviral agents. *ChemistrySelect* 2020, 5, 11654-11680.
40. Wang, X. L.; Wan, K.; Zhou, C. H. Synthesis of novel sulfanilamide-derived 1,2,3-triazoles and their evaluation for antibacterial and antifungal activities. *European journal of medicinal chemistry* 2010, 45, 4631-4639.
41. Kandeil, A.; Mostafa, A.; El-Shesheny, R.; Shehata, M.; Roshdy, W. H.; Ahmed, S. S.; Gomaa, M.; Taweel, A. E.; Kayed, A. E.; Mahmoud, S. H., et al. Coding-complete genome sequences of two sars-cov-2 isolates from imon. *Microbiology Resource Announcements* 2020, 9, e00489-00420.
42. Guinda, A.; Rada, M.; Delgado, T.; Gutierrez-Adanez, P.; Castellano, J. M. Pentacyclic triterpenoids from olive fruit and leaf. *Journal of agricultural and food chemistry* 2010, 58, 9685-9691.
43. Gil, M.; Haidour, A.; Ramos, J. L. Identification of two triterpenoids in solid wastes from olive cake. *Journal of agricultural and food chemistry* 1997, 45, 4490-4494.
44. Romero, C.; Garcia, A.; Medina, E.; Ruiz-Mendez, M. V.; Castro, A. d.; Brenes, M. Triterpenic acids in table olives. *Food Chemistry* 2010, 118, 670-674.
45. Goulas, V.; Manganaris, G. A. Towards an efficient protocol for the determination of triterpenic acids in olive fruit: A comparative study of drying and extraction methods. *Phytochemical Analysis* 2012, 23, 444-449.
46. Chan, R. W. Y.; Hemida, M. G.; Kayali, G.; Chu, D. K. W.; Poon, L. L. M.; Alnaeem, A.; Ali, M. A.; Tao, K. P.; Ng, H. Y.; Chan, M. C. W., et al. Tropism and replication of middle east respiratory syndrome coronavirus from dromedary camels in the human respiratory tract: An in-vitro and ex-vivo study. *The Lancet Respiratory Medicine* 2014, 2, 813-822.
47. Oakdale, J. S.; Fokin, V. V.; Umezaki, S.; Fukuyama, T. Preparation of 1,5-disubstituted 1,2,3-triazoles via rutheniumcatalyzed azide alkyne cycloaddition. *Organic Synth* 2013, 90, 96-104.
48. Takasu, K.; Azuma, T.; Takemoto, Y. Synthesis of trifunctional thioureas bearing 1,5-disubstituted triazole tether by rucatalyzed huisgen cycloaddition. *Tetrahedron Letters* 2010, 51, 2737-2740.
49. Nador, F.; Volpe, M. A.; Alonso, F.; Feldhoff, A.; Kirschning, A.; Radivoy, G. Copper nanoparticles supported on silica coated maghemite as versatile, magnetically recoverable and reusable catalyst for alkyne coupling and cycloaddition reactions. *Applied Catalysis A: General* 2013, 455, 39-45.
50. Hansen, T. V.; Wu, P.; Fokin, V. V. One-pot copper(i)-catalyzed synthesis of 3,5-disubstituted isoxazoles. *The Journal of Organic Chemistry* 2005, 70, 7761-7764.
51. Kuo, Y. C.; Lin, L. C.; Tsai, W. J.; Chou, C. J.; Kung, S. H.; Ho, Y. H. Samarangenin b from imonium sinense suppresses herpes simplex virus type 1 replication in vero cells by regulation of viral macromolecular synthesis. *Antimicrobial agents and chemotherapy* 2002, 46, 2854-2864.
52. Vilar, S.; Cozza, G.; Moro, S. Medicinal chemistry and the molecular operating environment (moe): Application of qsar and molecular docking to drug discovery. *Current topics in medicinal chemistry* 2008, 8, 1555-1572.
53. Al-Karmalawy, A. A.; Khattab, M. Molecular modelling of mebendazole polymorphs as a potential colchicine binding site inhibitor. *New Journal of Chemistry* 2020, 44, 13990-13996.
54. Jin, Z.; Du, X.; Xu, Y.; Deng, Y.; Liu, M.; Zhao, Y.; Zhang, B.; Li, X.; Zhang, L.; Peng, C., et al. Structure of mpro from sarscov-2 and discovery of its inhibitors. *Nature* 2020, 582, 289-293.
55. Ghanem, A.; Emara, H. A.; Muawia, S.; Abd El Maksoud, A. I.; Al-Karmalawy, A. A.; Elshal, M. F. Tanshinone iia synergistically enhances the antitumor activity of doxorubicin by interfering with the pi3k/akt/mtor pathway and inhibition of topoisomerase ii: In vitro and molecular docking studies. *New Journal of Chemistry* 2020, 44, 17374-17381.
56. Khattab, M.; Al-Karmalawy, A. Revisiting activity of some nocodazole analogues as a potential anticancer drugs using molecular docking and dft calculations. *Frontiers in Chemistry* 2021.
57. McConkey, B. J.; Sobolev, V.; Edelman, M. The performance of current methods in ligand-protein docking. *Current Science* 2002, 83, 845-856.
58. Eliaa, S. G.; Al-Karmalawy, A. A.; Saleh, R. M.; Elshal, M. F. Empagliflozin and doxorubicin synergistically inhibit the survival of triple-negative breast cancer cells via interfering with the mtor pathway and inhibition of calmodulin: In vitro and molecular docking studies. *ACS Pharmacology & Translational Science* 2020, 3, 1330-1338.
59. Al-Rabia, M. W.; Alhakamy, N. A.; Ahmed, O. A. A.; Eljaaly, K.; Aloafi, A. L.; Mostafa, A.; Asfour, H. Z.; Aldarmahi, A. A.;
60. Darwish, K. M.; Ibrahim, T. S., et al. Repurposing of sitagliptin-melittin optimized nanoformula against sars-cov-2; antiviral screening and molecular docking studies. *Pharmaceutics* 2021, 13, 307.
61. 59. Feoktistova, M.; Geserick, P.; Leverkus, M. Crystal violet assay for determining viability of cultured cells. *Cold Spring Harbor protocols* 2016, 2016, pdb-.prot087379.
62. 60. Zhang, J.; Zhan, B.; Yao, X.; Gao, Y.; Shong, J. [antiviral activity of tannin from the pericarp of punica granatum 1. Against genital herpes virus in vitro]. *Zhongguo Zhong yao za zhi=Zhongguo zhongyao zazhi=China journal of Chinese materia medica* 1995, 20, 556-558, 576, inside backcover.
63. 61. Schuhmacher, A.; Reichling, J.; Schnitzler, P. Virucidal effect of peppermint oil on the enveloped viruses herpes simplex virus type 1 and type 2 in vitro. *Phytomedicine: international journal of phytotherapy and phytopharmacology* 2003, 10, 504-510.

It is to be understood that this invention is not limited to any particular embodiment described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

What is claimed is:

1. A method of treating SARS-CoV-2 infection in a subject in need thereof, comprising the step of: administering a SARS-CoV-2 therapeutic composition to the subject in an amount sufficient to treat the infection, wherein the SARS-CoV-2 therapeutic composition comprises at least one triterpenoid selected from the group of triterpenoids 3-17 and pharmacologically acceptable salts thereof, wherein the triterpenoid 3 has the chemical structure of Formula III;

Formula III wherein the triterpenoid 4 has the chemical structure of Formula IV;

Formula IV wherein the triterpenoid 5 has the chemical structure of Formula V;

Formula V wherein the triterpenoid 6 has the chemical structure of Formula VI;

Formula VI wherein the triterpenoid 7 has the chemical structure of Formula VII;

wherein the triterpenoid 8 has the chemical structure of Formula VIII;

wherein the triterpenoid 9 has the chemical structure of Formula IX;

wherein the triterpenoid 10 has the chemical structure of Formula X;

wherein the triterpenoid 11 has the chemical structure of Formula XI;

wherein the triterpenoid 12 has the chemical structure of Formula XII;

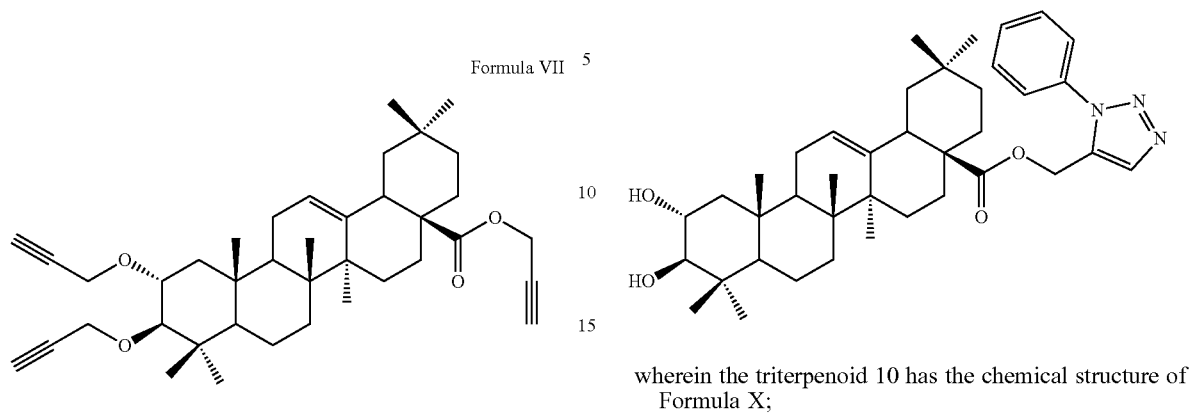

wherein the triterpenoid 13 has the chemical structure of Formula XIII;

wherein the triterpenoid 14 has the chemical structure of Formula XIV;

wherein the triterpenoid 15 has the chemical structure of Formula XV;

wherein the triterpenoid 16 has the chemical structure of Formula XVI;

wherein the triterpenoid 17 has the chemical structure of Formula XVII.

2. The method of claim 1, wherein the composition comprises a combination of two or more of the at least one triterpenoid selected from the group of triterpenoids having a chemical structure as set forth in Formulas III-XVII.

3. A method of inhibiting SARS-CoV 2 growth, comprising:

contacting SARS-CoV 2 particles with a composition comprising a compound selected from the group consisting of triterpenoids 3-17 and pharmacologically acceptable salts thereof, wherein the compound is used in an amount sufficient to inhibit the SARS-CoV-2 growth, wherein the triterpenoid 3 has the chemical structure of Formula Formula III

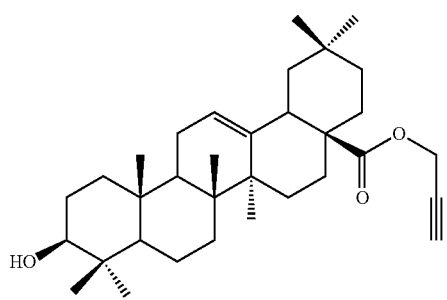

wherein the triterpenoid 4 has the chemical structure of Formula IV;

Formula IV

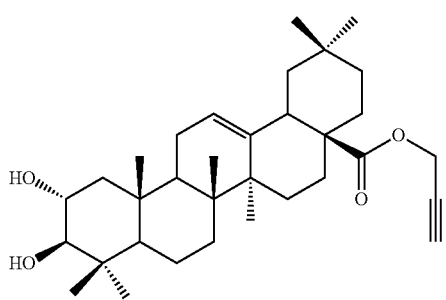

wherein the triterpenoid 5 has the chemical structure of Formula V;

Formula V

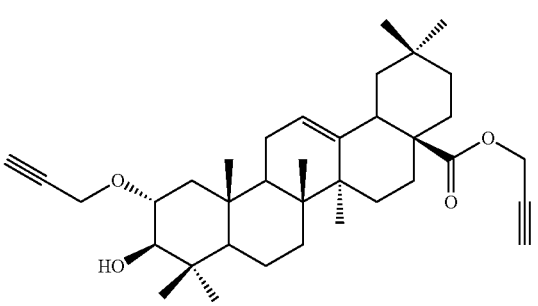

wherein the triterpenoid 6 has the chemical structure of Formula VI;

Formula VI

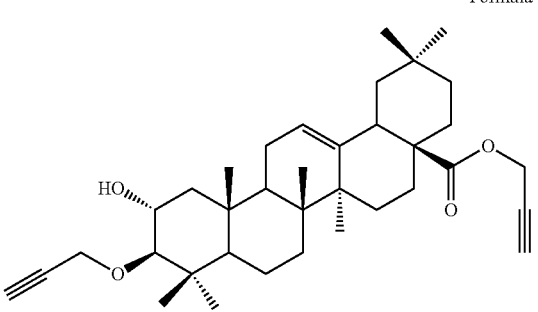

wherein the triterpenoid 7 has the chemical structure of Formula VII;

Formula VII

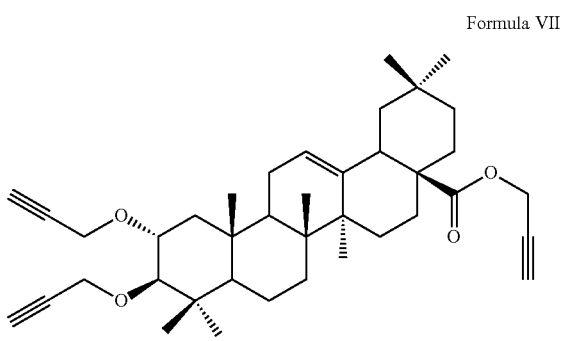

wherein the triterpenoid 8 has the chemical structure of Formula VIII;

Formula VIII

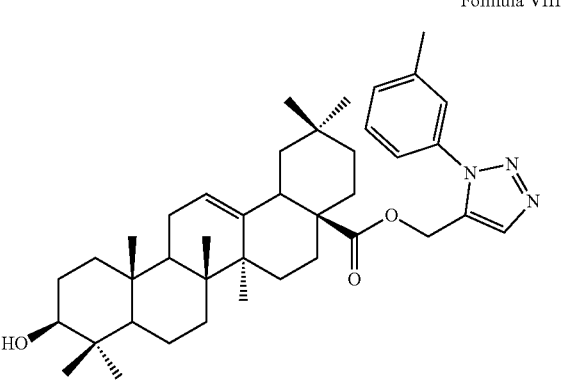

wherein the triterpenoid 9 has the chemical structure of Formula IX;

Formula IX

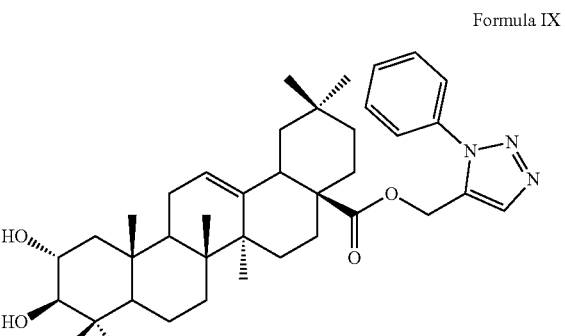

wherein the triterpenoid 10 has the chemical structure of Formula X;

Formula X
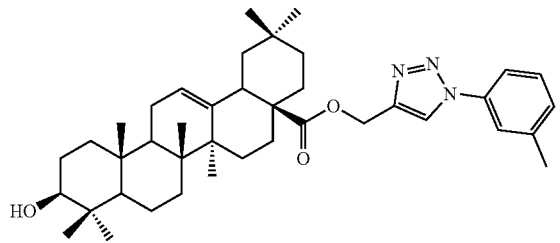
wherein the triterpenoid 11 has the chemical structure of Formula XI;
Formula XI
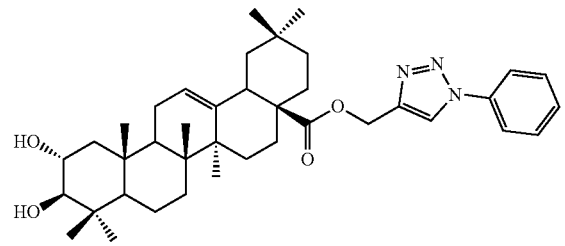
wherein the triterpenoid 12 has the chemical structure of Formula XII;
Formula XII
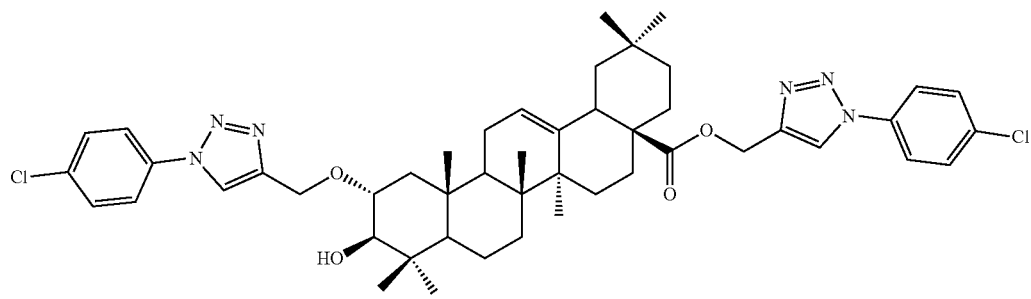
wherein the triterpenoid 13 has the chemical structure of Formula XIII;
Formula XIII
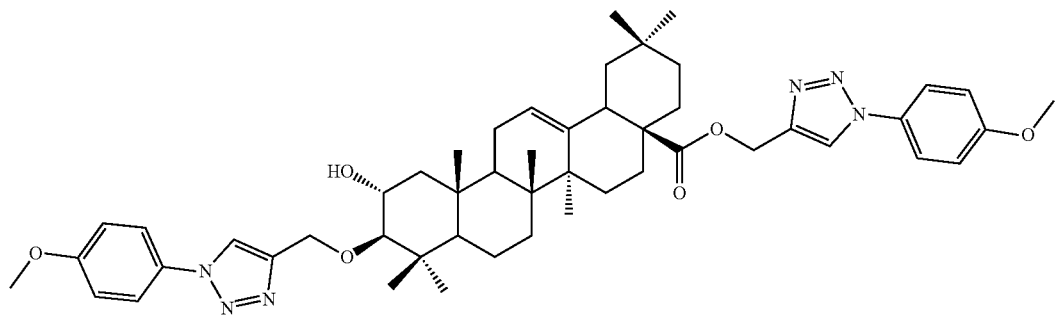
wherein the triterpenoid 14 has the chemical structure of Formula XIV;
Formula XIV
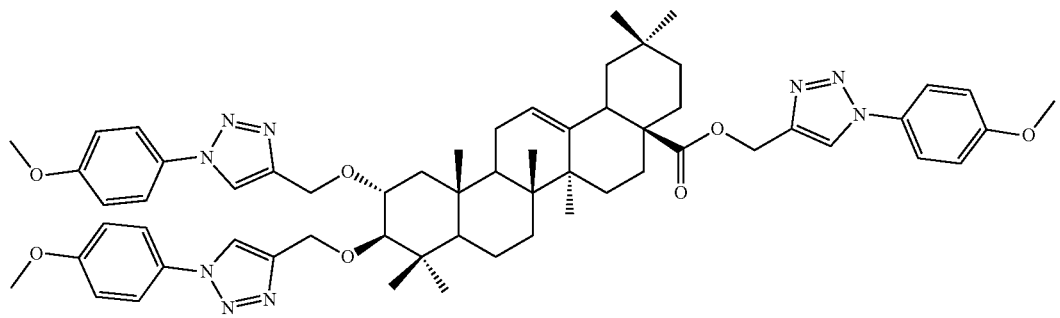

wherein the triterpenoid 15 has the chemical structure of Formula XV;

Formula XV wherein the triterpenoid 16 has the chemical structure of Formula XVI;

Formula XVI wherein the triterpenoid 17 has the chemical structure of Formula XVII.

Formula XVII

4. The method of claim 3, wherein the composition further comprises a combination of two or more of the at least one triterpenoid selected from the group of triterpenoids having a chemical structure as set forth in Formulas III-XVII.

5. The method of claim 3, wherein the amount sufficient to inhibit the coronavirus growth is a concentration of the compound to partially or completely inhibit at least one proteolytic activity of SARS-CoV-2 main protease.

6. The method of claim 5, wherein the compound directly interacts with at least one amino acid of the SARS-CoV-2 main protease.

* * * * *

UNITED STATES PATENT AND TRADEMARK OFFICE
CERTIFICATE OF CORRECTION

PATENT NO. : 11,266,632 B1
APPLICATION NO. : 17/380325
DATED : March 8, 2022
INVENTOR(S) : R Soltane et al.

It is certified that error appears in the above-identified patent and that said Letters Patent is hereby corrected as shown below:

On the Title Page

Item (72) Please correct the inventors' cities of residence as follows:
Raya Soltane : (Makkah, Saudi Arabia)
Ahlam Alasiri : (Makkah, Saudi Arabia)
Hichem Ben Jannet : (Monastir, Tunisia)
Karim Chouaib : (Monastir, Tunisia)
Amani Chrouda : (Al-Majmaah, Saudi Arabia)
Ahmed Mostafa : (Cairo, Egypt)
Rami Adel Pashameah : (Makkah, Saudi Arabia)

Signed and Sealed this
Nineteenth Day of April, 2022

Katherine Kelly Vidal
*Director of the United States Patent and Trademark Office*